US010231960B2

(12) United States Patent
Guenther et al.

(10) Patent No.: US 10,231,960 B2
(45) Date of Patent: *Mar. 19, 2019

(54) METHYLPHENIDATE-PRODRUGS, PROCESSES OF MAKING AND USING THE SAME

(71) Applicant: KemPharm, Inc., Coralville, IA (US)

(72) Inventors: Sven Guenther, Coralville, IA (US);
Guochen Chi, Coralville, IA (US);
Bindu Bera, Blacksburg, VA (US);
Travis Mickle, Kissimmee, FL (US);
Sanjib Bera, Blacksburg, VA (US)

(73) Assignee: KemPharm Inc., Celebration, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,088

(22) Filed: Aug. 26, 2016

(65) Prior Publication Data
US 2017/0049765 A1 Feb. 23, 2017

Related U.S. Application Data

(60) Division of application No. 14/727,498, filed on Jun. 1, 2015, now Pat. No. 9,453,037, which is a continuation of application No. 14/234,440, filed as application No. PCT/US2012/048641 on Jul. 27, 2012, now Pat. No. 9,079,928.

(60) Provisional application No. 61/512,658, filed on Jul. 28, 2011.

(51) Int. Cl.
C07D 211/68 (2006.01)
C07D 211/60 (2006.01)
A61K 31/4458 (2006.01)
C07F 9/59 (2006.01)
C07D 211/34 (2006.01)
C07K 5/02 (2006.01)
C07K 5/062 (2006.01)
C07D 401/12 (2006.01)
A61K 9/00 (2006.01)
A61K 47/60 (2017.01)
A61K 47/54 (2017.01)
A61K 47/64 (2017.01)

(52) U.S. Cl.
CPC ........ A61K 31/4458 (2013.01); A61K 9/0053 (2013.01); A61K 47/542 (2017.08); A61K 47/545 (2017.08); A61K 47/548 (2017.08); A61K 47/60 (2017.08); A61K 47/64 (2017.08); C07D 211/34 (2013.01); C07D 401/12 (2013.01); C07F 9/59 (2013.01); C07K 5/0202 (2013.01); C07K 5/06026 (2013.01)

(58) Field of Classification Search
CPC .................................................. A61K 31/4458
USPC ........................................................ 546/194
See application file for complete search history.

(56) References Cited

U.S. PATENT DOCUMENTS

| 4,428,935 A * | 1/1984 | Myers ................. C07D 499/00 424/114 |
| 6,210,705 B1 | 4/2001 | Mantelle et al. |
| 8,101,782 B2 * | 1/2012 | Rupniak ............... C07C 271/44 540/551 |
| 8,969,337 B2 | 3/2015 | Blumberg et al. |
| 9,079,928 B2 * | 7/2015 | Guenther ......... A61K 47/48038 |
| 2002/0103162 A1 | 8/2002 | Epstein et al. |
| 2002/0132793 A1 | 9/2002 | Epstein et al. |
| 2004/0063628 A1 | 4/2004 | Piccariello et al. |
| 2006/0100243 A1 | 5/2006 | Froimowitz et al. |
| 2007/0042955 A1 | 2/2007 | Mickle et al. |
| 2007/0123468 A1 | 5/2007 | Jenkins |
| 2008/0139653 A1 | 6/2008 | Mickle |
| 2010/0145057 A1 * | 6/2010 | Thennati ............... C07C 271/60 546/227 |
| 2011/0021564 A1 | 1/2011 | Sanfilippo |
| 2011/0213034 A1 | 9/2011 | Mickle |

FOREIGN PATENT DOCUMENTS

| WO | 1999/036403 | 7/1999 |
| WO | 2004080959 | 9/2004 |
| WO | 2008097546 | 8/2008 |
| WO | 2008147518 A1 | 12/2008 |
| WO | 2009035473 | 3/2009 |
| WO | 2013016668 | 1/2013 |

OTHER PUBLICATIONS

Marriot, Pharmaceutical compounding and dispensing, 2009.*
Alcade, Chem. Commun., 2011, 47, 3266-3268.*
Destevens, G.: "Investigations in Heterocycles. XV. Methylphenidate : A Versatile Intermediate in the Synthesis of Bicyclic Heterocycles with Bridged Nitrogen Atom," J. Med. Chem., pp. 146-149, 1964.
Dias, Luiz C., et al.: "Short Synthesis of Methylphenidate and its p-Methoxy Derivative," Synthetic Communications, vol. 30, No. 7, p. 1313, 2000.
Misra M., et al., "Quantitative structure-activity relationship studies of threo-methylphenidate analogs," Bioorganic & Medicinal Chemistry, Pergamon, GB, vol. 18, No. 20, pp. 7221-7238, 2010.
Pilli et al., "The Stereochemistry of the Addition of Chlorotitanium Enolates of N-Acyl Oxazolidin-2-ones to 5- and 6-Membered N-Acyliminium Ions." J. Braz. Chem. Soc., vol. 12, No. 5, pp. 634-651, 2001.
International Search Report and Written Opinion for International Patent Application No. PCT/US2012/048641 dated Jan. 23, 2013.
Notice of Allowance for U.S. Appl. No. 14/234,440 dated Dec. 4, 2014.

(Continued)

Primary Examiner — Nizal S Chandrakumar
(74) Attorney, Agent, or Firm — McAndrews, Held & Malloy, Ltd.; Robert Hoag

(57) ABSTRACT

The present technology is directed to prodrugs and compositions for the treatment of various diseases and/or disorders comprising methylphenidate, or methylphenidate derivatives, conjugated to at least one alcohol, amine, oxoacid, thiol, or derivatives thereof. In some embodiments, the conjugates further include at least one linker. The present technology also relates to the synthesis of methylphenidate, or methylphenidate derivatives, conjugated to at least one alcohol, amine, oxoacid, thiol, or derivatives thereof or combinations thereof.

5 Claims, 24 Drawing Sheets

(56) References Cited

OTHER PUBLICATIONS

Extended European Search Report for Application No. 12817423.2, dated Jan. 23, 2015.
Notice of Allowance for U.S. Appl. No. 14/234,440 dated Mar. 16, 2015.
Japanese Office Action for JP Appl No. 014-523083, dated Mar. 30, 2016.
Canadian Examiner's Report for Application No. 2,837,732, dated Dec. 12, 2016.
Extended European Search Report for Appl No. 17157635.8, dated May 4, 2017.
India Patent Office, "Examiner's Report," India Patent Application No. 11264/DELNP/2013, dated Jan. 23, 2018.
Korea Patent Office, "Final Rejection," Korean Patent Application No. 10-2016-7010571 dated Jan. 10, 2018.
Notice of Allowance for Korean Patent Application No. 10-2016-7010571 dated Mar. 14, 2018.

\* cited by examiner

STRUCTURES OF SOME HYDROXYBENZOATES

STRUCTURES OF SOME HETEROARYL CARBOXYLIC ACIDS

STRUCTURES OF SOME PHENYLACETATES

STRUCTURES OF SOME BENZYLACETATES 3-phenylpropanoic acid
(benzylacetic acid)

Melilotic acid 3-hydroxyphenyl-
propanoic acid 4-hydroxyphenyl-
propanoic acid 2,3-dihydroxyphenyl-
propanoic acid 3,4-dihydroxyphenyl-
propanoic acid Phenyllactic acid

STRUCTURES OF SOME CINNAMATES

STRUCTURES OF SOME DICARBOXYLIC ACIDS

STRUCTURES OF SOME TRICARBOXYLIC ACIDS

GENERAL STRUCTURES OF SOME INORGANIC OXOACIDS

Phosphate

Phosphonate

Phosphinate

Phosphoramidate

Phosphoramidite

Diphosphate

Triphosphate

Biphosphonate

Phosphorothioate

Sulfate

Sulfonate

Sulfamate

Sulfite

Thiosulfate

Thiosulfite

Sulfinate

Nitrate

Nitrite

Borate

Boronate

Hypochlorite

Carbonate

Carbamate $R, R^1, R^2, R^3, R^4, R^5$ = alkyl or aryl.

STRUCTURES OF SOME INORGANIC OXOACID DERIVATIVES

Phosphate

2-Aminoethyl-
phosphonate

Dimethylphosphate

Etidronate

Sulfate

Sulfamate

Tosylate

GENERAL STRUCTURES OF THE STANDARD AMINO ACIDS

R =

| | | | |
|---|---|---|---|
| -H | Glycine | | Histidine |
| -CH₃ | Alanine | | Serine |
| | Phenylalanine | | Cysteine |
| | Tyrosine | | Threonine |
| | Aspartic acid | | Methionine |
| | Glutamic acid | | Valine |
| | Asparagine | | Leucine |
| | Glutamine | | Isoleucine |
| | Lysine | | Tryptophan |
| | Arginine | | Proline |
| | Selenocysteine | | Pyrrolysine |

STRUCTURES OF SOME NON-STANDARD AMINO ACIDS

4-Hydroxyproline

5-Hydroxylysine

5-Hydroxy-tryptophan

3-Hydroxyleucine

4-Hydroxyisoleucine

1-Aminocyclopropyl-1-carboxylic acid

Azetidine-2-carboxylic acid

Pipecolic acid

STRUCTURES OF SOME SYNTHETIC AMINO ACIDS

Allo-isoleucine tert-Leucine

3-Phenylserine

Isoserine

3-Aminopentanoic acid

2-Amino-octanedioic acid

4-Chloro-β-phenylalanine

β-Homoproline

β-Homoalanine

3-Amino-3-(3-methoxyphenyl) propionic acid

N-Isobutyryl-cysteine

3-Amino-tyrosine

5-Methyl-tryptophan 2,3-Diaminopropionic Acid

5-Aminovaleric acid 4-(Dimethylamino)cinnamic acid

METHYLPHENIDATE-PRODRUGS, PROCESSES OF MAKING AND USING THE SAME

RELATED APPLICATIONS

This application is a divisional of U.S. application Ser. No. 14/727,498, filed Jun. 1, 2015 which is continuation of and claims priority to U.S. application Ser. No. 14/234,440, filed on May 15, 2014, which is a National Stage Entry of PCT/US2012/048641, filed on Jul. 27, 2012, which claims priority to and benefit from U.S. Provisional Application No. 61/512,658, entitled METHYLPHENIDATE-OXOACID CONJUGATES, PROCESSES OF MAKING AND USING THE SAME, filed Jul. 28, 2011, all of which are incorporated herein by reference in their entireties.

FEDERALLY SPONSORED RESEARCH OR DEVELOPMENT

[Not Applicable]

BACKGROUND OF THE INVENTION

Methylphenidate is a psychostimulant which is a chain substituted amphetamine derivative. Similar to amphetamine and cocaine, methylphenidate targets the central nervous system, specifically the dopamine transporter (DAT) and norepinephrine transporter (NET). Methylphenidate is thought to act by increasing the concentrations of dopamine and norepinephrine in the synaptic cleft, as methylphenidate has both dopamine transporter (DAT) and norepinephrine transporter (NET) binding capabilities. Although an amphetamine derivative, the pharmacology of methylphenidate and amphetamine differ, as amphetamine is a dopamine transport substrate whereas methylphenidate works as a dopamine transport blocker. As a norepinephrine and dopamine re-uptake inhibitor, methylphenidate thus blocks re-uptake of dopamine and norepinephrine (noradrenaline) into presynaptic neurons (and possibly stimulates the release of dopamine from dopamine nerve terminals at high doses), thereby increasing the levels of dopamine and norepinephrine in the synapse. In some in vitro studies, methylphenidate has been shown to be more potent as an inhibitor of norepinephrine uptake/re-uptake when compared to dopamine. However, some in vivo studies have indicated that methylphenidate is more potent in potentiating extracellular dopamine concentrations than norepinephrine concentrations. Unlike amphetamine, it has been duggested in the scientific and/or clinical research comunity that methylphenidate does not seem to significantly facilitate the release of these two monoamine neurotransmitters at therapeutic doses.

Four isomers of methylphenidate are known to exist: d-erythro-methylphenidate, l-erythro-methylphenidate, d-threo-methylphenidate, and l-threo-methylphenidate. Originally, methylphenidate was marketed as a mixture of two racemates, d/l-erythro-methylphenidate and d/l-threo-methylphenidate. Subsequent research showed that most of the pharmacological activity of the mixture is associated with the threo-isomer resulting in the marketing of the isolated threo-methylphenidate racemate. Later, the scientific community determined that the d-threo-isomer is mostly responsible for the stimulant activity. Consequently, new products were developed containing only d-threo-methylphenidate (also known as "d-threo-MPH").

Stimulants, including methylphenidate ("MPH"), are believed to enhance the activity of the sympathetic nervous system and/or central nervous system (CNS). Stimulants such as MPH and the various forms and derivatives thereof are used for the treatment of a range of conditions and disorders predominantly encompassing, for example, attention deficit hyperactivity disorder (ADHD), attention deficit disorder (ADD), obesity, narcolepsy, appetite suppression, depression, anxiety and/or wakefulness.

Methylphenidate is currently approved by the United States Food and Drug Administration ("FDA") for the treatment of attention-deficit hyperactivity disorder and narcolepsy. Methylphenidate has also shown efficacy for some off-label indications that include depression, obesity and lethargy. In some embodiments, the prodrugs of the present technology may be administered for the treatment of attention-deficit hyperactivity disorder and narcolepsy, or any condition that requires the blocking of the norepinephrine and/or dopamine transporters.

Attention deficit hyperactivity disorder (ADHD) in children has been treated with stimulants for many years. However, more recently, an increase in the number of prescriptions for ADHD therapy in the adult population has, at times, outperformed the growth of the pediatric market. Although there are various drugs currently in use for the treatment of ADHD, including some stimulants and some non-stimulant drugs, methylphenidate (commercially available from, for example, Novartis International AG (located in Basel, Switzerland) under the trademark Ritalin®) is commonly prescribed. Moreover, during classroom trials, non-stimulants have shown to be less effective in improving behavior and attention of ADHD afflicted children than amphetamine derivatives.

Behavioral deterioration (rebound or "crashing") is observed in a significant portion of children with ADHD as the medication wears off, typically in the afternoon or early evening. Rebound symptoms include, for example, irritability, crankiness, hyperactivity worse than in the unmedicated state, sadness, crying, and in rare cases psychotic episodes. The symptoms may subside quickly or last several hours. Some patients may experience rebound/crashing so severe that treatment must be discontinued. Rebound/crashing effects can also give rise to addictive behavior by enticing patients to administer additional doses of stimulant with the intent to prevent anticipated rebound/crashing negative outcomes and side effects.

Stimulants, such as methylphenidate and amphetamine, have been shown in the conventional art to exhibit noradrenergic and dopaminergic effects that can lead to cardiovascular events comprising, for example, increased heart rate, hypertension, palpitations, tachycardia and in isolated cases cardiomyopathy, stroke, myocardial infarction and/or sudden death. Consequently, currently available stimulants expose patients with pre-existing structural cardiac abnormalities or other severe cardiac indications to even greater health risks and are frequently not used or used with caution in this patient population.

Methylphenidate, like other stimulants and amphetamine derivatives, can become addictive and is prone to substance abuse. Oral abuse has been reported, and euphoria can be achieved through intranasal and intravenous administration.

Methylphenidate also has limited water solubility especially in an unconjugated form. The properties of limited bioavailability and limited water solubility make formulating methylphenidate for oral administration more difficult because the dosage forms for administration are limited. There is a need in the art for more bioavailable and water soluble forms of methylphenidate that maintain the pharmacological benefit when administered, in particular via the oral route.

BRIEF SUMMARY OF THE INVENTION

The present technology utilizes, for example, covalent conjugation of methylphenidate, various forms and derivatives thereof with certain alcohol, amine, oxoacid, thiol, or derivatives thereof to provide, for example, improved bioavailability and increased water solubility when compared to unconjugated methylphenidate. The increased bioavailability and/or increased water solubility in some instances provides the ability of the prodrug or composition to be administered in forms that are not easily utilized with the unconjugated methylphenidate. For example, the increased water solubility of the conjugate compared to unconjugated methylphenidate provides the ability of the conjugate or prodrug to be administered in an oral thin film or strip with higher dose loading capacity as compared to unconjugated methylphenidate In one aspect, the present technology provides a prodrug composition comprising at least one conjugate, the conjugate comprising at least one methylphenidate, and at least one alcohol, amine, oxoacid, thiol, or derivatives thereof. In some aspects, the prodrug composition further comprises a linker, wherein the linker chemically bonds the at least one methylphenidate with the at least one alcohol, amine, oxoacid, thiol, or derivatives thereof. In some aspects, the linker comprises at least one (acyloxy)alkyloxy moiety, derivatives thereof, or combinations thereof.

In further aspects, the present technology provides one or more conjugates of methylphenidate comprising methylphenidate, a derivative thereof, or combinations thereof and at least one alcohol, amine, oxoacid, thiol, or derivatives thereof, wherein the at least one oxoacid is a carboxylic acid.

In another aspect, the present technology provides at least one prodrug composition comprising at least one conjugate of methylphenidate, derivatives thereof or combinations thereof and at least one inorganic oxoacid, or derivatives thereof with a free —OH group, an organic derivative thereof, an inorganic derivative thereof, or a combination thereof.

In a further aspect, the present technology provides at least one prodrug composition comprising at least one conjugate of methylphenidate, derivatives thereof or combinations thereof and an alcohol, amine, oxoacid, thiol, or derivatives thereof and a linker, wherein the linker comprises an (acyloxy)alkyloxy group, a derivative thereof or combination thereof with the general formula —C(O)O—X—O—, wherein, X is selected from a representative group including optionally substituted alkyl, optionally substituted aryl, optionally substituted alkylaryl, optionally substituted heteroalkyl, optionally substituted heteroaryl, optionally substituted heterocycle, optionally substituted alkenyl, optionally substituted alkynyl, optionally substituted cycloalkyl, optionally substituted cycloalkenyl, optionally substituted cycloalkynyl, or optionally substituted alkoxy.

In another aspect, the present technology provides a prodrug composition comprising at least one conjugate of methylphenidate having a structure of formula (I) or formula (II):

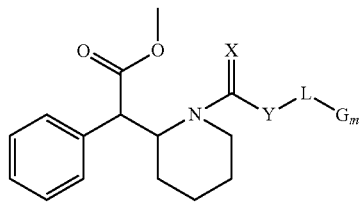

(I)

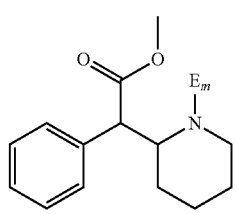

(II)

wherein X is selected from the group consisting of O, S, Se and $NR^1$; wherein Y is absent or selected from the group consisting of O, S, Se, $NR^2$ and $CR^3R^4$; wherein $R^1$ and $R^2$ are selected independently from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, polycycloalkenyl, polycycloalkenylalkyl, polycycloalkyl, polycycloalkylalkyl, and polyethylene glycol; wherein $R^3$ and $R^4$ are selected independently from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, oxo, polycycloalkenyl, polycycloalkenylalkyl, polycycloalkyl, polycycloalkylalkyl, polyethylene glycol and thiol; wherein L is absent or -[-A-Z—]—$_n$; wherein A is selected independently for each repeating subunit from the group consisting of $CR^5R^6$, aryl, substituted aryl, arylene, carbocycle, cycloalkenyl, cycloalkyl, cycloalkynyl, heterocycle and heteroaryl; wherein $R^5$ and $R^6$ are selected independently from each other and independently for each repeating subunit from the group consisting of hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, oxo, polycycloalkenyl, polycycloalkenylalkyl, polycycloalkyl, polycycloalkylalkyl, polyethylene glycol and thiol; wherein Z is either absent or selected independently for each repeating subunit from the group consisting of O, S, Se and NH; wherein n is 0-50; wherein G is selected independently for each repeating subunit from the group consisting of alcohol, amine, amino acid, ammonium, oxoacid, peptide, poly(ethylene glycols) (PEG), thiol, derivatives thereof and combinations thereof; wherein E is an oxoacid; and wherein m is 0-5.

In another aspect, the present technology provides at least one prodrug composition comprising at least one conjugate, wherein the at least one conjugate can be, for example, nicotinate-$CH_2OCO$-methylphenidate, phosphate-$CH_2OCO$-methylphenidate, phosphate-$CH_2OCO$-methylphenidate, gallate-$CH_2OCO$-methylphenidate, gallate-$CH_2OCO$-methylphenidate, lactate-$CH_2OCO$-methylphenidate, methylphenidate-$CO_2CH_2$-nicotinoyl-Asp, methylphenidate-$CO_2CH_2$-nicotinoyl-Val, methylphenidate-$CO_2CH_2$-nicotinoyl-Gly-Ala, Val-6-aminohexanoate-$CH_2OCO$-methylphenidate, methylphenidate-$CO_2CH_2$-nicotinamide, 6-Aminohexanoate-$CH_2OCO$-methylphenidate, methylphenidate-$CO_2CH_2$-nicotinoyl-O'Bu, methylphenidate-$CO_2CH_2$-nicotinate, methylphenidate-$CO_2CH_2$-nicotinoyl-OEt, methylphenidate-$CO_2CH_2$-pyridine, isonicotinate-$CH_2OCO$-methylphenidate, or phosphate-(p-salicylate)-$CH_2OCO$-methylphenidate.

Moreover, the present technology provides at least one prodrug composition comprising at least one oxyalkyl carbamate.

In yet another aspect, the present technology provides a method for chemically synthesizing any of the methylphenidate conjugates of the present technology by perforing the appropriate steps to conjugate methylphenidate to at least one ligand.

In further aspects, prodrug compositions of the present technology are believed to unexpectedly exhibit a rate of release equivalent to free or unmodified methylphenidate. In other aspects, the one or more prodrug composition of the present technology are believed to surprisingly exhibit a slower rate of release over time as compared to unmodified methylphenidate.

In yet other aspects, conjugates or prodrugs of the present technology are believed to unexpectedly exhibit an increased absorption when administered orally as compared to unmodified methylphenidate. Additionally, conjugates or prodrugs of the present technology are believed to surprisingly have increased bioavailability as compared to unmodified methylphenidate.

In yet a further aspect, the conjugates or prodrugs of the present technology are believed to surprisingly exhibit less interpatient variability in the oral pharmacokinetic (PK) profile when compared to unconjugated methylphenidate.

In yet another aspect, the conjugates or prodrugs of the present technology are provided in an amount sufficient to provide an increased AUC when compared to unconjugated methylphenidate when administered orally at equimolar doses. In still other aspects, the conjugates or prodrugs are provided in an amount sufficient to provide an unexpected increased $C_{max}$ as compared to unconjugated methylphenidate when administered orally at equimolar doses.

In yet further aspects, the conjugates or prodrugs of the present technology are provided in an amount sufficient to provide a surprisingly increased $C_{max}$ and an increased AUC as compared to unconjugated methylphenidate when administered orally at equimolar doses.

In yet an alternative aspect, the conjugates or prodrugs of the present technology provide reduced side effects as compared to unconjugated methylphenidate when administered at equimolar doses, and are also contemplated in some alternative aspects to provide reduced abuse potential as compared to unconjugated methylphenidate.

In addition, the conjugates or prodrugs of the present technology are also believed to unexpectedly provide an amount sufficient to provide an extended $T_{max}$ when compared to unconjugated methylphenidate when administered at equimolar doses, and/or provide an equivalent $T_{max}$ when compared to unconjugated methylphenidate when administered at equimolar doses.

Moreover, the present technology provides at least one method of treating one or more patients (human or animal) having at least one disease, disorder or condition mediated by controlling, preventing, limiting, or inhibiting neurotransmitter uptake/re-uptake or hormone uptake/re-uptake comprising orally administering to one or more patients a pharmaceutically effective amount of at least one of the prodrug compositions of the present technology.

In still yet a further aspect, the present technology provides at least one method of treating a patient (human or animal) having at least one disorder or condition requiring stimulation of the central nervous system of the patient, comprising orally administering a pharmaceutically effective amount of one or more prodrug compositions of the present technology.

In yet another aspect, the present technology provides one or more methods of administering at least one [methylphenidate] composition or prodrug of the present technology wherein the administration decreases the number and/or amount of metabolites produced when compared with unconjugated methylphenidate. In other aspects, the one or more methods of administering the one or more [methylphenidate] compositions or prodrugs of the present technology is believed to decrease the exposure of the patient to ritalinic acid when compared with unconjugated methylphenidate.

In yet a further embodiment, the one or more compositions or prodrugs of the present technology are believed to provide an increased water solubility of the methylphenidate-based conjugate or prodrug compared to unconjugated methylphenidate. In another embodiment, the increased water solubility is believed to allow for the prodrug to be formed into certain dosage forms at higher concentrations, dosage strengths, or higher dose loading capacities than unconjugated methylphenidate. In some embodiments, such dosage forms include, for example, oral thin films or strips with.

In still yet a further embodiment, the administration of one or more methylphenidate-based compositions or prodrugs are believed to provide a reduced interpatient variability of methylphenidate plasma concentrations, and are believed to have an improved safety profile when compared to unconjugated methylphenidate.

In yet another alternative embodiment, the present technology provides at least one method of treating attention-deficit hyperactivity disorder comprising administering a pharmaceutically effective amount of one or more conjugates or prodrug compositions of the present technology.

In another further embodiment, the present technology provides at least one prodrug composition for treating at least one patient having a disorder or condition requiring stimulation of the central nervous system of the patient, wherein the at least one prodrug or composition has a reduced abuse potential when administered compared to unconjugated methylphenidate.

In a further embodiment, the one or more methylphenidate-based prodrug or conjugate compositions of the present technology are contemplated to exhibit reduced or prevented pharmacological activity when administered by parenteral routes, or reduced plasma or blood concentration of released methylphenidate when administered intranasally, intravenously, intramuscularly, subcutaneously or rectally as compared to free unconjugated methylphenidate when administered at equimolar amounts.

In yet another embodiment, the present technology provides at least one methylphenidate-based conjugate prodrug composition having an extended or controlled release profile as measured by plasma concentrations of released methylphenidate when compared to unconjugated methylphenidate when administered orally at equimolar doses. In some embodiments, the plasma concentration of methylphenidate released from the prodrug would increase more slowly and over a longer period of time after oral administration, resulting in a delay in peak plasma concentration of released methylphenidate and in a longer duration of action when compared to unconjugated methylphenidate.

In another aspect, the present technology provides a pharmaceutical kit comprising a specified amount of individual doses in a package containing a pharmaceutically effective amount of at least one conjugate of methylphenidate.

DETAILED DESCRIPTION OF THE INVENTION

Figure 1:
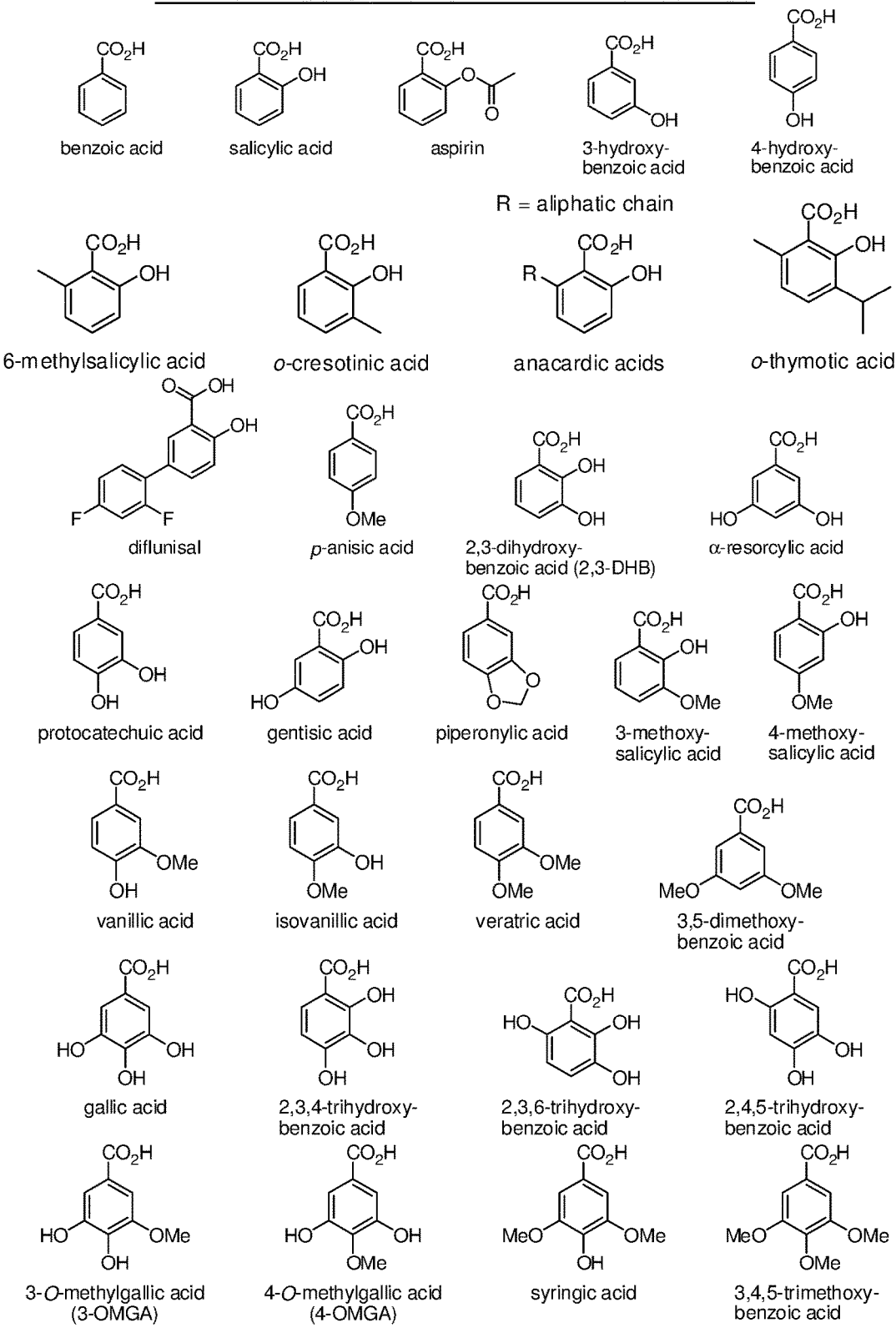
FIG. 1. Chemical structures of some hydroxybenzoates for use in the making of the conjugates of the present technology.

The present technology provides at least one methylphenidate or one or more derivatives or combinations thereof (MPH, methyl phenyl(piperidin-2-yl)acetate) conjugated to at least one organic or inorganic oxoacid to form oxylalkyl carbamates, which are novel prodrugs compositions and/or conjugates of methylphenidate. In some embodiments, the at least one conjugate or prodrug of the present technology was surprisingly discovered by conjugating methylphenidate to a series of organic or inorganic oxoacids through various linker molecules. In some embodiments, the linkers are (acyloxy)alkyloxy moieties or derivatives thereof. The linker chain is connected on one end to methylphenidate via a secondary carbamate bond and on the other to the oxoacid via an ester bond.

The use of the term "methylphenidate" herein is meant to include any of the stereoisomer forms of methylphenidate, including the four stereoisomers: d-erythro-methylphenidate, l-erythro-methylphenidate, d-threo-methylphenidate and l-threo-methylphenidate and the salts and derivatives thereof. Methylphenidate is interchangeable with methyl phenyl(piperidin-2-yl)acetate. The term "methylphenidate" includes all salt forms. Methylphenidate is also known by its trade name Ritalin®, Ritalin® SR, Methylin®, Methylin® ER (all commercially available from Novartis International AG, of Basil, Switzerland). The methylphenidate used in the present technology can be any stereoisomer of methylphenidate, including, but not limited to, d-erythro-methylphenidate, l-erythro-methylphenidate, d-threo-methylphenidate and l-threo-methylphenidate. In some embodiments, the methylphenidate can be a mixture of two or more racemates, for example, but not limited to, d/l-erythro-methylphenidate and d/l-threo-methylphenidate. In some preferred embodiments, the conjugates contain racemic threo-methylphenidate. In other preferred embodiments, the alcohol, amine, oxoacid, or thiol is linked to a single d-threo-methylphenidate isomer. Depending on the chemical structure of the linkers and alcohols, amines, oxoacids, and thiols as well as the chiral composition of the methylphenidate to which they are attached, the resulting prodrug conjugates can be optically active mixtures of isomers, racemic mixtures, single isomers or combinations thereof.

As used herein, the phrases such as "decreased," "reduced," "diminished" or "lowered" are meant to include at least about a 10% change in pharmacological activity, area under the curve (AUC) and/or peak plasma concentration ($C_{max}$) with greater percentage changes being preferred for reduction in abuse potential and overdose potential of the conjugates of the present technology as compared to unconjugated methylphenidate. For instance, the change may also be greater than about 10%, about 15%, about 20%, about 25%, about 35%, about 45%, about 55%, about 65%, about 75%, about 85%, about 95%, about 96%, about 97%, about 98%, about 99%, or increments therein.

As used herein, the term "prodrug" refers to a substance converted from an inactive form of a drug to an active drug in the body by a chemical or biological reaction. In the present technology, the prodrug is a conjugate of at least one drug, methylphenidate, and at least one oxoacid, for example. Thus, the conjugates of the present technology are prodrugs and the prodrugs of the present technology are conjugates.

Prodrugs are often useful because, in some embodiments, they may be easier to administer or process than the parent drug. They may, for instance, be more bioavailable by oral administration whereas the parent drug is not. The prodrug may also have improved solubility in pharmaceutical compositions over the parent drug. An embodiment of a prodrug would be a methylphenidate conjugate that is metabolized to reveal the active moiety. In certain embodiments, upon in vivo administration, a prodrug is chemically converted to the biologically, pharmaceutically or therapeutically more active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug is designed to alter the metabolism or the transport characteristics of a drug in certain embodiments, to mask side-effects or toxicity, to improve bioavailability and/or water solubility, to improve the flavor of a drug or to alter other characteristics or properties of a drug in other discrete embodiments.

In some embodiments, the present technology provides at least one prodrug composition comprising at least one conjugate. The at least one conjugate may comprise at least one methylphenidate and at least one alcohol, amine, oxoacid, thiol, or derivatives therof. In some embodiments, the conjugate further comprises at least one linker. The linker chemically bonds the methylphenidate to the alcohol, amine, oxoacid, or thiol via one or more covalent bonds.

Depending on the linker and the alcohol, amine, oxoacid, and thiol conjugated to methylphenidate or derivative thereof, the at least one prodrug formed can be either a neutral (uncharged), a free acid, a free base or a pharmaceutically acceptable anionic or cationic salt form or salt mixtures with any ratio between positive and negative components. These anionic salt forms can include, but are not limited to, for example, acetate, l-aspartate, besylate, bicarbonate, carbonate, d-camsylate, l-camsylate, citrate, edisylate, formate, fumarate, gluconate, hydrobromide/bromide, hydrochloride/chloride, d-lactate, l-lactate, d,l-lactate, d,l-malate, l-malate, mesylate, pamoate, phosphate, succinate, sulfate, bisulfate, d-tartrate, kartrate, d,l-tartrate, mesotartrate, benzoate, gluceptate, d-glucuronate, hybenzate, isethionate, malonate, methylsufate, 2-napsylate, nicotinate, nitrate, orotate, stearate, tosylate, thiocyanate, acefyllinate, aceturate, aminosalicylate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesufonate, myristate, napadisilate, oleate, oxalate, palmitate, picrate, pivalate, propionate, pyrophosphate, salicylate, salicylsulfate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, or undecylenate. The cationic salt forms can include, but are not limited to, for example, sodium, potassium, calcium, magnesium, zinc, aluminium, lithium, cholinate, lysinium, ammonium, or tromethamine.

Without wishing to be limited to the following theory, it is believed that the prodrugs/conjugates of the present technology undergo enzyme hydrolysis of the ester bond in vivo, which subsequently leads to a cascade reaction resulting in rapid regeneration of methylphenidate and the respective oxoacid, metabolites thereof and/or derivatives thereof. The alcohols, amines, oxoacids, thiols, or derivatives therof, of the present technology are non-toxic or have very low toxicity at the given dose levels and are preferably known drugs, natural products, metabolites, or GRAS (Generally Recognized As Safe) compounds (e.g., preservatives, dyes, flavors, etc.) or non-toxic mimetics or derivatives thereof.

General Structures And Definitions

Abbreviations for the components of conjugates of the present technology include: MPH stands for methylphenidate; MPH.HCl stands for methylphenidate hydrochloride; Asp stands for aspartate; Val stands for valine; $^t$Bu stands for tert-butyl; Et stands for ethyl.

In some embodiments, the general structure of the prodrugs of methylphenidate of the present technology can be represented either by formula (I) or by formula (II):

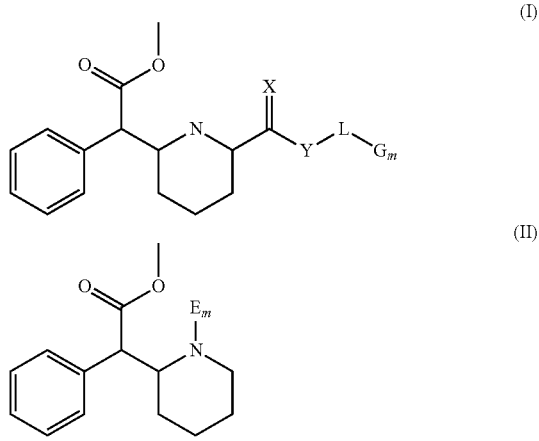

To simplify the drawings, formulas (I) and (II) can also be depicted as:

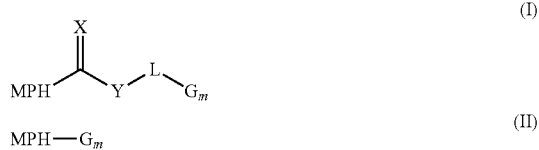

wherein X is selected from O, S, Se or NR$^1$;
Y is absent or selected from O, S, Se, NR$^2$ or CR$^3$R$^4$;
R$^1$ and R$^2$ are selected independently from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, polycycloalkenyl, polycycloalkenylalkyl, polycycloalkyl, polycycloalkylalkyl, or polyethylene glycol;

R$^3$ and R$^4$ are selected independently from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, oxo, polycycloalkenyl, polycycloalkenylalkyl, polycycloalkyl, polycycloalkylalkyl, polyethylene glycol or thiol;

L is absent or $$-\!\!\left[\mathrm{A}\!-\!\mathrm{Z}\right]_{\!n}\!\!-;$$

A is selected independently for each repeating subunit from CR$^5$R$^6$ or optionally substituted aryl, arylene, carbocycle, cycloalkenyl, cycloalkyl, cycloalkynyl, heterocycle, heteroaryl;

R$^5$ and R$^6$ are selected independently from each other and independently for each repeating subunit from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, oxo, polycycloalkenyl, polycycloalkenylalkyl, polycycloalkyl, polycycloalkylalkyl, polyethylene glycol or thiol;

Z is either absent or selected independently for each repeating subunit from O, S, Se or NH;

n is 0-50;

G is selected independently for each repeating subunit from alcohol, amine, amino acid, ammonium, oxoacid, peptide, poly(ethylene glycols) (PEG) or thiol, or derivatives thereof or combinations thereof;

E is an oxoacid; and m is 0-5.

In some embodiments of formula (I), one or more G entities are covalently bound to L, Y (if L absent), or to another G (e.g., one or more than one additional G). Multiple occurrences of G can be all identical, all uniquely different or a mixture of both. In some embodiments of formula (II), one or more E entities (up to m entities) are covalently bound to the nitrogen in the piperidine ring of methylphenidate or to another E. Multiple occurrences of E can be all identical, all uniquely different or a mixture of both.

In some preferred embodiments of formula (I), X is O.

In some preferred embodiments of formula (I), Y is absent or selected from O or N. In some additional preferred embodiments of formula (I), Y is N.

In other preferred embodiments of formula (I), L is selected from:

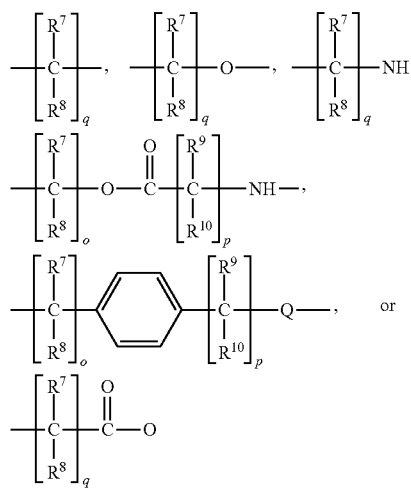

wherein $R^7$, $R^8$, $R^9$, $R^{10}$ are independently selected for each repeating subunit from hydrogen, alkenyl, alkoxy, alkyl, alkynyl, aryl, substituted aryl, alkylaryl, cycloalkenyl, cycloalkyl, cycloalkynyl, heteroalkyl, heteroaryl, or heterocycle. Preferably, $R^7$ and $R^9$ are independently selected for each repeating subunit from hydrogen, alkyl, alkoxy, aryl or substituted aryl, and $R^8$ and $R^{10}$ are preferably hydrogen;

q is 1-10, preferably 1-5;

o and p are 0-10, preferably 0-2; and

Q is NH or O.

In some additional preferred embodiments of formula (I), L is selected from:

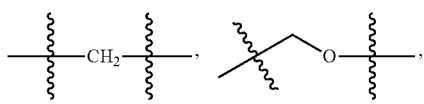

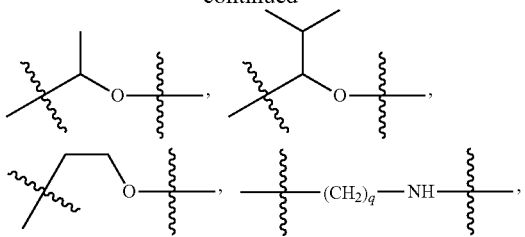

wherein q=1-6;

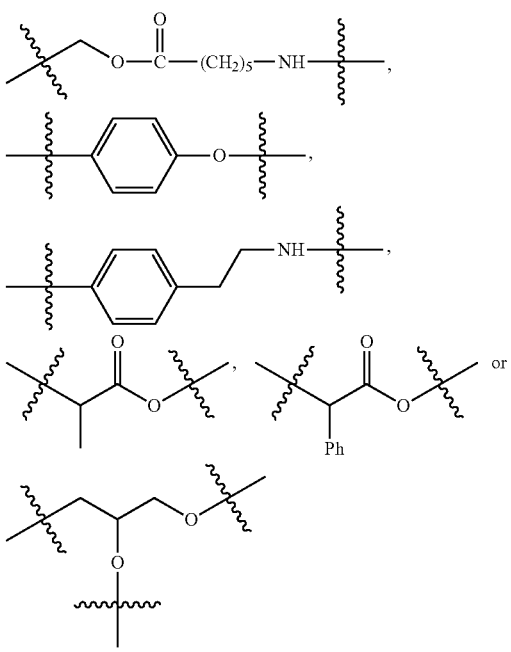

In other preferred embodiments of formula (I), G is selected from oxoacids, tertiary amines or poly(ethylene glycol) derivatives.

In some embodiments of formula (I), G is a tertiary amine that is generally defined by formulas (III) and (IV):

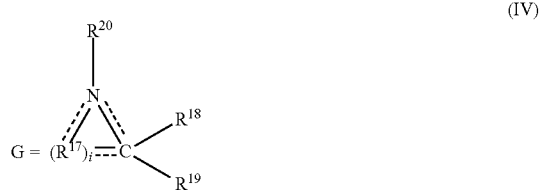

wherein $R^{17}$ is independently selected for each repeating subunit from O, S, Se, $NR^{21}$ or $CR^{22}R^{23}$;

$R^{14}$, $R^{15}$, $R^{16}$, $R^{20}$, $R^{21}$ are selected independently from alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, polycycloalkenyl, polycycloalkenylalkyl, polycycloalkyl, polycycloalkylalkyl, or polyethylene glycol;

$R^{20}$ may also be absent;

$R^{18}$, $R^{19}$, $R^{22}$, $R^{23}$ are selected independently from each other and independently for each repeating subunit (of $R^{17}$) from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, amine, amino, aminocarbonyl, ammonium, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cyano, cycloalkenyl, cycloalkenylalkyl, carboxyl, cycloalkyl, cycloalkylalkyl, cycloalkylamino, cycloalkyloxy, cycloalkynyl, cycloheteroalkyl, cycloheteroalkylalkyl, halo, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, nitro, oxo, polycycloalkenyl, polycycloalkenylalkyl, polycycloalkyl, polycycloalkylalkyl, polyethylene glycol or thiol; and i is 0-10.

In some embodiments, formula (IV) is a heterocycle with a ring size of 3-10 atoms, of which at least one is a nitrogen atom and at least one is a carbon atom, and the ring may be aliphatic containing any chemically feasible number and combination of single, double or triple bonds or the ring may be aromatic.

In other embodiments, G is covalently bound to L via its tertiary nitrogen (see formulas (III) and (IV)) or via an amino, hydroxyl or carboxyl functional group of one of its substituents.

In some preferred embodiments of formula (I), the tertiary amines are defined by formula (V), a a sub-class of formula (IV) wherein:

(V)

and $R^{18}R^{22}$ and $R^{23}$ are as defined for formula (IV).

Some additional preferred embodiments of formula (V) are defined by formulas (VI), (VII) and (VIII):

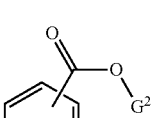
(VI)

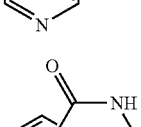
(VII)

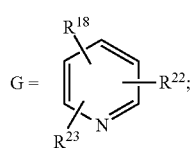
(VIII)

In these embodiments of formula (V), G is a carboxypyridine derivative, preferably nicotinic acid, optionally bound via an ester or amide bond to a second moiety, $G^2$. In some embodiments, $G^2$ is preferably an alcohol or an oxoacid, more preferably an amino acid.

In these embodiments of formula (VIII), $R^{26}$ is selected from hydrogen, alkenyl, alkenylaminocarbonyl, alkoxy, alkoxycarbonyl, alkyl, alkylamino, alkylaminocarbonyl, alkylammonium, alkylcarbonyl, alkylcarbonylamino, alkylcarbonyloxy, alkylsulfinyl, alkylsulfonyl, alkylthio, alkynyl, alkynylaminocarbonyl, aminocarbonyl, aryl, substituted aryl, arylalkenyl, arylalkoxy, arylalkyl, arylalkynyl, arylamino, arylaminocarbonyl, arylammonium, arylazo, arylcarbonyl, arylcarbonylamino, arylcarbonyloxy, arylcycloalkyl, aryloxy, aryloxyalkyl, arylsulfinyl, arylsulfinylalkyl, arylsulfonyl, arylsulfonylamino, arylthio, arylthioalkyl, cycloalkenyl, cycloalkenylalkyl, cycloalkyl, cycloalkylalkyl, cycloalkylamino, cycloalkyloxy, cycloalkynyl, cycloheteroalkyl, cycloheteroalkylalkyl, haloalkoxy, haloalkyl, heteroaryl, heteroarylalkenyl, heteroarylalkyl, heteroarylamino, heteroarylcarbonyl, heteroarylcarbonylamino, heteroaryloxo, heteroaryloxy, heteroarylsulfinyl, heteroarylsulfonyl, heteroarylthio, hydroxy, polycycloalkenyl, polycycloalkenylalkyl, polycycloalkyl, polycycloalkylalkyl, or polyethylene glycol.

In some embodiments of formula (VIII), $R^{26}$ is preferably hydrogen or alkyl.

In other embodiments of formula (I), the poly(ethylene glycol) derivatives are generally defined by formula (IX):

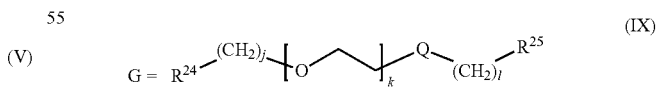
(IX)

wherein $R^{24}$ is H or $NH_2$;
$R^{25}$ is H, $NH_2$ or $CO_2H$;
Q is absent or O;
j and l are 0-5; and
k is 1-100.

In some preferred embodiments of formula (I), the poly(ethylene glycol) derivatives are:

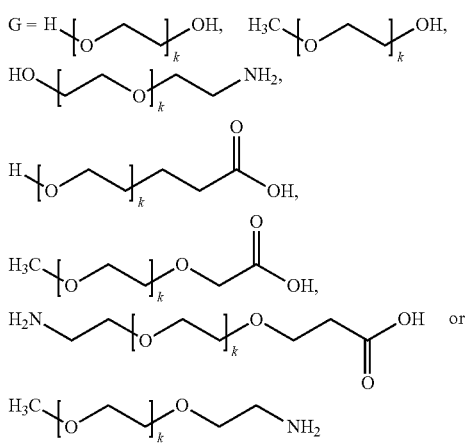

wherein k is 1-100, preferably 1-50 or 1-10.

In some preferred embodiments of formula (II), E is an oxoacid, preferably an amino acid.

Oxoacids

Oxoacids (i.e., oxyacids, oxo acids, oxy-acids, oxiacids, oxacids) of the present technology are a class of compounds which contain oxygen, at least one other element, and at least one hydrogen bound to oxygen, and which produce a conjugate base by loss of positive hydrogen ion(s) (protons). Oxoacids can be categorized into organic acids or inorganic acids and their derivatives. Organic acids include carboxylic acids. Carboxylic acids are widespread in nature (naturally occurring), but carboxylic acids can also be non-natural (synthetic). Carboxylic acids can be categorized into numerous classes based on their molecular structure or formula, and many of the different classes may overlap.

Without wishing to limit the scope to one classification, the carboxylic acids of the present technology can be grouped into the following categories: aliphatic carboxylic acids, aryl carboxylic acids, dicarboxylic, polycarboxylic acids, and amino acids.

Suitable aliphatic carboxylic acids for use in the present technology include, but are not limited to, for example, saturated, monounsaturated, polyunsaturated, acetylenic, substituted (e.g., alkyl, hydroxyl, methoxy, halogenated, etc.), heteroatom containing or ring containing carboxylic acids. Suitable examples of saturated carboxylic acids include, but are not limited to, for example, methanoic, ethanoic, propanoic, butanoic, pentanoic, hexanoic, heptanoic, octanoic, 2-propylpentanoic acid, nonanoic, decanoic, dodecanoic, tetradecanoic, hexadecanoic, heptadecanoic, octadecanoic, or eicosanoic acid. Suitable monounsaturated carboxylic acids for practice of the present technology include, but are not limited to, for example, 4-decenoic, 9-decenoic, 5-lauroleic, 4-dodecenoic, 9-tetradecenoic, 5-tetradecenoic, 4-tetradecenoic, 9-hexadecenoic, 6-hexadecenoic, 6-octadecenoic, or 9-octadecenoic acid.

Suitable polyunsaturated carboxylic acids for use in the present technology include, but are not limited to, for example, sorbic, octadecadienoic, octadecatrienoic, octadecatetraenoic, eicosatrienoic, eicosatetraenoic, eicosapentaenoic, docosapentaenoic, or docosahexaenoic acids. Suitable acetylenic carboxylic acids for use in the present technology include, but are not limited to octadecynoic, octadecenynoic, 6,9-octadecenynoic, heptadecenynoic, tridecatetraenediynoic, tridecadienetriynoic, octadecadienediynoic, heptadecadienediynoic, octadecadienediynoic, octadecenediynoic, or octadecenetriynoic acids.

Suitable substituted carboxylic acids for practice of the present technology include, but are not limited to, for example, methylpropanoic, isovaleric, methylhexadecanoic, 8-methyl-6-nonenoic, methyloctadecanoic, trimethyloctacosanoic, trimethyltetracosenoic, heptamethyltriacontanoic, tetramethylhexadecanoic, tetramethylpentadecanoic, lactic, glyceric, glycolic, threonic, 3-hydroxypropionic, hydroxyoctadecatrienoic, hydroxyoctadecenoic, hydroxytetracosanoic, 2-hydroxybutyric, 3-hydroxybutyric, 4-hydroxybutyric, 4-hydroxypentanoic, hydroxyoctadecadienediynoic, hydroxyoctadecadienoic, 10-hydroxydecanoic, hydroxydecenoic, hydroxyeicosenoic, hydroxyeicosadienoic, hydroxyhexadecanoic, dihydroxytetracosenoic, dihydroxydocosanoic, hydroxydocosanoic, trihydroxyoctadecanoic, trihydroxyhexadecanoic, trihydroxyicosahexaenoic, trihydroxyicosapentaenoic, 2-methoxy-5-hexadecenoic, 2-methoxy hexadecanoic, 7-methoxy-4-tetradecenoic, 9-methoxypentadecanoic, 11-methoxyheptadecanoic, 3-methoxydocosanoic, diacetoxydocosanoic, 2-acetoxydocosanoic, 2-acetoxytetracosanoic, 2-acetoxyhexacosanoic, 9-oxononanoic, oxodecanoic, oxododecenoic, hydroxyoxodecenoic, 10-oxo-8-decenoic, fluorooctadecenoic, fluorodecanoic, fluorotetradecanoic, fluorohexadecanoic, fluorooctadecadienoic, chlorohydroxyhexadecanoic, chlorohydroxyoctadecanoic, dichlorooctadecanoic, 3-bromo-2-nonaenoic, 9,10-dibromooctadecanoic, 9,10,12,13-tetrabromooctadecanoic, 10-nitro-9,12-octadecadienoic, 12-nitro-9,12-octadecadienoic, 9-nitro-9-octadecenoic, 9-oxo-2-decenoic, 9-oxo-13-octadecenoic, oxooctadecatrienoic, 15-oxo-18-tetracosenoic, 17-oxo-20-hexacosenoic, or 19-oxo-22-octacosenoic acids.

Suitable examples of heteroatom containing carboxylic acids include, but are not limited to, for example, 9-(1,3-nonadienoxy)-8-nonenoic, 9-(1,3,6-nonatrienoxy)-8-nonenoic, 12-(1-hexenoxy)-9,11-dodecadienoic, 12-(1,3-hexadienoxy)-9,11-dodecadienoic, 2-dodecylsulfanylacetic, 2-tetradecylsulfanylacetic, 3-tetradecylsulfanylprop-2-enoic, or 3-tetradecylsulfanylpropanoic acid. Suitable examples of ring containing carboxylic acids include, but are not limited to, for example, 10-(2-Hexylcyclopropyl)decanoic, 3-(2-[6-bromo-3,5-nondienylcyclopropyl)propanoic, 9-(2-hexadecylcyclopropylidene)non-5-enoic, 8-(2-octyl-1-cyclopropenyl)octanoic, 7-(2-octyl-1-cyclopropenyl)heptanoic, 9,10-epoxyoctadecanoic, 9,10-epoxy12-octadecenoic, 12,13-epoxy-9-octadecenoic, 14,15-epoxy-11-eicosenoic, 11-(2-cyclopenten-1-yl)undecanoic, 13-(2-cyclopenten-1-yl)tridecanoic, 13-(2-cyclopentenyl)-6-tridecenoic, 11-cyclohexylundecanoic, 13-cyclohexyltridecanoic, 7-(3,4-dimethyl-5-pentylfuran-2-yl)heptanoic, 9-(4-methyl-5-pentylfuran-2-yl)nonanoic, 4-[5]-ladderanebutanoic, 6-[5]-ladderane-hexanoic, or 6-[3]-ladderanehexanoic acid.

Suitable aryl carboxylic acids for use in the present technology to conjugate methylphenidate, derivatives thereof or combinations thereof include, for example, compounds that contain at least one carboxyl group attached to an aromatic ring. Suitable aryl carboxylic acids of the present technology can include, but are not limited to, for example:

(a) aryl carboxylic acids wherein the carboxylic acid group is directly attached to the aryl moiety, which include, but are not limited to, benzoates or heteroaryl carboxylic acids;

(b) aryl carboxylic acids wherein the carboxylic acid group is separated by one carbon from the aryl moiety, which include, but are not limited to, branched phenylpropionic acids, or other derivatives of phenylacetate; or (c) aryl carboxylic acids wherein the carboxylic acid group is separated by two carbons from the aryl moiety, which include, but are not limited to, benzylacetates, substituted derivatives thereof or analogs of cinnamic acid.

Some embodiments of the present technology provide aryl carboxylic acids of category (a), (b), or (c) conjugated to methylphenidate, derivatives thereof, or combinations thereof. Some embodiments of the present technology provide aryl carboxylic acids of category (a) conjugated to methylphenidate, derivatives thereof or combinations thereof, wherein the aryl carboxylic acid of category (a) is benzoates, heteroaryl carboxylic acids or derivatives thereof.

Benzoates

Some embodiments of the present technology provide at least one conjugate of methylphenidate, derivatives thereof or combinations thereof, and at least one benzoate. Suitable common benzoates include, but are not limited to, for example, benzoic acid, or hydroxybenzoates (e.g., salicylic acid analogs). The general structure of benzoates for use in the present technology is shown in formula (X):

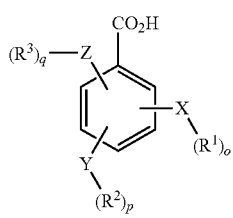

(X)

wherein X, Y and Z can be independently selected from a representative group including H, O, S or —$(CH_2)_x$—; $R^1$, $R^2$ and $R^3$ can be, for example, independently selected from any of the following: H, alkyl, alkoxy, aryl, substituted aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; and x is an integer between 1 and 10.

Benzoates are common in nature and can be found either in their free form, as a salt, or as esters and amides. Numerous benzoic acid analogs are also used in the food and drug industry. Some of the more abundant benzoates are derivatives with hydroxyl groups. The hydroxyl function may be present in its free form or capped with another chemical moiety, preferably, but not limited to, methyl or acetyl groups. The phenyl ring may have additional substituents.

Suitable benzoates include, but are not limited to, for example, benzoic acid, or hydroxybenzoates (e.g., salicylic acid analogs). Suitable examples of hydroxybenzoates for use in the present technology include, but are not limited to, for example, benzoic acid, salicylic acid, acetylsalicylic acid (aspirin), 3-hydroxybenzoic acid, 4-hydroxybenzoic acid, 6-methylsalicylic acid, o,m,p-cresotinic acid, anacardic acids, 4,5-dimethylsalicylic acid, o,m,p-thymotic acid, diflunisal, o,m,p-anisic acid, 2,3-dihydroxybenzoic acid (2,3-DHB), α,β,γ-resorcylic acid, protocatechuic acid, gentisic acid, piperonylic acid, 3-methoxysalicylic acid, 4-methoxysalicylic acid, 5-methoxysalicylic acid, 6-methoxysalicylic acid, 3-hydroxy-2-methoxybenzoic acid, 4-hydroxy-2-methoxybenzoic acid, 5-hydroxy-2-methoxybenzoic acid, vanillic acid, isovanillic acid, 5-hydroxy-3-methoxybenzoic acid, 2,3-dimethoxybenzoic acid, 2,4-dimethoxybenzoic acid, 2,5-dimethoxybenzoic acid, 2,6-dimethoxybenzoic acid, veratric acid (3,4-dimethoxybenzoic acid), 3,5-dimethoxybenzoic acid, gallic acid, 2,3,4-trihydroxybenzoic acid, 2,3,6-trihydroxybenzoic acid, 2,4,5-trihydroxybenzoic acid, 3-O-methylgallic acid (3-OMGA), 4-O-methylgallic acid (4-OMGA), 3,4-O-dimethylgallic acid, syringic acid, or 3,4,5-trimethoxybenzoic acid. Some structures of suitable hydroxybenzoates for use in the practice of the present technology can be found in FIG. 1.

Heteroaryl Carboxylic Acids

In other embodiments, the present technology provides prodrug compositions comprising at least one conjugate of methylphenidate, derivatives thereof or combinations thereof, and one or more aryl or heteroaryl carboxylic acids. Suitably, the heteroatom of common natural products and metabolites is nitrogen. The general structures of heteroaryl carboxylic acids and derivatives thereof are illustrated in formulas (XI), (XII) and (XIII):

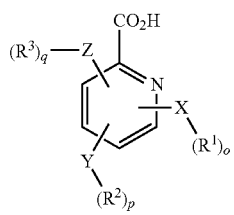

(XI)

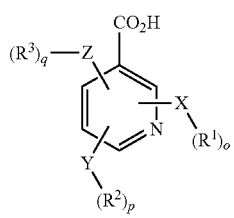

(XII)

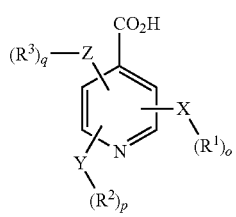

(XIII)

wherein X, Y and Z can be independently selected from the representative group including H, O, S or —$(CH_2)_x$—; $R^1$, $R^2$ and $R^3$ can be independently selected from any of the following: H, alkyl, alkoxy, aryl, substituted aryl, alkenyl, alkynyl, halo, haloalkyl, alkylaryl, arylalkyl, heterocycle, arylalkoxy, cycloalkyl, cycloalkenyl or cycloalkynyl; o, p, q can be independently selected from 0 or 1; and x is an integer between 1 and 10.

Nitrogen heterocyclic compounds are commonly found in nature and are involved in several biological functions in plants and animals. Suitable examples of heteroaryl carboxylic acids for use in the practice of the present technology include, but are not limited to, for example, pyridine derivatives, some of which play an important role in the nicotinate and tryptophan metabolism. In these compounds, one carbon of the phenyl ring is replaced by a nitrogen atom. Besides the carboxyl group, this set of compounds can have additional substituents, preferably but not limited to, hydroxyl groups.

Figure 2:
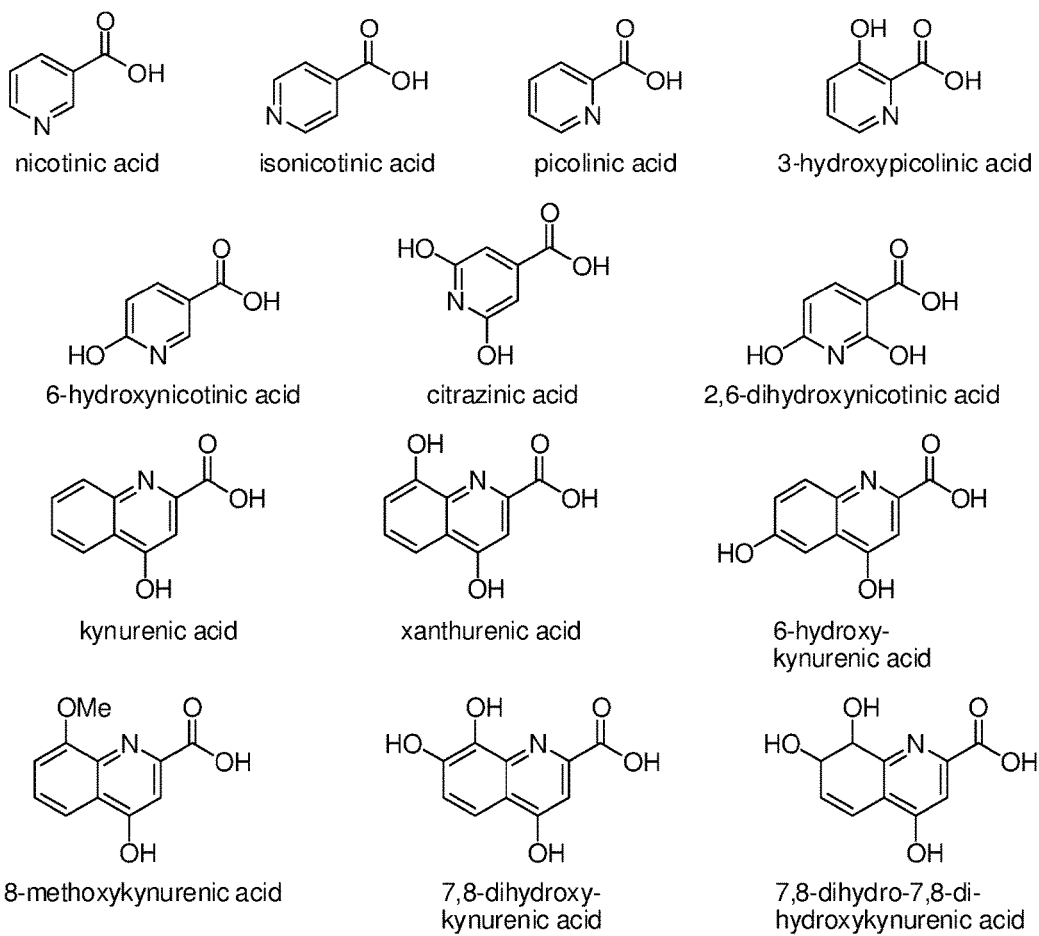
FIG. 2. Chemical structures of some heteroaryl carboxylic acids for use in the making of the conjugates of the present technology.

Suitable examples of heteroaryl carboxylic acids for use in the present technology include, but are not limited to, nicotinic acid (niacin), isonicotinic acid, picolinic acid, 3-hydroxypicolinic acid, 6-hydroxynicotinic acid, citrazinic acid, 2,6-dihydroxynicotinic acid, kynurenic acid, xanthurenic acid, 6-hydroxykynurenic acid, 8-methoxykynurenic acid, 7,8-dihydroxykynurenic acid, or 7,8-dihydro-7,8-dihydroxykynurenic acid. Some structures of suitable heteroaryl carboxylic acids for use in the practice of the present technology can be found in FIG. 2.

Aryl Carboxylic Acids

Some embodiments of the present technology provide aryl carboxylic acids of category (b) conjugated to methylphenidate, derivatives thereof or combinations thereof, where suitable carboxylic acids with a carboxyl group separated by one carbon from the aryl moiety include, but are not limited to, for example, branched phenylpropionic acids (i.e., 2-methyl-2-phenylacetates) or other derivatives of phenylacetate, for example, compounds having the general formula as described in formula (XIV) below. In some embodiments, the carboxylic acid is a phenylacetate, a branched phenylpropionate, an unbranched phenylpropionate (benxylacetate), a phenyl propenoate (cinnamate), salts thereof, derivatives thereof, or combinations thereof. Suitable examples of these compounds, include, but are not limited to, certain types of NSAIDs (Non-Steroidal Anti-Inflammatory Drugs), such as profens, or tyrosine metabolites (such as p-hydroxyphenyl pyruvate), among others. The general structure of phenylpropionic acids or other derivatives of phenylacetate of the present technology is shown in formula (XIV):

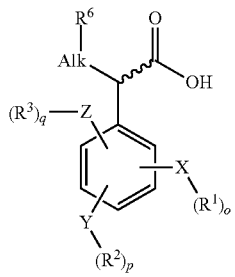

(XIV)

wherein X, Y and Z can be independently selected from the representative group including H, O, S or —(CH$_2$)$_x$—; R$^1$, R$^2$ and R$^3$ can be independently selected from any of the following: H, alkyl, alkoxy, aryl, substituted aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; Alk is an alkyl chain —(CH$_2$)$_n$— with n being either 0 or 1; x is an integer between 1 and 10; and R$^6$ is selected from H, OH or carbonyl.

Phenylacetates

Figure 3:
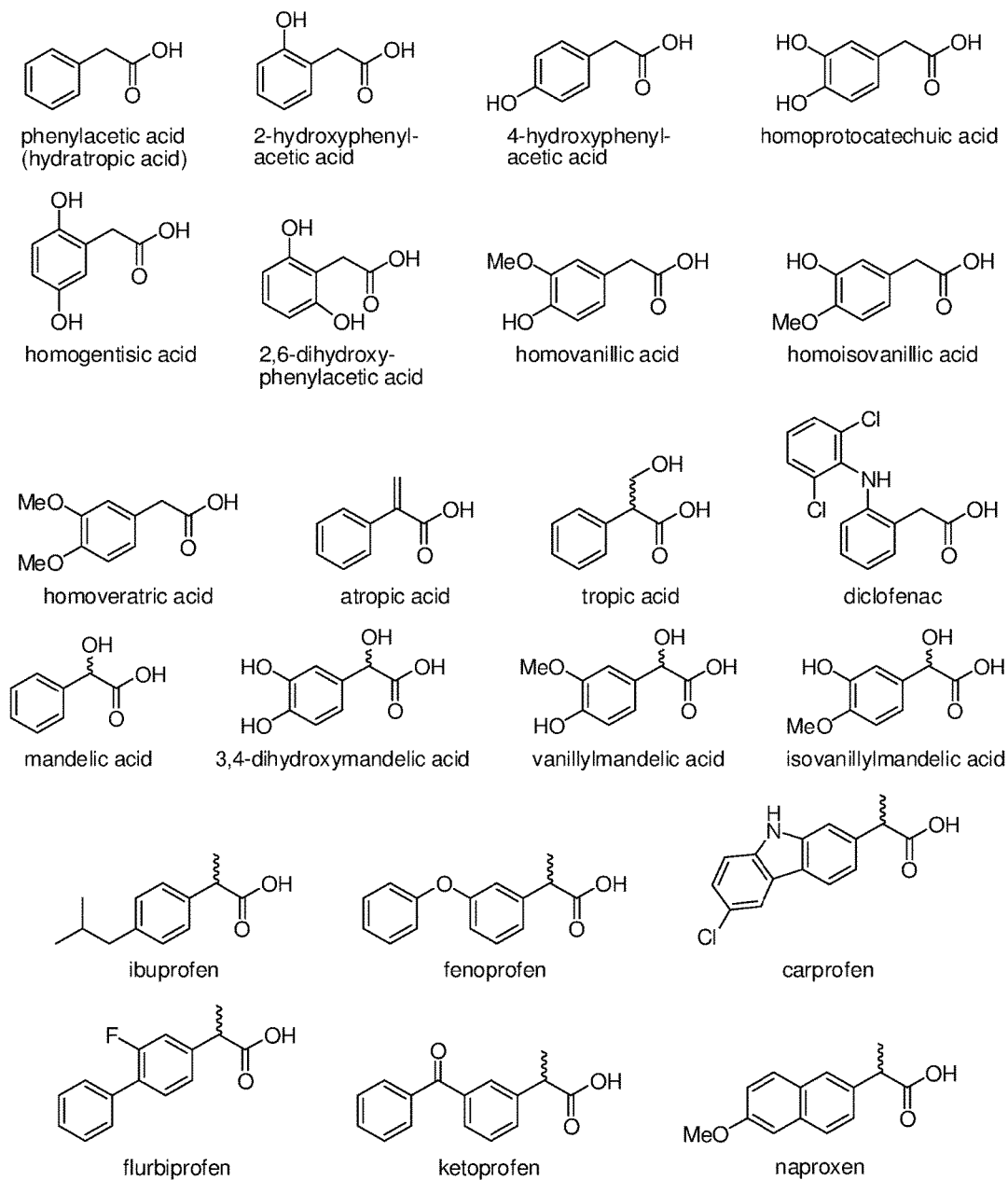
FIG. 3. Chemical structures of some phenylacetates for use in the making of the conjugates of the present technology.

Phenylacetic acids encompass various subsets of natural products, metabolites and pharmaceuticals. One such pharmaceutical subset are "profens", a type of NSAID and derivatives of certain phenylpropionic acids (i.e., 2-methyl-2-phenylacetic acid analogs). Some other phenylacetates have central functions in the phenylalanine and tyrosine metabolism. Suitable phenylacetates of the present technology include, but are not limited to, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, d,l-tropic acid, diclofenac, d,l-mandelic acid, 3,4-dihydroxy-d,l-mandelic acid, vanillyl-d,l-mandelic acid, isovanillyl-d,l-mandelic acid, ibuprofen, fenoprofen, carprofen, flurbiprofen, ketoprofen, or naproxen. Some structures of suitable phenylacetates for use in the practice of the present technology can be found in FIG. 3.

Benzylacetates and Cinnamates

In some embodiments of the present technology, aryl carboxylic acids of category (c) are conjugated to methylphenidate, derivatives thereof or combinations thereof, wherein the aryl carboxylic acids of category (c) include, but are not limited to, for example, benzylacetates, substituted derivatives thereof or analogs of cinnamic acid, for example compounds with the general formulas (XV) and (XVI) below:

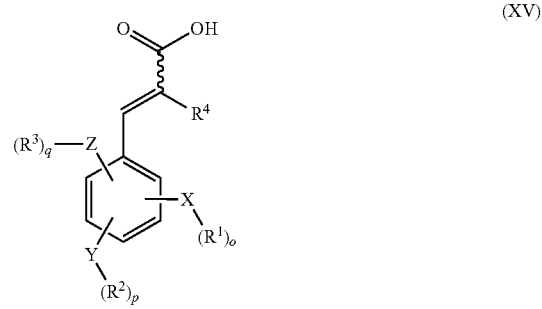

(XV)

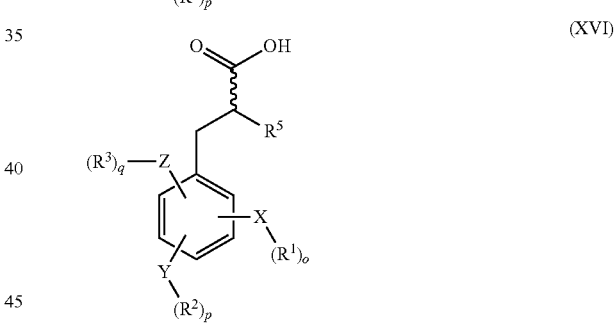

(XVI)

wherein X, Y and Z can be independently selected from a representative group including H, O, S or —(CH$_2$)$_x$—; R$^1$, R$^2$ and R$^3$ can be independently selected from any of the following: H, alkyl, alkoxy, aryl, substituted aryl, alkenyl, alkynyl, halo, haloalkyl, alkylaryl, arylalkyl, heterocycle, arylalkoxy, cycloalkyl, cycloalkenyl or cycloalkynyl; o, p, q can be independently either 0 or 1; x is an integer from 1 to 10; R$^4$ is H or OH; and R$^5$ is H, OH or carbonyl. Both classes of compounds are abundant in nature in the form of natural products or metabolites (e.g., phenylalanine metabolism). The carboxyl group can be attached directly to the aromatic ring or be separated by an alkyl or alkenyl chain. The chain length of the alkyl or alkenyl group for use in this technology should not preferably exceed two unbranched carbons, but is not limited in numbers of atoms on potential side-chains or additional functional groups.

The present technology also includes both carbon only aryl and aryl groups with heteroatoms (heteroaryl). The aryl or heteroaryl group which is connected directly or through an alkyl or alkenyl chain to the carboxyl function, should preferably be a 6-membered ring and should preferably contain no or one heteroatom. It should be appreciated by those skilled in the art additional substituted or unsubstituted aromatic or aliphatic rings may be fused to such a 6-membered aryl or heteroaryl moiety.

Figure 4:
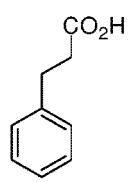
FIG. 4. Chemical structures of some benzylacetates for use in the making of the conjugates of the present technology.
Figure 4:
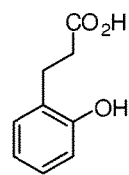
Figure 4:
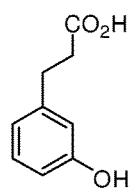
Figure 4:
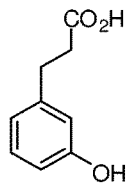
Figure 4:
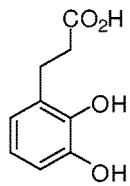
Figure 4:
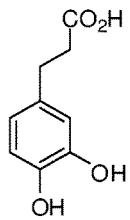
Figure 4:
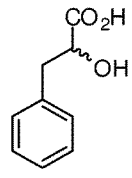

Benzylacetates are defined by an ethylene group between the carboxyl function and the phenyl ring. Both the alkyl chain and the aryl moiety can have, for example, substituents, preferably hydroxyl groups. Some compounds of this class can be found in the phenylalanine metabolism. Suitable examples of benzylacetates for use in the practice of the present technology include but are not limited to, for example, benzylacetic acid, melilotic acid, 3-hydroxyphenylpropanoic acid, 4-hydroxyphenylpropanoic acid, 2,3-dihydroxyphenylpropanoic acid, d,l-phenyllactic acid, o,m,p-hydroxy-d,l-phenyllactic acid, or phenylpyruvic acid. Some structures of suitable benzylacetates for use in the practice of the present technology can be found in FIG. 4.

Figure 5:
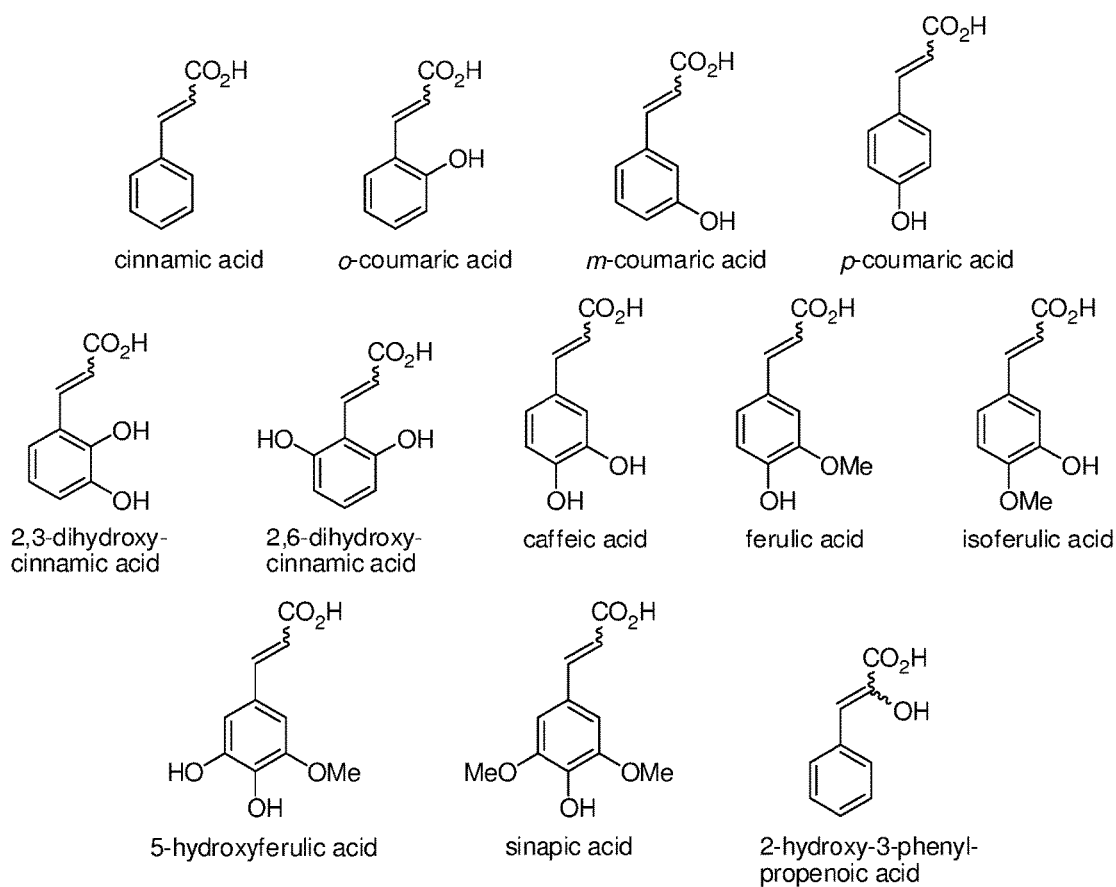
FIG. 5. Chemical structures of some cinnamates for use in the making of the conjugates of the present technology.

Cinnamic acids (3-phenylacrylic acids) are unsaturated analogs of benzylacetic acids, which are found ubiquitously in plants and fruits. Cinnamates occur in two isomeric forms: cis (Z) and trans (E). Use of cinnamates in the present technology can be either isomer form, but are preferably in the trans configuration. Similar to benzylacetates, derivatives of cinnamic acid can be substituted on the alkenyl or aryl moiety of the molecule. Preferred substituents are hydroxyl and methoxy groups. Certain cinnamates play a key role in the phenylalanine metabolism. Some suitable cinnamates for use in the present technology include, but are not limited to, for example, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, or 2-hydroxy-3-phenylpropenoic acid. Structures of suitable cinnamates for use in the practice of the present technology can be found in FIG. 5.

Dicarboxylic and Tricarboxylic Acids

Figure 6:
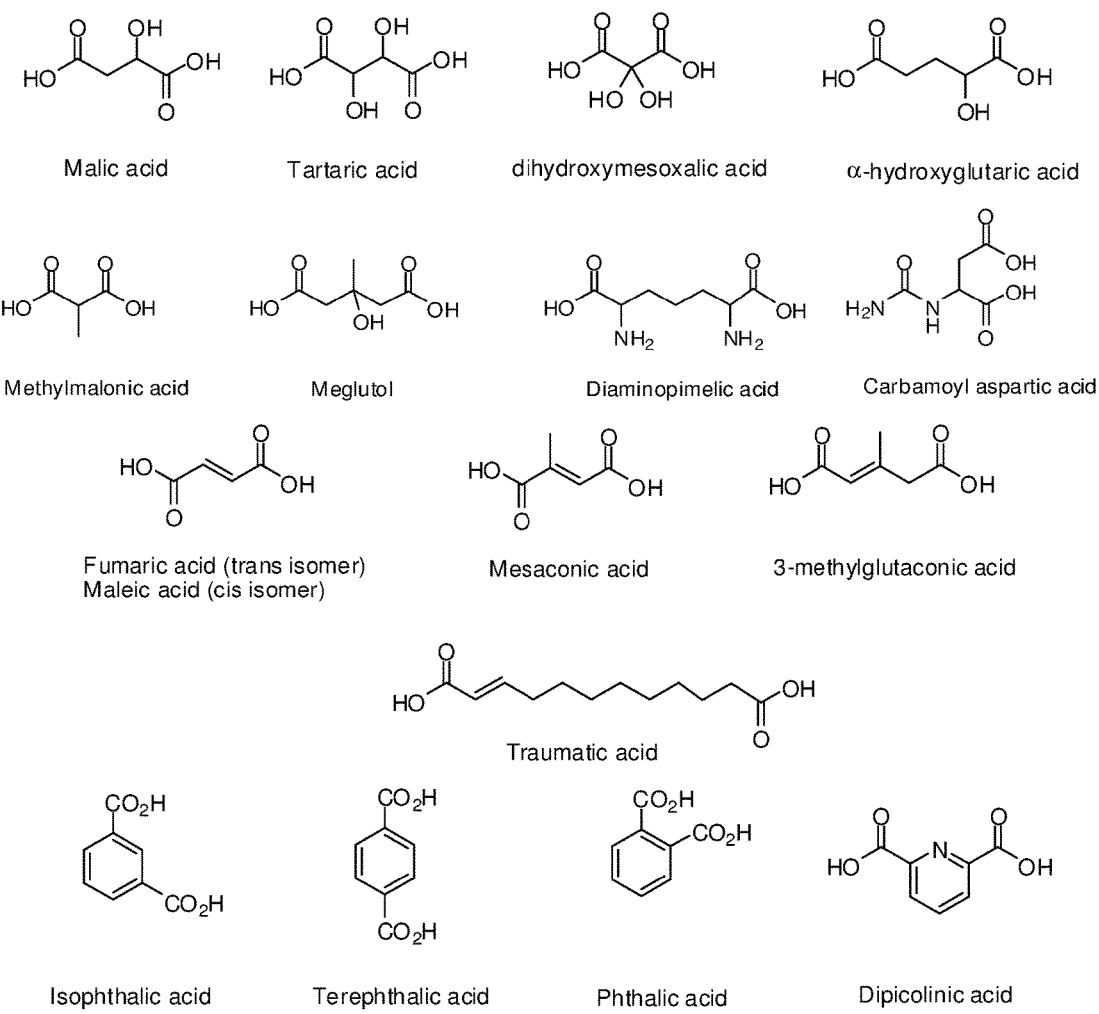
FIG. 6. Chemical structures of some dicarboxylic acids for use in the making of the conjugates of the present technology.
Figure 7:
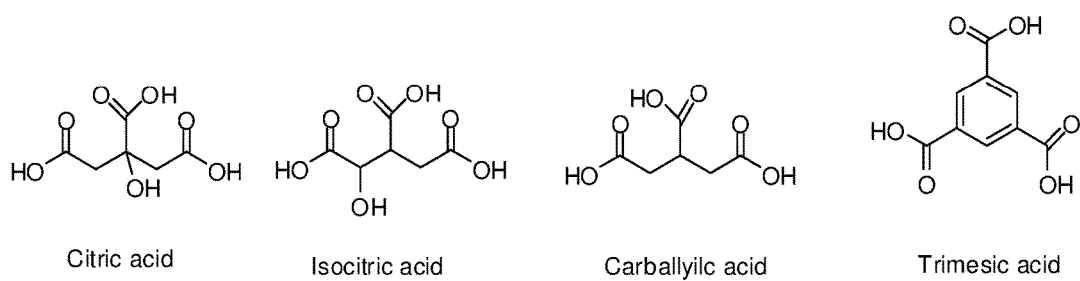
FIG. 7. Chemical structures of some tricarboxylic acids for use in the making of the conjugates of the present technology.

In some embodiments, the methylphenidate, derivatives thereof or combinations thereof, can be conjugated to one or more dicarboxylic or tricarboxylic acids. Dicarboxylic acids are compounds with two carboxyl groups with a general formula of HOOC—R—COOH, where R can be an alkyl, alkenyl, alkynyl or aryl group, or derivatives thereof. Dicarboxylic acids can have straight carbon chains or branched carbon chains. The carbon chain length may be short or long. Polycarboxylic acids are carboxylic acids with three or more carboxyl groups. Suitable examples of dicarboxylic and tricarboxylic acids for the practice of the present technology include, but are not limited to, for example, oxalic, malonic, succinic, glutaric, adipic, pimelic, suberic, azelaic, sebacic, brassylic, thapsic, malic, tartaric, dihydroxymesoxalic, α-hyroxyglutaric, methylmalonic, meglutol, diaminopimelic, carbamoyl aspartic, fumaric, maleic, mesaconic, 3-methylglutaconic, traumatic, phthalic acid, isophthalic, terephthalic, dipicolinic, citric acid, isocitric, carballylic, or trimesic acid. Some structures of suitable dicarboxylic acids for use in the practice of the present technology can be found in FIG. 6 and some structures of suitable tricarboxylic acids for use in the practice of the present technology can be found in FIG. 7.

Inorganic Oxoacids

Figure 8:
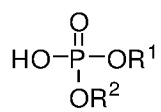
FIG. 8. Chemical structures of some inorganic oxoacids for use in the making of the conjugates of the present technology.
Figure 8:
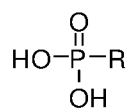
Figure 8:
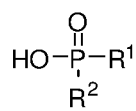
Figure 8:
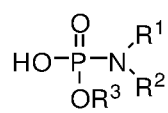
Figure 8:
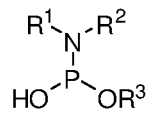
Figure 8:
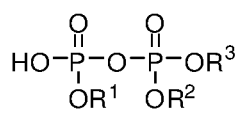
Figure 8:
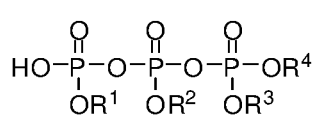
Figure 8:
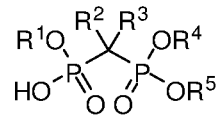
Figure 8:
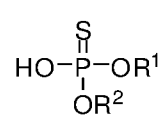
Figure 8:
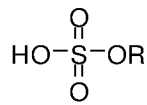
Figure 8:
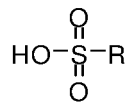
Figure 8:
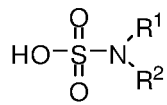
Figure 8:
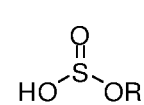
Figure 8:
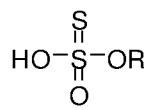
Figure 8:
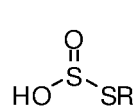
Figure 8:
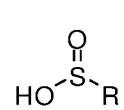
Figure 8:
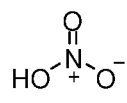
Figure 8:
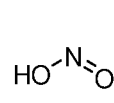
Figure 8:
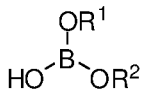
Figure 8:
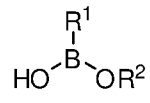
Figure 8:
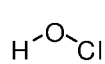
Figure 8:
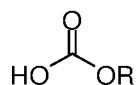
Figure 8:
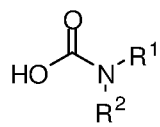
Figure 9:
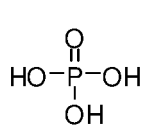
FIG. 9. Chemical structures of some inorganic oxoacid derivatives for use in the making of the conjugates of the present technology.
Figure 9:
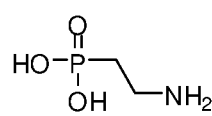
Figure 9:
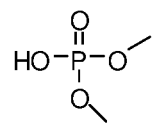
Figure 9:
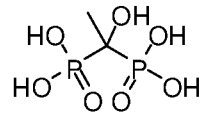
Figure 9:
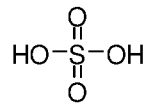
Figure 9:
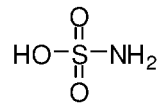
Figure 9:
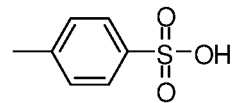

In some embodiments of the present technology, at least one methylphenidate, derivatives thereof or combinations thereof, is conjugated to at least one inorganic oxoacid or an organic or inorganic derivative thereof. Inorganic oxoacids of the present technology contain a —OH group (e.g., phosphoric acid) or they can be organic or inorganic derivatives of the same (e.g., phosphonates, diphosphates). Some suitable examples of inorganic oxoacids and their derivates include, but are not limited to, phosphates, phosphonates, phosphinates, phosphoramidates, phosphoramidites, diphosphates, triphosphates, biphosphonates, phosphorothioates, phosphorodithioates, phosphites, sulfates, sulfonates, sulfamates, sulfites, thiosulfates, thiosulfites, sulfinates, nitrate, nitrite, borates, boronates, hypochlorite, carbonates, or carbamates. General structures of some inorganic oxoacids for use in the practice of the present technology can be found in FIG. 8 and structures of some organic or inorganic derivatives of inorganic oxoacids for use in the practice of the present technology can be found in FIG. 9.

Preferred embodiments of the present technology include one or more inorganic oxoacids that are phosphate esters. More preferred embodiments include inorganic oxoacids that are phosphate monoesters, even more preferably phosphoric acid.

Additional preferred oxoacids of the present technology include fatty acids, hydroxy carboxylic acids, amino acids, optionally esterified phosphoric acids and optionally esterified dicarboxylic acids. More preferred oxoacids of the present technology are $C_{2-24}$ carboxylic acids, aryl carboxylic acids, aminocaproic acid, phosphoric acid, standard amino acids and non-standard amino acids.

Amino Acids

Amino acids are one of the most important building blocks of life. They constitute the structural subunit of proteins, peptides, and many secondary metabolites. In addition to the 22 standard (proteinogenic) amino acids that make up the backbone of proteins, there are hundreds of other natural (non-standard) amino acids that have been discovered either in free form or as components in natural products. The amino acids used in some embodiments of the prodrugs of this invention include natural amino acids, synthetic (non-natural, unnatural) amino acids, and their derivatives.

Standard Amino Acids

There are currently 22 known standard or proteinogenic amino acids that make up the monomeric units of proteins and are encoded in the genetic code. The standard amino acids include alanine, arginine, asparagine, aspartic acid, cysteine, glutamic acid, glutamine, glycine, histidine, isoleucine, leucine, lysine, methionine, phenylalanine, proline, pyrrolysine, selenocysteine, serine, threonine, tryptophan, tyrosine and valine. These standard amino acids have the general structure shown in FIG. 10, where R represents the side chain on the α-carbon.

Non-Standard Amino Acids

Figure 11:
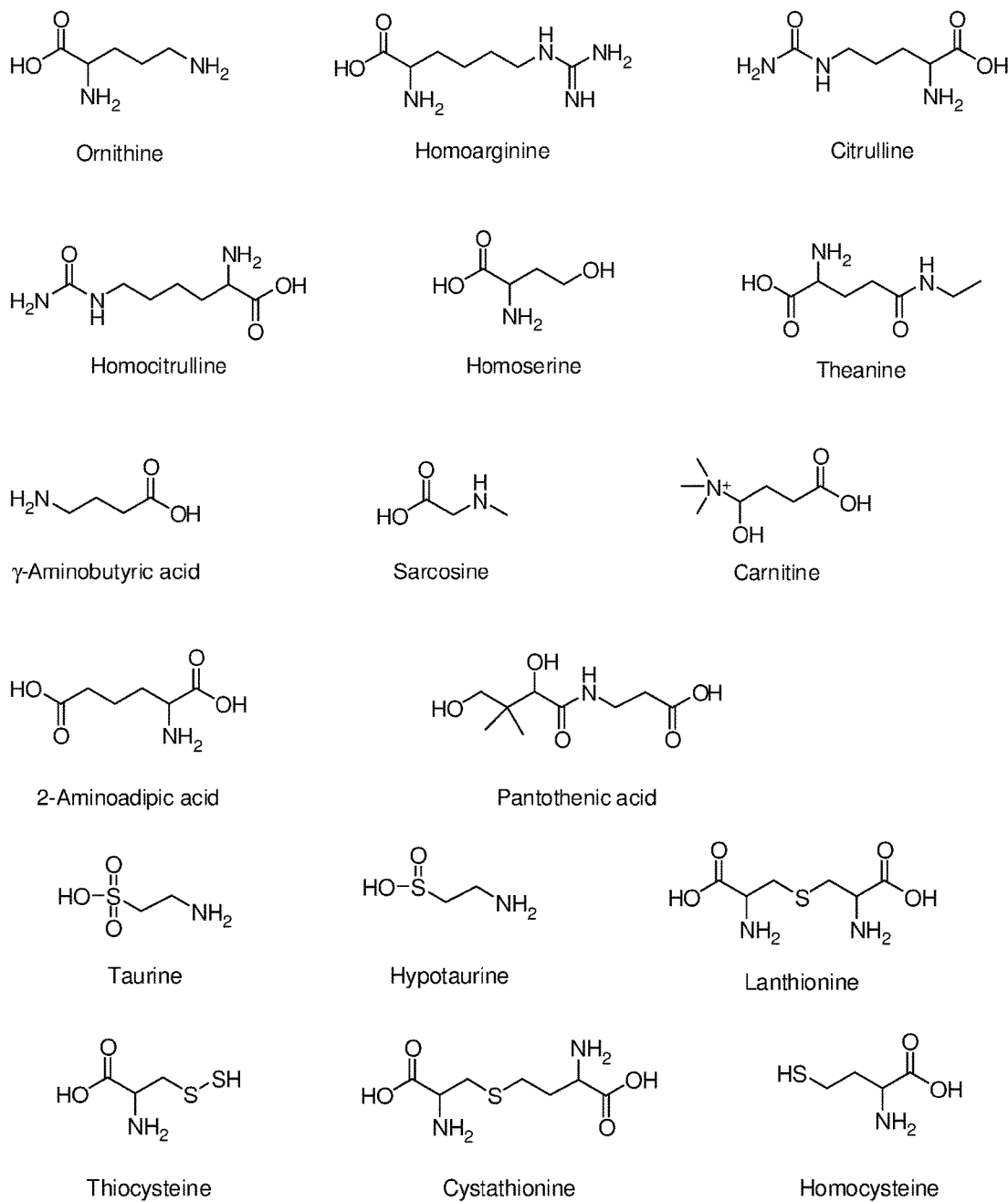
FIG. 11. Chemical structures of some non-standard amino acids for use in the making of the conjugates of the present technology.
Figure 11:
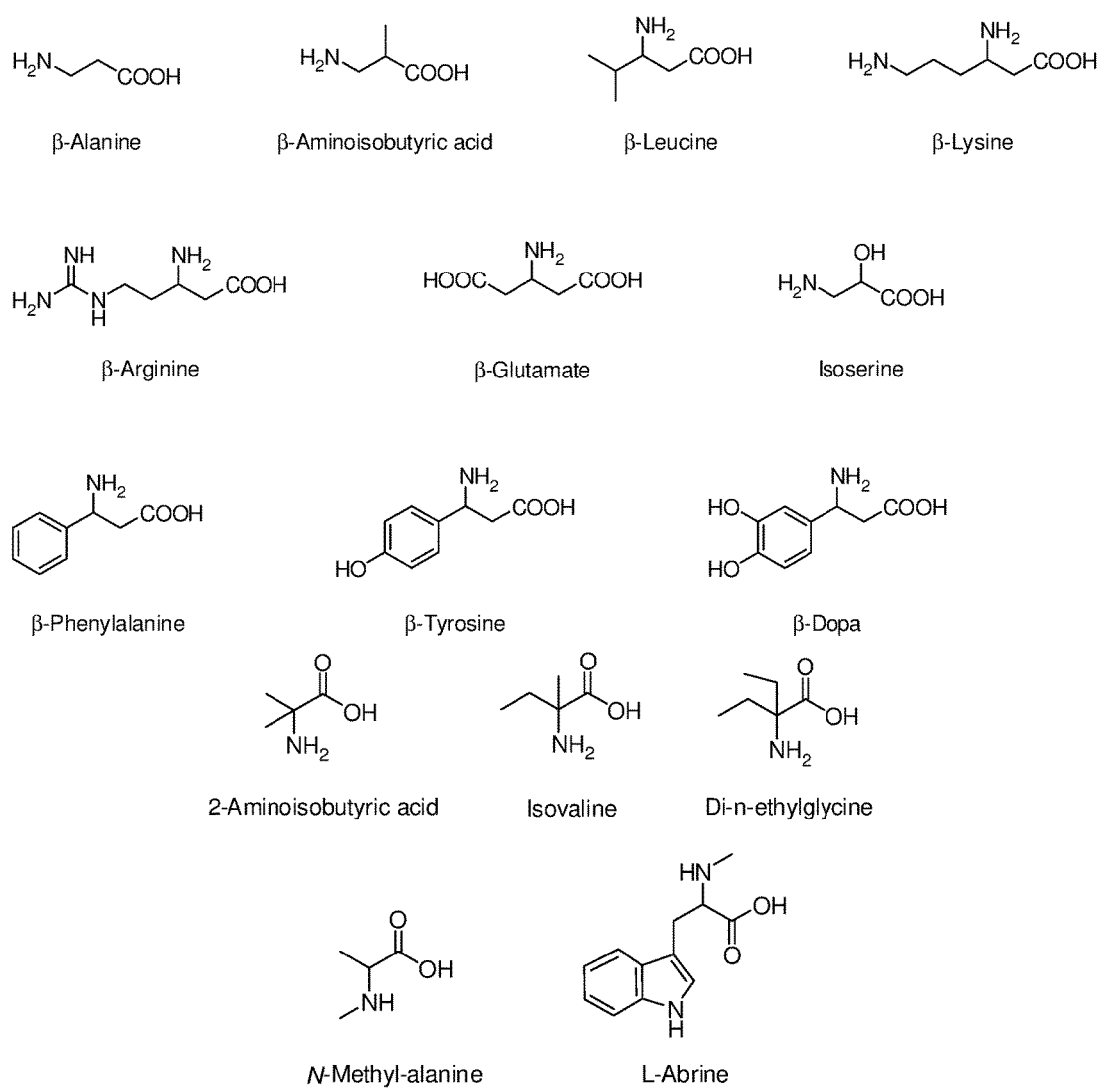
Figure 11:
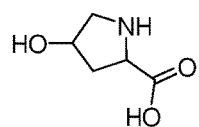
Figure 11:
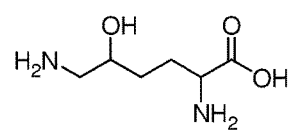
Figure 11:
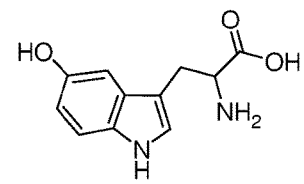
Figure 11:
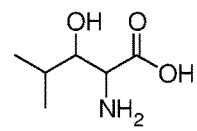
Figure 11:
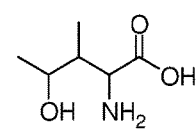
Figure 11:
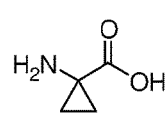
Figure 11:
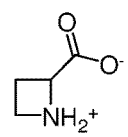
Figure 11:
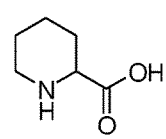

Non-standard amino acids can be found in proteins created by chemical modifications of standard amino acids already incorporated in the proteins. This group also includes amino acids that are not found in proteins but are still present in living organisms either in their free form or bound to other molecular entities. Non-standard amino acids occur mostly as intermediates in metabolic pathways of standard amino acids and are not encoded by the genetic code. Examples of non-standard amino acids include but are not limited to ornithine, homoarginine, citrulline, homocitrulline, homoserine, theanine, γ-aminobutyric acid, 6-aminohexanoic acid, sarcosine, cartinine, 2-aminoadipic acid, pantothenic acid, taurine, hypotaurine, lanthionine, thiocysteine, cystathionine, homocysteine, β-amino acids such as β-alanine, β-aminoisobutyric acid, β-leucine, β-lysine, β-arginine, β-tyrosine, β-phenylalanine, isoserine, β-glutamic acid, β-tyrosine, β-dopa (3,4-dihydroxy-L-phenylalanine), α,α-disubstituted amino acids such as 2-aminoisobutyric acid, isovaline, di-n-ethylglycine, N-methyl acids such as N-methyl-alanine, L-abrine, hydroxy-amino acids such as 4-hydroxyproline, 5-hydroxylysine, 3-hydroxyleucine, 4-hydroxyisoleucine, 5-hydroxy-L-tryptophan, cyclic amino acids such as 1-aminocyclopropyl-1-carboxylic acid, azetidine-2-carboxylic acid and pipecolic acid. Some structures of suitable non-standard amino acids that can be used in some embodiments of the prodrugs of this invention are shown in FIG. 11.

Synthetic Amino Acids

Figure 12:
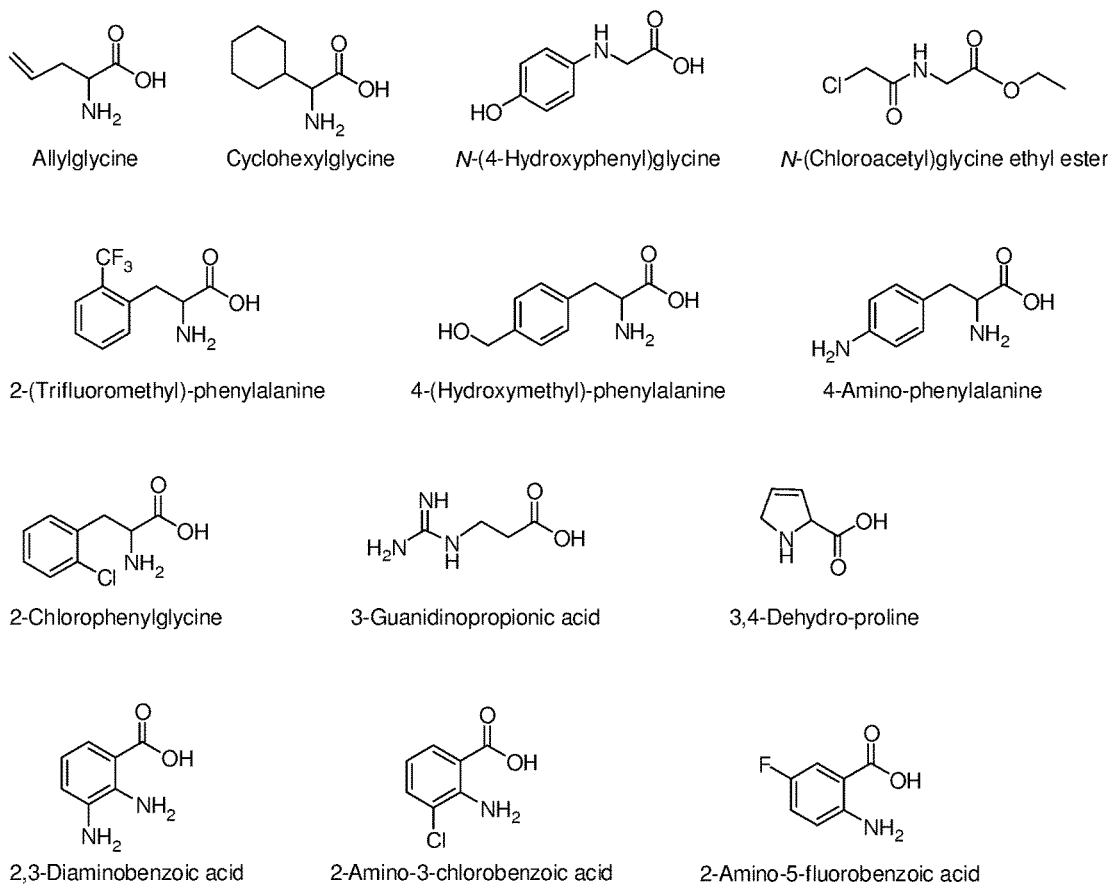
FIG. 12. Chemical structures of some synthetic amino acids for use in the making of the conjugates of the present technology.
Figure 12:
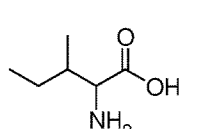
Figure 12:
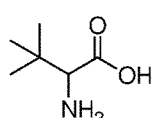
Figure 12:
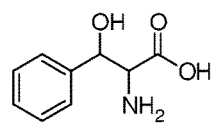
Figure 12:
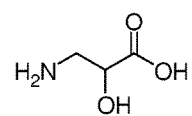
Figure 12:
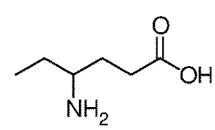
Figure 12:
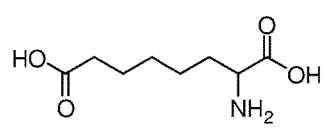
Figure 12:
Figure 12:
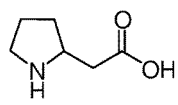
Figure 12:
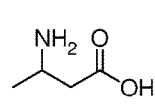
Figure 12:
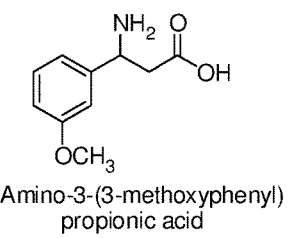
Figure 12:
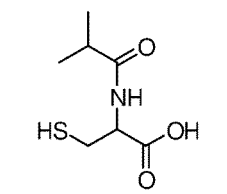
Figure 12:
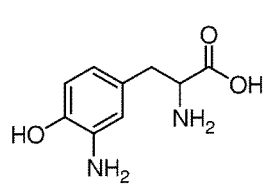
Figure 12:
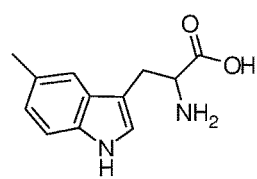
Figure 12:
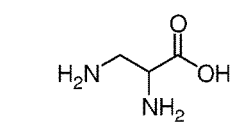
Figure 12:
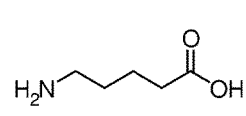
Figure 12:
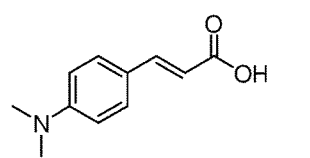

Synthetic amino acids do not occur in nature and are prepared synthetically. Examples include but are not limited to allylglycine, cyclohexylglycine, N-(4-hydroxyphenyl)glycine, N-(chloroacetyl)glycline ester, 2-(trifluoromethyl)-phenylalanine, 4-(hydroxymethyl)-phenylalanine, 4-amino-phenylalanine, 2-chlorophenylglycine, 3-guanidino propionic acid, 3,4-dehydro-proline, 2,3-diaminobenzoic acid, 2-amino-3-chlorobenzoic acid, 2-amino-5-fluorobenzoic acid, allo-isoleucine, tert-leucine, 3-phenylserine, iso-serine, 3-aminopentanoic acid, 2-amino-octanedioic acid, 4-chloro-β-phenylalanine, β-homoproline, β-homoalanine, 3-amino-3-(3-methoxyphenyl)propionic acid, N-isobutyryl-cysteine, 3-amino-tyrosine, 5-methyl-tryptophan, 2,3-di-aminopropionic acid, 5-aminovaleric acid, and 4-(dimethylamino)cinnamic acid. Some structures of suitable synthetic amino acids that can be used in some embodiments of the prodrugs of this invention are shown in FIG. 12.

Linkers

In some embodiments of the present technology, the methylphenidate, derivatives thereof or combinations thereof, is conjugated to one or more organic or inorganic oxoacids via one or more linkers. Linker moieties of the present technology, which connect the one or more organic or inorganic oxoacids to the methylphenidate, derivatives thereof or combinations thereof, are preferably at least one (acyloxy)alkyloxy group or a derivative thereof with the general formula:

wherein X is selected from a representative group including optionally substituted alkyl, optionally substituted aryl, optionally substituted alkylaryl, optionally substituted heteroalkyl, optionally substituted heteroaryl, optionally substituted heterocycle, optionally substituted alkenyl, optionally substituted alkynyl, optionally substituted cycloalkyl, optionally substituted cycloalkenyl, optionally substituted cycloalkynyl, or optionally substituted alkoxy substituents.

Preferred embodiments of the present technology include linkers where X is at least one aliphatic group. More preferred embodiments include linkers where X is at least one alkyl group. Even more preferred embodiments are (acyloxy)methyloxy, (acyloxy)ethyloxy, or (acyloxy)methyl (methyl)oxy linkers.

Administration, Formulation and Advantages

The prodrugs or conjugate compositions of the present technology can be administered orally and, upon administration, release the active methylphenidate, derivatives thereof or combinations thereof, after being hydrolyzed in the body. Not wishing to be bound by any particular theory, the oxoacids that are conjugated to the methylphenidate, derivatives thereof or combinations thereof, of the present technology are naturally occurring metabolites, pharmaceutically active compounds or mimetics thereof or derivatives thereof. It is believed that the prodrugs or conjugates of the present technology can be easily recognized by physiological systems resulting in hydrolysis and release of methylphenidate.

The prodrugs of the present technology are believed to have no or limited pharmacological activity themselves and consequently may follow a metabolic pathway that differs from the parent drug (i.e., methylphenidate). Without being bound by any theory, it is believed that by choosing suitable linkers and oxoacids ("ligands"), the release of methylphenidate into the systemic circulation can be controlled even when the prodrug is administered via routes other than oral administration.

In one embodiment, the at least one conjugated methylphenidate, derivatives thereof or combinations thereof, of the present technology are believed to surprisingly release methylphenidate, derivatives thereof or combinations thereof, similar to free or unmodified methylphenidate. In another alternative embodiment, the at least one conjugated methylphenidate, derivatives thereof or combinations thereof, of the present technology are believed to surprisingly be released in a controlled or sustained form.

It has been surprisingly found that in some embodiments of the present technology, the prodrugs or conjugates of the present application provide an increased bioavailability as compared with unconjugated methylphenidate. In some embodiments, the prodrugs or conjugates of the present technology surprisingly provide increased water solubility as compared with unconjugated methylphenidate. In some embodiments, the prodrugs or compositions of the present technology have at least about 1.2× or at least about 1.5× the water solubility of unconjugated methylphenidate. In some embodiments, the prodrugs or compositions of the present technology have at least about 1.7×, at least about 2.0×, at least about 2.2×, at least about 2.5×, at least about 3.0×, at least about 4.0× or at least about 5× the water solubility of unconjugated methylphenidate, and include any multiples in between or above that have water solubility greater than unconjugated methylphenidate. Not to be bound by any particular theory, the increase in water solubility may allow for the conjugate to be formed into certain dosage forms at higher concentrations, dosage strengths or higher dose loading capacities than unconjugated methylphenidate. In some embodiments, these dosage forms include, but are not limited to, forms that require water solubility, including, but not limited to, liquids and oral thin films or strips.

In a further embodiment, the at least one prodrug or conjugate of the present technology is believed to unexpectedly have increased absorption over unmodified methylphenidate. In yet another embodiment, the at least one prodrug or conjugate of the present technology is believed to unexpectedly have increased bioavailability over unconjugated methylphenidate. In some embodiments, the conjugate is capable of being enzymatically or hydrolytically activated or converted into the active form. In one embodiment, the composition or prodrug described herein would release methylphenidate, its active metabolites and/or derivates and their combination resulting in increased peak plasma concentrations and/or exposure to methylphenidate, its active metabolites and/or derivatives and their combination when compared to free or unconjugated methylphenidate at equimolar doses. Not to be bound by any particular theory, it is believed that this may allow for administration of a lower dose with equal or improved therapeutic effect, but with fewer and/or less severe side effects when compared to unmodified methylphenidate, thereby improving the safety profile of the drug. Common side effects of methylphenidate are nervousness, agitation, anxiety, and insomnia or drowsiness. Other common side effects are abdominal pain, weight loss, hypersensitivity, nausea, dizziness, palpitation, headache, dyskinesia, blood pressure, pulse changes, tachycardia, angina, and cardiac arrhythmia.

In a further embodiment, the increased absorption over unmodified methylphenidate, or improved water solubility over free methylphenidate may provide for a better bioavailability of methylphenidate referring to a higher area under the curve (AUC) or having higher circulating plasma concentrations.

In one embodiment, the at least one prodrug or conjugate of the present technology would alter the metabolic profile of methylphenidate, derivatives thereof or combinations thereof, by, for example, changing the amounts and/or ratio of methylphenidate and its metabolites, such as the inactive ritalinic acid within the body. The at least one prodrug or conjugate, for example, would decrease the number and/or amount of metabolites, including active, inactive, toxic or non-toxic metabolites, produced by unmodified methylphenidate. Not wishing to be bound by any particular theory, it is believed that this change in metabolism may potentially alleviate certain side effects and improve upon the safety profile of methylphenidate.

In another embodiment, the prodrugs or conjugates of the present technology would unexpectedly produce reduced interpatient variability of methylphenidate plasma concentrations. Not to be bound by any particular theory, it can be assumed that the reduction of interpatient variability of methylphenidate plasma concentrations may be due to either increased bioavailability or a modified metabolic pathway or a combination of both. In another embodiment, the prodrug of the present technology would alter the metabolic pathway of the released methylphenidate when compared to unmodified methylphenidate. It is believed that this new metabolism may decrease interpatient variability and/or reduce side effects associated with unconjugated methylphenidate or any of its metabolites.

In a further embodiment, the at least one prodrug or conjugate of the present technology can comprise racemic d- and l-methylphenidate which is preferably hydrolyzed to d-methylphenidate in the body and thus delivers more of the therapeutically active d-isomer. Wishing not to be bound by any particular theory, this may reduce potential side effects caused by l-methylphenidate and/or its metabolites.

In another embodiment, the at least one prodrug or conjugate of the present technology is believed to unexpectedly generate a $C_{max}$ value of released methylphenidate, derivatives thereof or combinations thereof, that is higher than the $C_{max}$ value produced by unconjugated methylphenidate, derivatives thereof or combinations thereof, when administered orally at equimolar doses. In a further embodiment, the at least one prodrug or conjugate are believed to surprisingly generate an AUC value of released methylphenidate, derivatives thereof or combinations thereof, that is higher than the AUC value produced by unconjugated methylphenidate when administered orally at equimolar doses. In yet another embodiment, the at least one prodrug or conjugate is believed to surprisingly generate both a $C_{max}$ and an AUC value of released methylphenidate that is higher than the $C_{max}$ and AUC values produced by unconjugated methylphenidate when administered orally at equimolar doses.

In some embodiments, the AUC is about 110% or greater of the AUC of unconjugated methylphenidate, when administered orally at equimolar doses, for example about 110% to about 260%, alternatively from about 120% to about 260%, alternatively from about 110% to about 250%, including, but not limited to, about 110%, about 130%, about 150%, about 170%, about 190%, about 210%, about 230%, about 250% or any amounts in between, in increments of about 0.5%, about 1%, about 2%, about 2.5%, about 5%, about 10%, or about 20%.

In some embodiments, the $C_{max}$ is about 110% or greater of the $C_{max}$ of unconjugated methylphenidate, when administered orally at equimolar doses, for example about 110% to about 260%, alternatively from about 120% to about 260%, alternatively from about 110% to about 250%, including, but not limited to, about 110%, about 130%, about 150%, about 170%, about 190%, about 210%, about 230%, about 250% or any amounts in between, in increments of about about 0.5%, about 1%, about 2%, about 2.5%, about 5%, about 10%, or about 20%.

In another embodiment, the at least one prodrug or conjugate is believed to unexpectedly generate a $T_{max}$ value of released methylphenidate that is longer than the $T_{max}$ value produced by unconjugated methylphenidate when administered at equimolar doses. In another embodiment, the at least one prodrug or conjugate is believed to surprisingly generate a $T_{max}$ value of released methylphenidate that is similar to the $T_{max}$ value produced by unconjugated methylphenidate, when administered at equimolar doses.

In some embodiments, the AUC is about 50% or smaller of the AUC of unconjugated methylphenidate, when administered intranasally or intravenously at equimolar doses, for example about 50% to about 0.1%, alternatively from about 25% to about 0.1%, alternatively from about 50% to about 1%, including, but not limited to, about 50%, about 40%, about 30%, about 20%, about 10%, about 1% or any amounts in between, in increments of about about 0.5%, about 1%, about 2%, about 2.5%, about 5% or about 10%.

Methylphenidate is addictive and prone to substance abuse because of its pharmacological similarity to cocaine and amphetamine. Oral abuse has been reported to lead to hallucinations, paranoia, euphoria, and delusional disorder. Oral abuse may subsequently escalate to intravenous and intranasal abuse. Euphoria has been reported after intravenous administration of methylphenidate. When administered intranasally the effect is found to be similar to intranasal use of amphetamines.

In some alternative embodiments of the present technology, the compounds, prodrugs, compositions and/or methods of the present technology are believed to provide reduced potential for overdose, reduced potential for abuse and/or improve the characteristics of methylphenidate, derivatives thereof or combinations thereof with regard to toxicities or suboptimal release profiles. In some alternative embodiments of the present technology, some compositions of the present technology may preferably have no or a substantially decreased pharmacological activity when administered through injection or intranasal routes of administration. However, they remain orally bioavailable. Without wishing to be limited to the below theory, it is believed that overdose protection may occur due to the conjugates being exposed to different enzymes and/or metabolic pathways after oral administration whereby the conjugate of the present technology is exposed to the gut and first-pass metabolism as opposed to exposure to enzymes in the circulation or mucosal membranes in the nose which limits the ability of the methylphenidate, derivatives thereof or combinations thereof, from being released from the conjugate. Therefore, in some alternative embodiments, abuse resistance is provided by limiting the effectiveness of alternative routes of administration. Again, not wishing to be bound by any particular theory, the bioavailability can be a result of the hydrolysis of the chemical linkage (i.e., a covalent linkage) following oral administration. In at least one alternative embodiment, the prodrugs of the present technology are envisioned to not hydrolyze or to hydrolyze at a reduced rate or to a limited extent via non-oral routes. As a result, they are believed to not generate high plasma or blood concentrations of released methylphenidate when injected or snorted compared to free methylphenidate administered through these routes.

In some alternative embodiments, it is contemplated that at least some compositions of the present technology comprising the prodrugs of one or more methylphenidate, derivatives thereof or combinations thereof, are resistant to abuse by parenteral routes of administration, such as intravenous "shooting," or intranasal "snorting," that are often employed during illicit use. In at least one contemplated alternative embodiment, release of methylphenidate, derivatives thereof or combinations thereof, is reduced when the composition of the present technology is delivered by parenteral routes. In some other contemplated alternative embodiments, the conjugates of the present technology, since they are believed to include covalently bound methylphenidate, derivatives thereof or combinations thereof, are not able to be physically manipulated to release the methylphenidate, derivatives thereof or combinations thereof, from the conjugated methylphenidate, derivatives thereof or combinations thereof, by methods, for example, of grinding up or crushing of solid forms. Further, some alternative conjugates of the present technology are contemplated to exhibit resistance to chemical hydrolysis under conditions a potential drug abuser may apply to "extract" the active portion of the molecule, for example, by boiling, or acidic or basic solution treatment of the conjugate. In some alternative embodiments, some compositions containing prodrugs or conjugates of the present technology preferably have no or a substantially decreased pharmacological activity when administered through injection or intranasal routes of administration. However, they remain orally bioavailable.

For example, in one alternate embodiment, the at least one prodrug or conjugate of the present technology is contemplated to surprisingly maintain its effectiveness and abuse resistance following the crushing of the tablet, capsule or other oral dosage form utilized to deliver the therapeutic component (i.e., active ingredient/drug) which is believed to be due to the inherent release profile being a property of the composition not formulation. In contrast, conventional extended release formulations used to control the release of methylphenidate are subject to release of up to the entire methylphenidate content immediately following crushing. When the content of the crushed tablet is injected or snorted, the large dose of methylphenidate produces the "rush" effect sought by addicts.

The present technology provides a stimulant based treatment modality and dosage form for certain disorders requiring the stimulation of the CNS such as, attention-deficit hyperactivity disorder (ADHD), attention deficit disorder (ADD), autistic spectrum disorder, autism, Asperger's disorder, pervasive developmental disorder, sleep disorder, obesity, depression, bipolar disorder, eating disorder, chronic fatigue syndrome, schizophrenia, major depressive disorder narcolepsy, or autistic spectrum disorder. Although not wanting to be bound by any particular theory, it is believed that the treatment of such CNS conditions as noted above with compositions of the present technology results in increased bioavailability as compared to existing stimulant treatment modalities and dosage forms. In a preferred embodiment, the at least one prodrug or composition of the present technology is used to treat attention-deficit hyperactivity disorder (ADHD).

In some embodiments, the at least one composition or prodrug of the present technology can be used in one or more methods of treating a patient having at least one disease, disorder or condition requiring stimulation of the central nervous system of one or more patients, comprising orally administering a pharmaceutically effective amount of the at least one composition or prodrug.

In some embodiments, the at least one composition or prodrug of the present technology can be used in one or more methods of treating one or more patients having at least one disease, disorder or condition mediated by controlling, preventing, limiting, or inhibiting neurotransmitter uptake/re-uptake or hormone uptake/re-uptake comprising administering to at least one patient a pharmaceutically effective amount of the at least one prodrug or composition. In some embodiments, the neurotransmitter is serotonin, dopamine or norepinephrine. In some embodiments, the hormone is catecholamine.

At least some compositions of the present technology comprising the prodrugs of methylphenidate, derivatives thereof or combinations thereof, can also be used for treating stimulant (cocaine, methamphetamine) abuse and addiction, for improving battle field alertness, and/or for combating fatigue.

The at least one prodrug or conjugate of the present technology can be formulated in to dosage forms to be administered orally. These dosage forms include but are not limited to tablet, capsule, caplet, troche, lozenge, powder, suspension, syrup, solution, oral thin film (OTF), oral strips, inhalation compounds or suppositories. Preferred oral administration forms are capsule, tablet, solutions and OTF. Suitable dosing vehicles of the present technology include, but are not limited to, water, phosphate buffered saline (PBS), 10% Tween in water, and 50% PEG-400 in water.

Solid dosage forms can optionally include the following types of excipients: antiadherents, binders, coatings, disintegrants, fillers, flavors and colors, glidants, lubricants, preservatives, sorbents and sweeteners.

Oral formulations of the present technology can also be included in a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used, as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated and then compressed using methods and machinery known to those in the industry. The resultant compressed tablet dosage units are then packaged according to market need, for example, in unit dose, rolls, bulk bottles, blister packs, etc.

The present technology also contemplates the use of biologically-acceptable carriers which may be prepared from a wide range of materials. Without being limited to, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g., solid and liquid diluents, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

Methylphenidate is being marketed in numerous dosage forms and at various dosage strengths either as racemic mixture of d- and l-threo-methylphenidate or as single d-threo-isomer (Table 1). Recommended daily doses depend on the dosage form, active ingredient (single isomer or racemic mixture) and individual patient titration.

TABLE 1

Examples of marketed methylphenidate dosage forms and dosage strengths.

| Active Ingredient | Dosage Form | Dosage Strength(s) | Proprietary Name(s) |
|---|---|---|---|
| methylphenidate hydrochloride | instant release tablet | 5, 10, 20 mg | Ritalin ® |
| dexmethylphenidate hydrochloride | instant release tablet | 2.5, 5, 10 mg | Focalin ® |
| methylphenidate hydrochloride | extended release tablet | 10, 20 mg | Methylin ER ®, Metadate ER ® |
| methylphenidate hydrochloride | extended release tablet | 10, 18, 20, 27, 36, 54 mg | Concerta ® |
| methylphenidate hydrochloride | chewable tablet | 2.5, 5, 10 mg | Methylin |
| methylphenidate hydrochloride | extended release capsules | 10, 20, 30, 40 mg | Ritalin LA ® |
| methylphenidate hydrochloride | extended release capsules | 10, 20, 30, 40, 50, 60 mg | Metadate CD ® |
| dexmethylphenidate hydrochloride | extended release capsules | 5, 10, 15, 20, 30, 40 mg | Focalin XR ® |
| methylphenidate | transdermal patch | 10, 15, 20, 30 mg/9 h | Daytrana ® |
| methylphenidate hydrochloride | oral solution | 5, 10 mg/5 mL | Methylin ® |

Doses of the prodrug of the present technology can be higher or lower than doses of unconjugated methylphenidate depending on their molecular weight, the respective weight-percentage of methylphenidate as part of the whole conjugate or conjugate salt and their bioavailability (with respect to released methylphenidate). Therefore dosages may be higher or lower than the dosages of free methylphenidate.

Dosages can be calculated based on the strengths of dosages of methylphenidate hydrochloride which range between, for example, but not limited to, about 2.5 mg and about 54 mg per dose. Dose conversion from methylphenidate hydrochloride to methylphenidate prodrug can be performed using the following formula:

$$\text{dose (MPH prodrug)} = f_{BA} \times \text{dose (MPH hydrochloride)} \times \frac{MW \text{ (MPH prodrug)}}{269.77 \frac{g}{mol}}$$

MPH=methylphenidate
MW=molecular weight
$f_{BA}$=correction factor accounting for differences in bioavailability between unmodified methylphenidate and prodrugs of the present technology. This correction factor is specific for each prodrug.

Suitable dosages of the conjugated methylphenidate or prodrugs of the present technology include, but are not limited to, formulations including an amount of conjugated methylphenidate equimolar to an amount of unconjugated methylphenidate from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, and include any additional increments thereof, for example, about 0.1, about 0.2, about 0.25, about 0.3, about 0.4, about 0.5, about 0.6, about 0.7, about 0.75, about 0.8, about 0.9 or about 1.0 mg and multiplied factors thereof, (e.g., about ×1, about ×2, about ×2.5, about ×5, about ×10, about ×100, etc). The present technology also includes dosage formulations including currently approved formulations of methylphenidate (See Table 1), where the dosage can be calculated using the above-noted formula determined by the amount of methylphenidate hydrochloride. The present technology provides for dosage forms formulated as a single therapy or as a combination therapy.

In some embodiments, the conjugates of methylphenidate and oxoacids to form prodrugs have one or more advantage, including, but not limited to, reduced or improved side effect profile, formation of less potentially toxic metabolites, formation of less inactive metabolites, improved water solubility, reduced drug abuse potential and/or reduced interpatient variability in plasma concentrations as compared to unconjugated methylphenidate.

Synthetic Schemes

In some embodiments, one or more protecting groups may be attached to any additional reactive functional groups that may interfere with the coupling to methylphenidate. Any suitable protecting group may be used depending on the type of functional group and reaction conditions. Some protecting group suitable for use in the present technology include, but not limited to, acetyl (Ac), tert-butyoxycarbonyl (Boc), benzyloxycarbonyl (Cbz), p-methoxybenzylcarbonyl (Moz), 9-fluorenylmethyloxycarbonyl (Fmoc), benzyl (Bn), p-methoxybenzyl (PMB), 3,4 dimethoxybenzyl (DMPM), p-methozyphenyl (PMP), tosyl (Ts), or amides (like acetamides, pthalamides, and the like).

In other embodiments, a base may be required at any step in the synthetic scheme of prodrugs of methylphenidate of this invention. Suitable bases include, but are not limited to, 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert-butoxide (e.g., potassium tert-butoxide), any alkali metal hydride (e.g., sodium hydride), any alkali metal alkoxide (e.g., sodium methoxide), triethylamine or any other tertiary amine.

Suitable solvents that can be used for any reaction at any step in the synthetic scheme of a prodrug of methylphenidate of this invention include, but are not limited to, acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

In some embodiments, an acid may be used to remove certain protecting groups. Suitable acids include, but are not limited to, hydrochloric acid, hydrobromic acid, hydrofluoric acid, hydriodic acid, sulfuric acid, phosphoric acid, trifluoroacetic acid, acetic acid, citric acid, methanesulfonic acid, p-toluenesulfonic acid and nitric acid. For certain other protecting groups, a catalytic hydrogenation may be used, e.g., palladium on charcoal in the presence of hydrogen gas.

In one embodiment, the general synthesis of linking oxoacids to methylphenidate include the following reactions. To a solution of iodomethyl carbamate of methylphenidate (1-1.5 mmol) in toluene (25-50 mL) was added the silver salt of the respective oxoacid (3 eq.). The reaction was heated from 80° C. to reflux for 3 hours depending on the oxoacid. Subsequently, the solid was filtered off and the filtrate was concentrated. The residue was purified by column chromatography to give the linked oxoacid-methylphenidate conjugate.

Depending on the oxoacid the conjugate was either the final product or required deprotection. For example, the benzyl groups protecting the phosphate conjugate were removed by hydrogenation with 10% Pd/C in methanol using a hydrogen balloon for 2 hours. The catalyst was filtered off and the filtrate was concentrated and dried to give the final deprotected conjugate.

In some embodiments, the prodrug is hydrophilic and thus more water soluble than the unconjugated methylphenidate.

In some embodiments, the general procedure for the synthesis of carbamate derivatives of methylphenidate (MPH) with alkyl or aryl groups (3) is as follows:

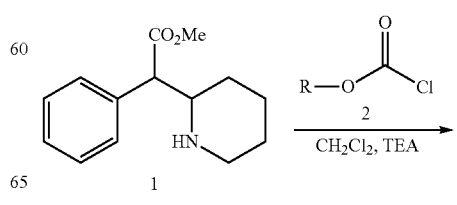

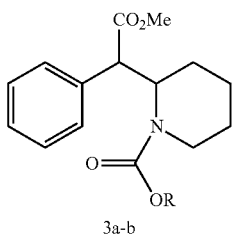

3a-b

3a: R = —CH$_2$—Ph
3b: R = -4-F-Ph

To a solution of methylphenidate hydrochloride (MPH-.HCl) (1 mmol) and triethylamine (TEA) (4 mmol) in dichloromethane (DCM) (8 mL) was added a solution of chloroformate 2 (2 mmol) in DCM (2 mL) drop-wise at room temperature. After 4-6 h, the reaction was quenched with water (1 mL) and stirred for 15 min. The solvent was evaporated under reduced pressure. The residue was dissolved in ethylacetate (EtOAc) (50 mL) and washed with 5% aqueous sodium bicarbonate (NaHCO$_3$) (2×40 mL) and brine (1×40 mL). The organic phase was dried under sodium sulfate (Na$_2$SO$_4$) and concentrated in vacuum. The oily residue was purified either by silica gel chromatography or preparative HPLC.

In other embodiments, the synthesis of 4-fluorophenol-CO-MPH (3b) is as follows:

To a solution of To a solution of MPH.HCl (0.25 g, 0.93 mmol) and TEA (0.52 mL, 3.7 mmol) in DCM (8 mL) was added a solution of 4-fluorophenyl chloroformate (0.33 g, 1.86 mmol) in DCM (3 mL) drop-wise at room temperature. The reaction mixture was stirred for 6 h at room temperature and then quenched with water (1 mL). The solvent was evaporated under reduced pressure. The residue was dissolved in EtOAc (50 mL) and washed with 5% aqueous NaHCO$_3$ (2×40 mL) and brine (1×40 mL). The organic phase was dried under Na$_2$SO$_4$ and concentrated in vacuum. The oily residue was purified by preparative HPLC to give 3b (0.35 g).

In some embodiments, the general procedure for the synthesis of carbamate derivatives of MPH with hydroxy carboxylic acids (8) is as follows:

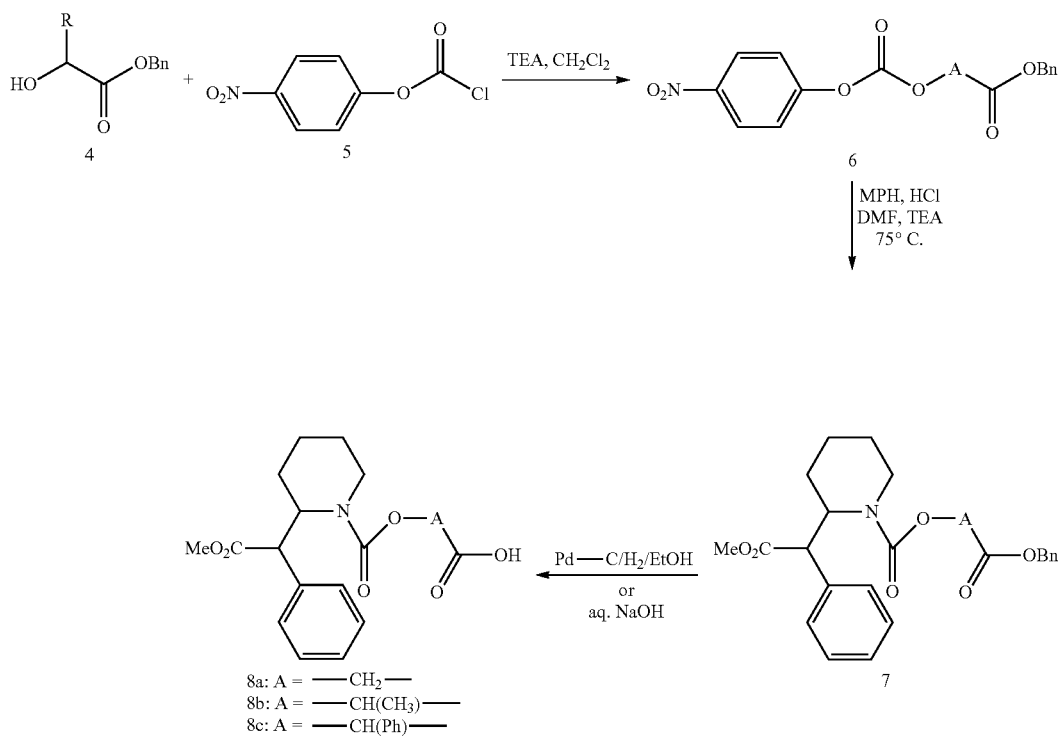

8a: A = —CH$_2$—
8b: A = —CH(CH$_3$)—
8c: A = —CH(Ph)—

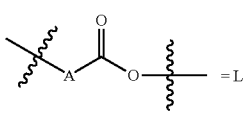 = L

To a solution of protected hydroxyl acid 4 (1 mmol) in DCM (8 mL) was added TEA (2.5 mmol) and the solution was cooled down to 0° C. A solution of 4-nitrophenyl chloroformate (5, 1 mmol) in DCM (2 mL) was added drop-wise at 0° C. After the addition the reaction mixture was slowly brought to room temperature and left overnight. The solvent was evaporated and dried in vacuum to give the carbonate derivative 6. Compound 6 was dissolved in dimethylformamide (DMF) and to the solution were added TEA (3 mmol) and MPH.HCl (1.05 mmol). The mixture was heated for 8 h at 75° C. Solvent was removed under reduced pressure. The residue was dissolved in EtOAc (60 mL) and washed with 5% aq. NaHCO$_3$ (2×40 mL) and brine (1×40 mL). The organic phase was dried over Na$_2$SO$_4$ and evaporated to dryness to give 8, which was purified by preparative HPLC.

In other embodiments, the synthesis of MPH—CO-l-lactate (8b, A=—CH(CH$_3$)—) is as follows:

To a solution of benzyl lactate 4 (A=—CH(CH$_3$)—; 0.39 g, 2 mmol) in DCM (8 mL) was added TEA (0.69 mL, 5 mmol) and the solution was cooled down to 0° C. A solution of 4-nitrophenyl chloroformate 5 (0.436 g, 2.1 mmol) in DCM (3 mL) was added drop-wise at 0° C. Subsequently, the reaction mixture was slowly brought to room temperature and left overnight. The solvent was evaporated in vacuum and dried to give the carbonate derivative 6 (A=—CH(CH$_3$)—). Compound 6 was dissolved in DMF (12 mL) and to the solution were added TEA (0.84 mL, 6 mmol) and MPH.HCl (0.604 g, 2.23 mmol). The mixture was heated for 20 h at 65° C. Solvent was removed under reduced pressure. The residue was dissolved in EtOAc (40 mL) and was washed with 5% aq. NaHCO$_3$ (2×30 mL) and brine (1×30 mL). The organic phase was dried over Na$_2$SO$_4$, evaporated to dryness and purified by preparative HPLC to give 8b (0.62 g).

In other embodiments, the general procedure for the synthesis of aminoacid derivatives of MPH with hydroxy carboxylic acid linkers (11) is as follows:

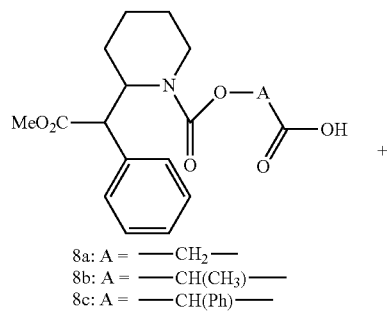

8a: A = —CH$_2$—
8b: A = —CH(CH$_3$)—
8c: A = —CH(Ph)—

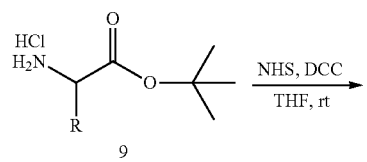

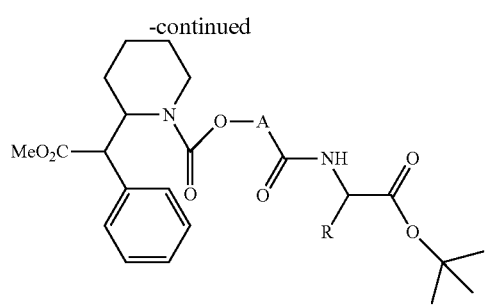

10

4N HCl/dioxane

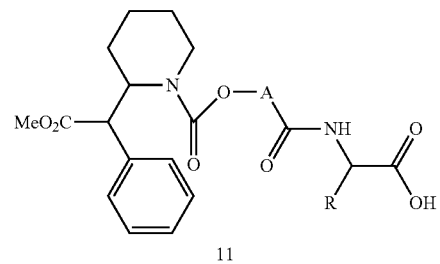

11

R = side chain of amino acid

To a solution of 8 (1 mmol), H-AA-O$^t$Bu (AA=amino acid) (9, 1.1 mmol), N-hydroxysuccinidimide (NHS) (1.1 mmol) in THF (8 mL) was added TEA (2 mmol) and the mixture was stirred for 10 min. Subsequently, a solution of N,N'-dicyclohexylcarbodiimide (DCC) (1.1. mmol) in THF (2 mL) was added and the mixture was stirred overnight at room temperature. The reaction mixture was filtered and the filtrate was evaporated to dryness to give the protected derivative 10, which was purified by preparative HPLC.

Compound 10 was dissolved in 4N HCl/dioxane solution (8 mL) and the solution was stirred for 6 h at room temperature. The solution was evaporated under vacuum, co-evaporated with isopropyl acetate and dried to give 11.

In some embodiments, the synthesis of MPH-CO-lactoyl-Lys (11a; A=—CH(CH$_3$)—, R=—(CH$_2$)$_4$NH$_2$) is as follows:

To a solution of 8b (0.12 g, 0.34 mmol), H-Lys(Boc)-O$^t$Bu.HCl 9 (0.145 g, 0.37 mmol), NHS (0.044 g, 0.37 mmol) in THF (8 mL) was added TEA (0.15 mL, 1.02 mmol) and the mixture was stirred for 10 min. Subsequently, a solution of DCC (0.076 g, 0.37 mmol) in THF (2 mL) was added and the mixture was stirred overnight at room temperature. The reaction mixture was filtered and the filtrate was evaporated to dryness. The crude product was purified by preparative HPLC to give 10a (0.14 g).

Compound 10a (A=—CH(CH$_3$)—, R=—(CH$_2$)$_4$NH$_2$) (0.135 g) was dissolved in 4N HCl/dioxane (8 mL) and the solution was stirred for 6 h at room temperature. The solution was evaporated in vacuum, co-evaporated with isopropyl acetate (IPAc) and dried to give 11a (0.12 g).

In other embodiments, the synthesis of MPH-CO-lactoyl-Ala (11b; A=—CH(CH$_3$)—, R=—CH$_3$) is as follows:

To a solution of 8b (0.12 g, 0.34 mmol), H-Ala-O$^t$Bu.HCl 9 (0.0.065 g, 0.36 mmol), NHS (0.044 g, 0.37 mmol) in THF (8 mL) was added TEA (0.15 mL, 1.02 mmol) and the mixture was stirred for 10 min. Subsequently, a solution of DCC (0.075 g, 0.36 mmol) in THF (2 mL) was added and the reaction was stirred overnight at room temperature. The suspension was filtered and the filtrate was evaporated to dryness. The crude product was purified by preparative HPLC to give 10b (A=—CH(CH$_3$)—, R=—CH$_3$) (0.095 g).

Compound 10b (A=—CH(CH$_3$)—, R=—CH$_3$) (0.09 g) was dissolved in 4N HCl/dioxane (8 mL) and the solution was stirred for 4 h at room temperature. The solution was evaporated in vacuum, co-evaporated with isopropyl acetate (IPAc) and dried to give 11 b (0.085 g).

In other embodiments, the general procedure for the synthesis of carbamate derivatives of MPH with amino alcohols (15) is as follows:

mixture was heated for 15 h at 65° C. Solvent was removed under reduced pressure. The residue was dissolved in EtOAc (40 mL) and washed with 5% aq. NaHCO$_3$ (2×30 mL) and brine (1×30 mL). The organic phase was dried over Na$_2$SO$_4$ and evaporated to dryness to give 14, which was purified by preparative HPLC. Compound 14 was dissolved in 4N HCl/dioxane and the solution was stirred under argon for 3-6 h depending on the amino acid derivative. The solvent was evaporated, co-evaporated with IPAc and dried to give 15.

In other embodiments, the synthesis of tyramine-CO-MPH (19) is as follows:

To a solution of Boc-tyramine 16 (1 mmol) in DCM (8 mL) was added TEA (2.5 mmol) and the solution was cooled down to 0° C. A solution of 4-nitrophenyl chloroformate (5, 1 mmol) in DCM was added drop-wise at 0° C. Subsequently, the ice bath was removed and the reaction mixture was stirred for 4 h at room temperature. The solvent was evaporated under vacuum and dried to give the carbonate derivative 17. Compound 17 was dissolved in DMF and to the solution were added TEA (3 mmol) and MPH.HCl (1.05 mmol). The mixture was heated for 15 h at 65° C. Solvent

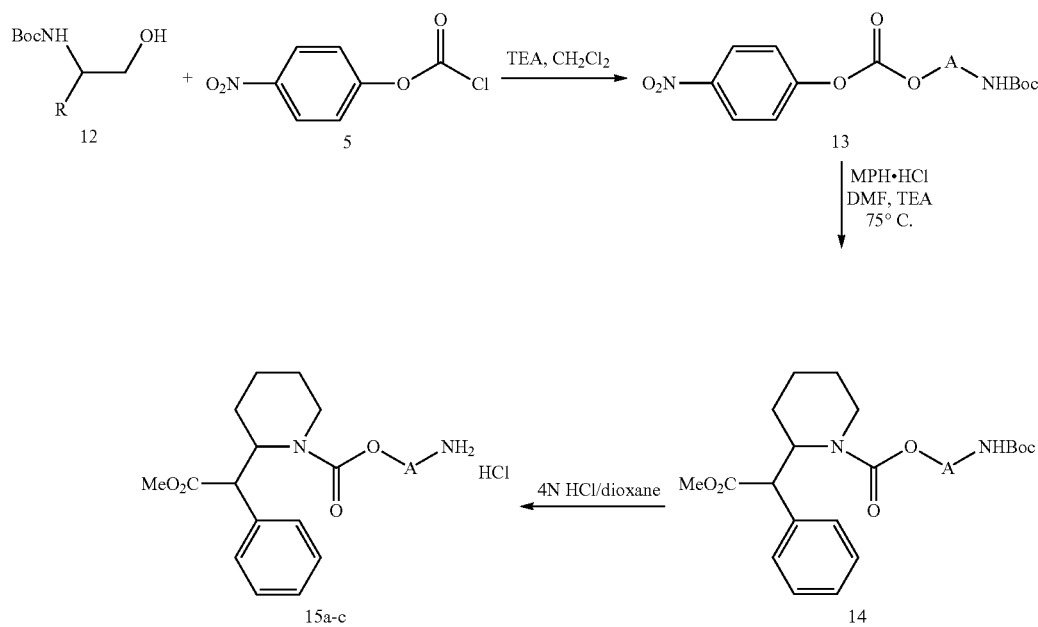

15a: A = —(CH$_2$)$_2$—
15b: A = —CH$_2$CH(CH$_3$)—
15c = 19: A = —C$_4$H$_4$—(CH$_2$)$_2$—

To a solution of amino alcohol 12 (1 mmol) in DCM (8 mL) was added TEA (2.5 mmol) and the solution was cooled down to 0° C. A solution of 4-nitrophenyl chloroformate (5, 1 mmol) in DCM was added drop-wise at 0° C. Subsequently, the reaction mixture was slowly brought to room temperature and left overnight at rt. The solvent was evaporated in vacuum and dried to give the carbonate derivative 13. Compound 13 was dissolved in DMF and to the solution were added TEA (3 mmol) and MPH.HCl (1.05 mmol). The was removed under reduced pressure. The residue was dissolved in EtOAc (40 mL) and was washed with 5% aq. NaHCO$_3$ (2×30 mL) and brine (1×30 mL). The organic phase was dried over Na$_2$SO$_4$ and evaporated to dryness to give 18, which was purified by preparative HPLC. Compound 18 was deprotected with 4N HCl/dioxane to produce 19 (0.38 g).

In some embodiments, the synthesis of succinate-tyramine-CO-MPH (20) is as follows:

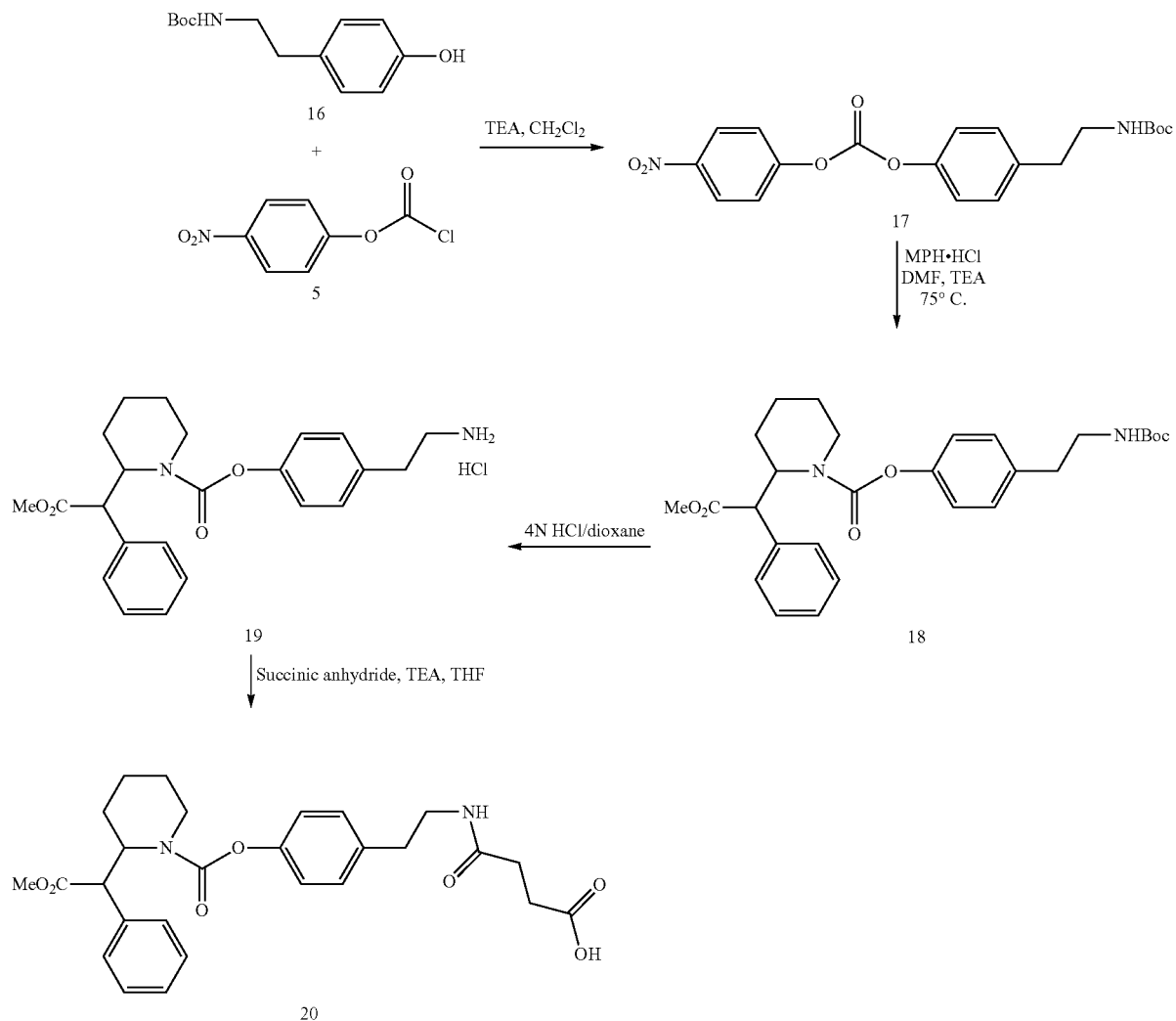

To a solution of 19 (0.1 g, 0.23 mmol) and TEA (0.095 mL, 0.69 mmol) in THF (8 mL) was added succinic anhydride (0.025 g, 0.25 mmol) and the reaction mixture was stirred for 3 h at room temperature. Solvent was evaporated under reduced pressure and the residue was dissolved in EtOAc (50 mL). The EtOAc phase was washed with 1% aq. sodium bisulfate (NaHSO$_4$) (50 mL), brine (50 mL). The organic phase was dried over Na$_2$SO$_4$ and evaporated to dryness to give 20 (0.11 g) as white solid.

In other embodiments, the general procedure for the synthesis of carboxylic acid derivatives of MPH with amino alcohol linkers (23 and 25) is as follows:

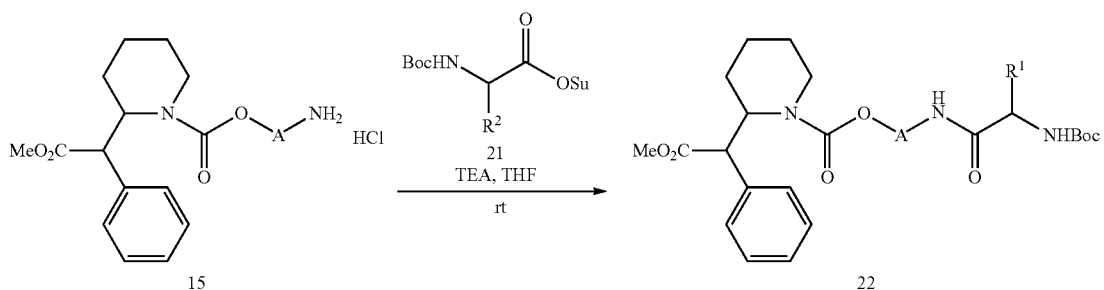

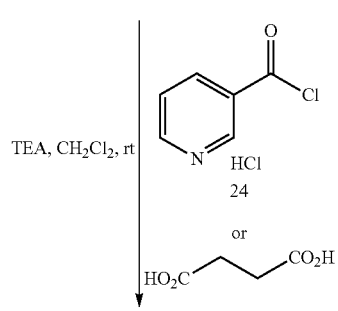
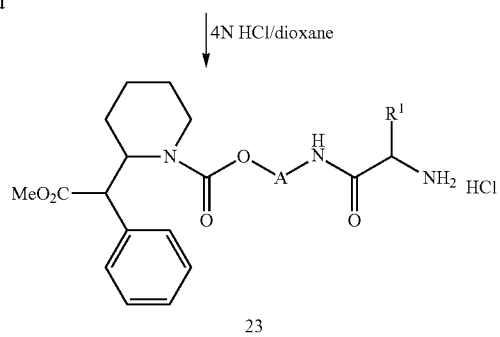

23

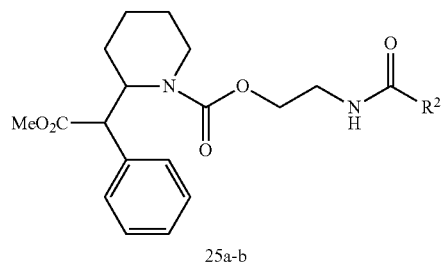

25a-b

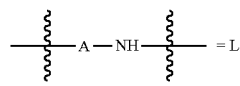

$R^2$ = side chain of amino acid

25a: $R^2$ = 3-pyridinyl
25b: $R^2$ = —$(CH_2)_2CO_2H$

To a solution of 15 (1 mmol) in THF were added TEA (2.5 mmol) and Boc-AA-OSu (AA=amino acid) (21, 1.05 mmol) and the solution was stirred for 3 h at room temperature. Solvent was evaporated in vacuum. The residue was dissolved in EtOAc (50 mL) and washed with 5% aq. NaHCO$_3$ (2×30 mL) and brine (1×40 mL). The organic phase was dried over Na$_2$SO$_4$ and evaporated to dryness to give 22. After purification, compound 21 was dissolved in 4N HCl/dioxane and stirred for 3-6 h at room temperature. Solvent was evaporated, the residue was co-evaporated with IPAc and dried to give 23.

In some embodiments, the synthesis of Lys-alaninol-CO-MPH (23; A=—CH$_2$CH(CH$_3$)—, $R^1$=—(CH$_2$)$_4$NH$_2$) is as follows:

To a solution of 15b (0.09 g, 0.24 mmol) in THF were added TEA (2.5 mmol) and Boc-Lys(Boc)-OSu 21 (0.113 g, 0.25 mmol) and the solution was stirred for 3 h at room temperature. Solvent was evaporated in vacuum. The residue was dissolved in EtOAc (50 mL) and was washed with 5% aq. NaHCO$_3$ (2×30 mL) and brine (1×40 mL). The organic phase was dried over Na$_2$SO$_4$ and evaporated to dryness to give 22 (A=—CH$_2$CH(CH$_3$)—, $R^1$=—(CH$_2$)$_4$NH$_2$). After purification, compound 22 (0.135 g) was dissolved in 4N HCl/dioxane and stirred for 2 h at room temperature. Solvent was evaporated, the residue was co-evaporated with IPAc and dried to give 23 (0.13 g).

In other embodiments, the synthesis of nicotinate-ethanolamine-CO-MPH (25a; $R^2$=3-pyridinyl) is as follows:

To a solution of 15a (0.1 g, 0.28 mmol) and TEA (0.15 mL, 1.12 mmol) in DCM (8 mL) was added nicotinoyl chloride (0.055 g, 0.31 mmol). After stirring for 2 h at room temperature, the reaction was quenched with water (1 mL) and solvent was evaporated to dryness. The residue was dissolved in EtOAc (60 mL) and washed with 5% aq. NaHCO$_3$ (2×50 mL) and brine (1×50 mL). The organic phase was dried over Na$_2$SO$_4$ and evaporated to dryness to give nicotinic acid derivative 25a (0.13 g).

In some embodiments, the synthesis of succinate-ethanolamine-CO-MPH (25b; $R^2$=—(CH$_2$)$_2$CO$_2$H) is as follows:

To a solution of 15a (0.11 g, 0.31 mmol) and TEA (0.13 mL, 0.9 mmol) in THF (8 mL) was added succinic anhydride (0.034 g, 0.34 mmol) and the reaction mixture was stirred for 3 h at room temperature. The reaction was quenched with water and the solvent was evaporated under reduced pressure. The residue was dissolved in EtOAc (50 mL) and washed with 1% aq. NaHSO$_4$ (2×40 mL), brine (50 mL). The organic phase was dried over Na$_2$SO$_4$ and evaporated to dryness to give 25b (0.12 g) as solid.

In other embodiments, the synthesis of glycerol-CO-MPH (29) is as follows:

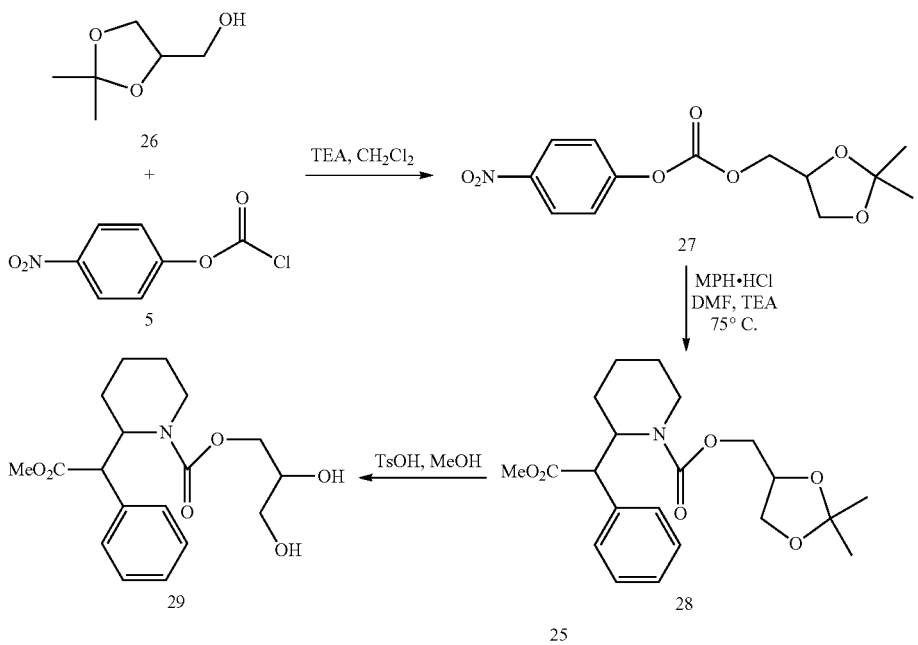

A solution of 1,2-isopropylideneglycerol 26 (0.265 g, 2 mmol) and TEA (0.55 mL, 4 mmol) in DCM (8 mL) was cooled down to 0° C. Subsequently, a solution of 4-nitrophenyl chloroformate 5 (0.425 g, 2 mmol) in DCM was added drop-wise. The ice bath was removed and the reaction mixture was stirred for 5 h at room temperature. Solvents were evaporated in vacuum and dried to give the carbonate derivative 27. Compound 27 was dissolved in DMF and to the solution were added TEA (0.69 mL, 5 mmol) and MPH.HCl (0.502 g, 1.85 mmol). The mixture was heated for 15 h at 70° C.

Solvent was removed under reduced pressure. The residue was dissolved in EtOAc (70 mL) and washed with 5% aq. NaHCO$_3$ (2×50 mL) and brine (1×50 mL). The organic part was dried over Na$_2$SO$_4$ and evaporated to dryness to give carbamate derivative 28 (0.61 g) after purification by preparative HPLC.

Isopropylidene derivative 28 (0.6 g) was dissolved in methanol (MeOH) (20 mL) and to the solution was added toluenesulfonic acid monohydrate (TsOH.H$_2$O) (0.035 g). After stirring for 3 h at room temperature, the reaction was quenched with 5% aq. NaHCO$_3$ (1 mL) and solvent was evaporated to dryness. The residue was dissolved in EtOAc (70 mL) and washed with 5% aq. NaHCO$_3$ (2×50 mL) and brine (1×50 mL). The organic phase was dried over Na$_2$SO$_4$ and evaporated to dryness to give glycerol derivative 29 (0.46 g).

In other embodiments, the synthesis of carbamate conjugates of MPH with poly(ethylene glycol) derivatives (32) is as follows:

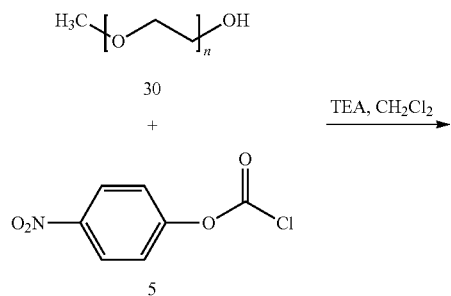

-continued

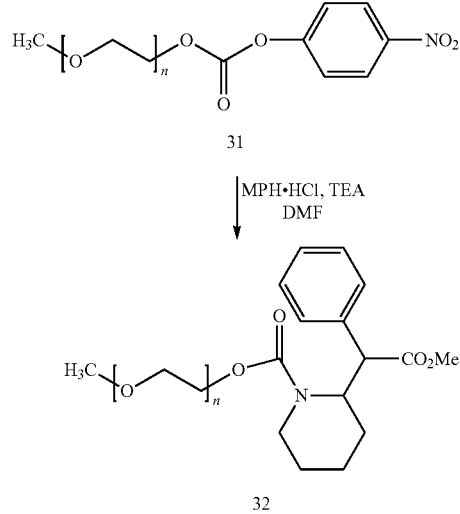

In some embodiments, the synthesis of Me-PEG-CO-MPH (32a) is as follows:

To a solution of Me-PEG (poly(ethylene glycol) methyl ether) 30 (1 mmol) and TEA (2 mmol) in DCM (8 mL) was added drop-wise a solution of 4-nitrophenyl chloroformate 5 (1.05 mmol) in DCM (3 mL) at room temperature. The solution was stirred overnight at room temperature. The solvent was evaporated in vacuum and dried to give the carbonate derivative 31. Compound 31 was dissolved in DMF and to the solution were added TEA (3 mmol) and MPH.HCl (1.05 mmol). The mixture was heated for 15 h at 70° C. Solvent was removed under reduced pressure. The oily residue was purified by preparative HPLC to give 32a as oil.

In other embodiments, the synthesis of Me-(OCH$_2$CH$_2$)$_3$—OCO-MPH (32b; n=3) is as follows:

To a solution of Me-PEG 30 (n=3; 0.165 g, 1 mmol) and TEA (0.3 mL, 2 mmol) in DCM (8 mL) was added dropwise a solution of 4-nitrophenyl chloroformate 5 (0.212 g, 1.05 mmol) in DCM (3 mL) at room temperature. The solution was stirred overnight at room temperature. The solvent was evaporated in vacuum and dried to give the carbonate derivative 31 (n=3). Compound 31 was dissolved in DMF and to the solution were added TEA (0.42 mL, 3 mmol) and MPH.HCl (0.273 g, 1.05 mmol). The mixture was heated for 6 h at 75° C. Solvent was removed under reduced pressure. The oily residue was purified by preparative HPLC to give 32b (n=3) (0.24 g) as oil.

In some embodiments, the synthesis of H$_2$N-PEG-CO-MPH (34) is as follows:

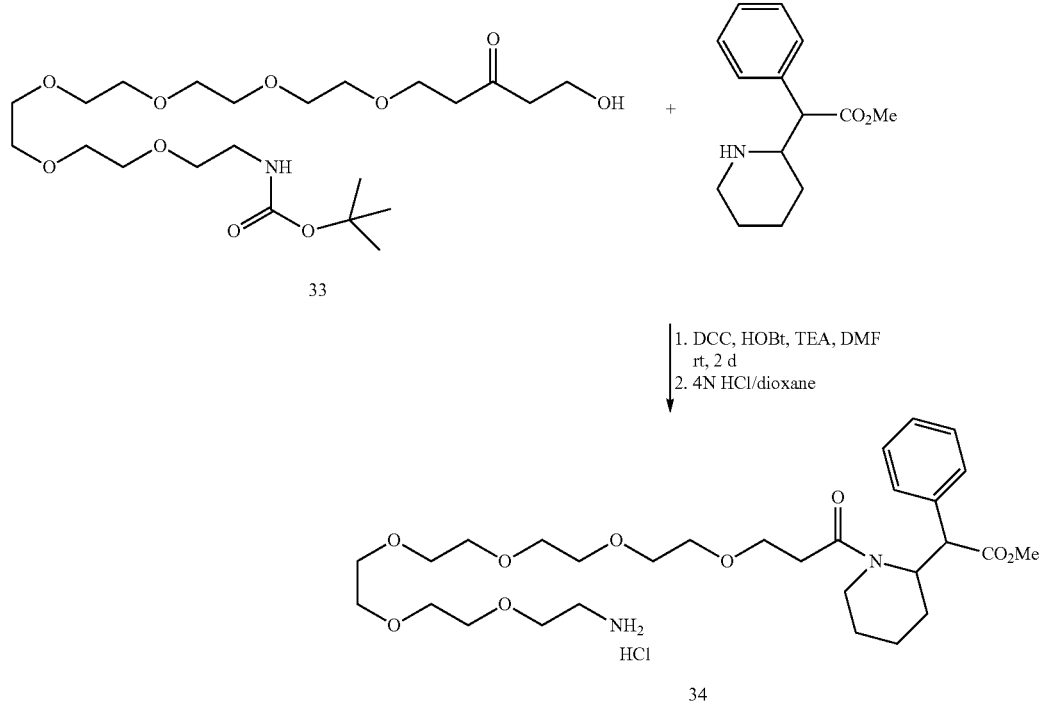

To a solution of O[2-(Boc-amino)ethyl]-O'-(2-carboxyethyl)polyethylene glycol (Boc-NH-PEG-CO$_2$H) 33 (0.12 g, 0.26 mmol), MPH.HCl (0.93 g, 0.35 mmol), 1-hydroxybenzotriazole (HOBt) (0.035 g, 0.26 mmol) and TEA (0.11 mL, 0.78 mmol) in DMF (6 mL) was added a solution of DCC (0.056 g, 0.27 mmol) drop-wise. The reaction mixture was stirred for 2 days at room temperature. The suspension was filtered and the filtrate was evaporated to dryness in vacuum. The residue was purified and deprotected with 4N HCl/dioxane to give the amide derivative 34 (0.13 g) as oil.

In other embodiments, the synthesis of Me-PEG-NH-succinoyl-alaninol-CO-MPH (36) is as follows:

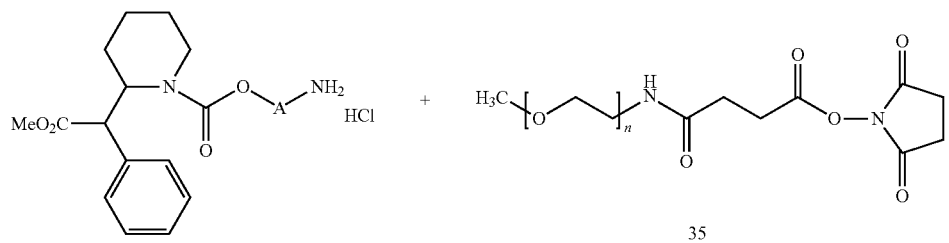

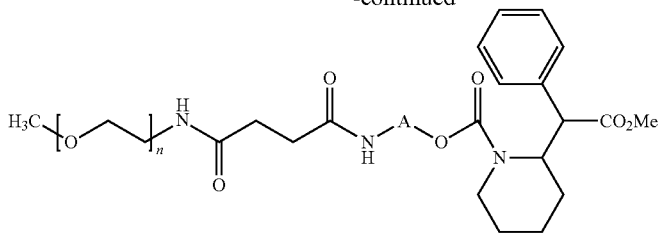

36

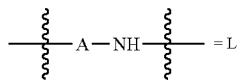

To a solution of 15b (0.075 g, 0.2 mmol) and TEA (0.085 mL, 0.6 mmol) in THF (8 mL) was added O—[(N-succinimidyl)succinyl-aminoethyl]-O'-methylpolyethylene glycol (Me-PEG-Suc-OSu) 35 (average. $M_p$=750, 0.15 g, 0.2 mmol) and the reaction mixture was stirred for 2 days at room temperature. Solvent was evaporated under reduced pressure and the residue was purified by preparative HPLC to give 36 as oil.

In some embodiments, the synthesis of 6-aminohexanoate-CH$_2$OCO-MPH (40) is as follows:

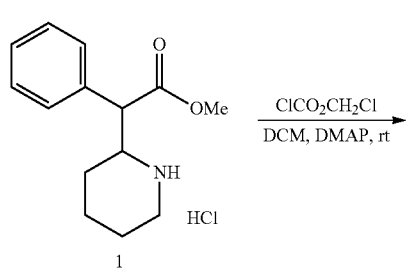

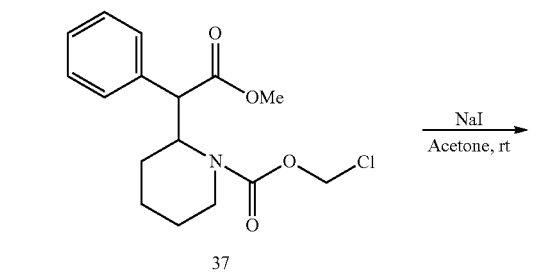

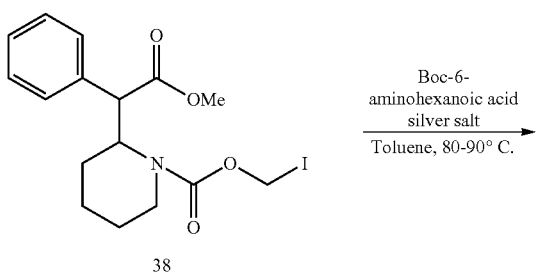

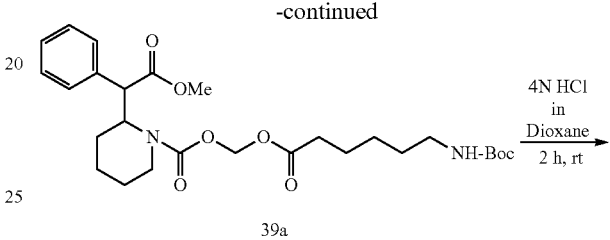

39a

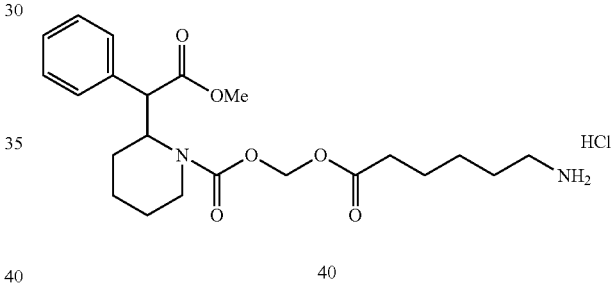

40

A. Synthesis of Boc-6-aminohexanoic acid silver salt

Boc-6-aminohexanoic acid (0.85 g, 3.68 mmol) was added to water (4 mL) and cooled in ice bath. To this suspension 1N NaOH was added with constant stirring until the pH of solution was about 7 and the mixture became a clear solution. To this solution, silver nitrate (0.63 g, 3.68 mmol) in water (2 mL) was added slowly. The resulting precipitate was filtered and washed with water. The solid was dried in vacuum over phosphorus pentoxide to yield a white solid (1.09 g) (yield, 88%).

B. Synthesis of chloromethyl 2-(2-methoxy-2-oxo-1-phenylethyl)piperidine-1-carboxylate (37)

Methylphenidate hydrochloride (1) (2.70 g, 10 mmol) was suspended in DCM (75 mL) and cooled in an ice bath. 4-Dimethylaminopyridine (DMAP) (4.887 g, 40 mmol) was added and the resulting mixture was stirred for 10 min. Chloromethyl chloroformate (3.224 g, 25 mmol) in DCM (10 mL) was added slowly. The ice bath was removed and the reaction was stirred for 5 h at room temperature. Ethyl acetate (250 mL) was added, followed by water (20 mL) to quench the reaction. The ethyl acetate layer was separated and washed with 1N HCl (40 mL) and brine (2×40 mL) and dried over anhydrous sodium sulfate. The solvent was evaporated and the residue was purified by silica gel column chromatography (hexanes:EtOAc, 3:1) to give 37 as a colorless oil (2.60 g) (yield, 80%).

C. Synthesis of iodomethyl 2-(2-methoxy-2-oxo-1-phenylethyl)piperidine-1-carboxylate (38)

A mixture of 37 (0.28 g, 0.86 mmol) and sodium iodide (0.387 g, 2.58 mmol) in acetone (6 mL) was stirred overnight. The acetone was evaporated. The residue was dissolved in ethyl acetate (80 mL) and washed with saturated sodium bisulfate (30 mL) and brine (30 mL) and dried over anhydrous sodium sulfate. The solvent was evaporated and the residue was dried in vacuum to give 38 as a syrup (0.263 g) (yield, 73%).

D. Synthesis of Boc-6-aminohexanoate-CH$_2$OCO-MPH (39a)

A mixture of 38 (0.43 g, 1.03 mol) and Boc-6-aminohexanoic acid silver salt (1.05 g, 3.09 mmol) in toluene (30 mL) was refluxed for 3 h. The solid was filtered off and the filtrate was concentrated to dryness. The crude residue was purified by preparative HPLC to give 39a as a hygroscopic solid (0.375 g) (yield, 70%).

E. Synthesis of 6-aminohexanoate-CH$_2$OCO-MPH (40)

Compound 39a (0.21 g, 0.40 mmol) was stirred with 4N HCl/dioxane (5-6 mL) for 2 h at room temperature. The solvent was concentrated to dryness to yield 40 as a hygroscopic solid (0.166 g) (yield, 91%).

In other embodiments, the synthesis of lactate-CH$_2$OCO-MPH (39b) is as follows:

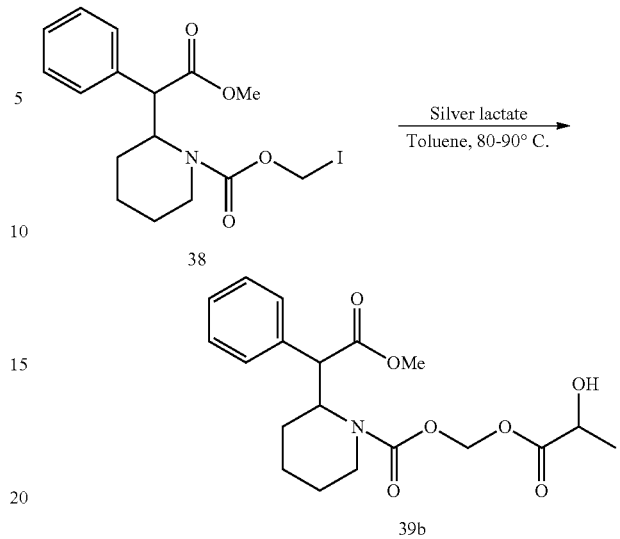

A mixture of compound 38 (0.428 g, 1.03 mmol) and silver lactate (0.61 g, 3.09 mmol) in 30 mL toluene was heated at 80-90° C. for 3 h. The solid was filtered off and the filtrate was concentrated to dryness. The crude residue was purified by preparative HPLC to give 39b as syrup (0.28 g) (yield, 64%).

In some embodiments, the general procedure for the synthesis of amino acid and peptide derivatives of (6-aminohexanoyloxy)methyl methylphenidate-1-carboxylate conjugates (42) is as follows:

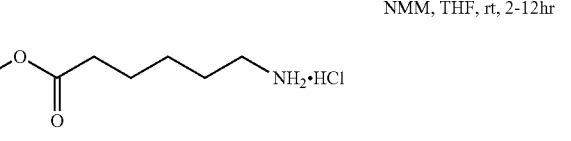

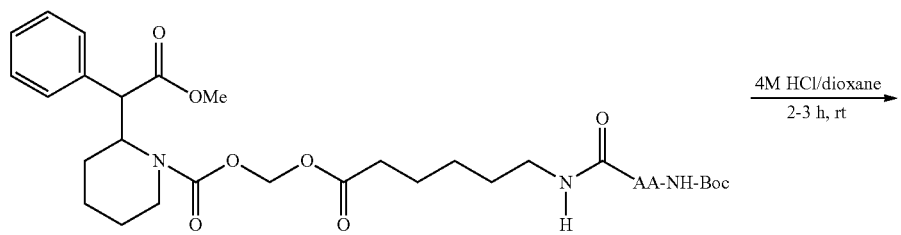

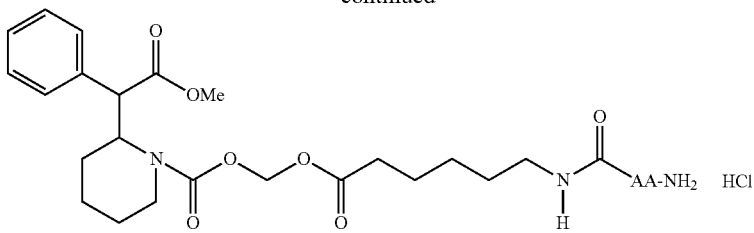

42

AA = Amino acid or a dipeptide

The hydrochloride salt of 40 (1 eq.) was treated with a Boc-protected amino acid or a peptide succinimidyl ester (1.05 eq.) in the presence of N-methylmorpholine (NMM) (3 eq.) in THF for 2-12 h at room temperature. The reaction mixture was concentrated to dryness and the crude residue was taken in EtOAc and washed with saturated bicarbonate, ammonium chloride solution and brine. The organic layer was dried over anhydrous sodium sulfate and concentrated to dryness to yield the Boc-protected amino acid or the peptide derivative 41. The Boc-protected derivative 41 was deprotected using 4N HCl/dioxane for 2-3 h at room temperature. The solvent was evaporated to dryness to yield the hydrochloride salt of the amino acid or peptide derivative 42.

In other embodiments, the synthesis of Val-6-aminohexanoate-CH$_2$OCO-MPH (42a) is as follows:

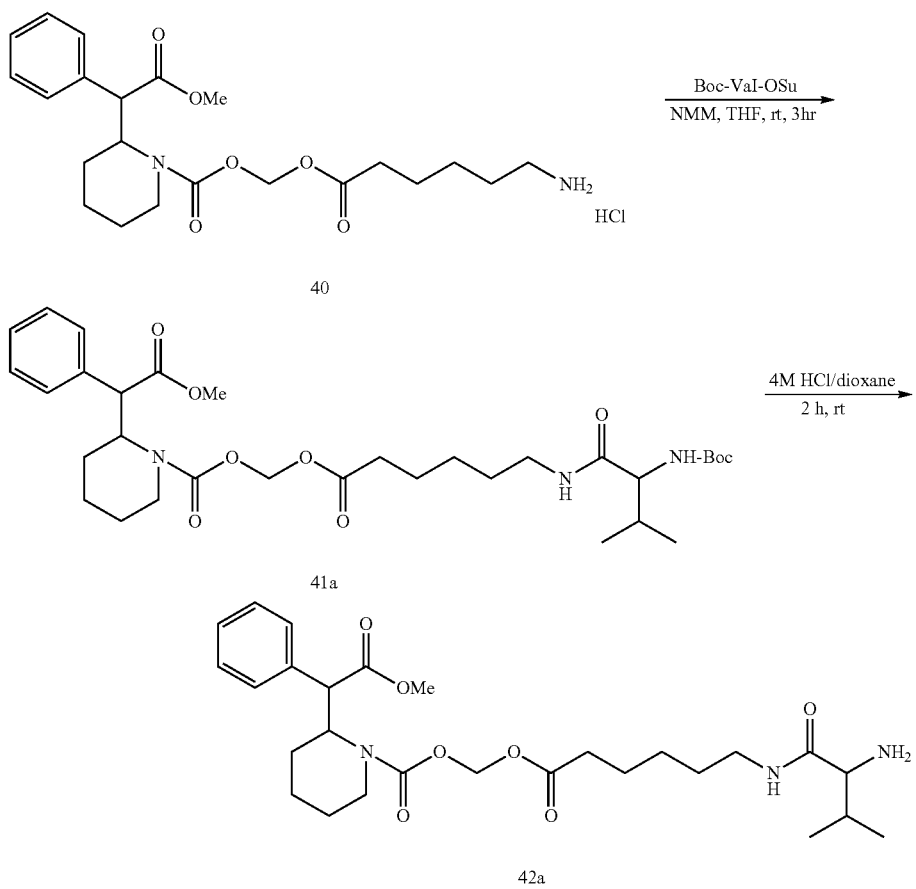

A. Synthesis of Boc-Val-6-aminohexanoate-CH$_2$OCO-MPH (41a)

Compound 40 (0.08 g, 0.175 mmol) was taken in anhydrous THF (10 mL). NMM (0.06 mL, 0.525 mmol) and Boc-protected succinimidyl ester (0.06 g, 0.184 mmol) were added and the reaction mixture was stirred for 2 h at room temperature. Solvent was concentrated to dryness and crude product was taken in ethyl acetate (100 mL), washed once each with saturated bicarbonate (40 mL), ammonium chloride solution (40 mL) and brine (40 mL). The organic layer was dried over anhydrous sodium sulfate and concentrated to dryness to yield 41a (0.084 g) (yield, 77%).

B. Synthesis of Val-6-aminohexanoate-CH₂OCO-MPH (42a)

Compound 41a (0.084 g, 0.14 mmol) was dissolved in 4N HCl/dioxane (4-5 mL) and stirred at room temperature for 2 h. Dioxane was concentrated to dryness to yield 42a (0.078 g) (yield, 100%).

In other embodiments, the general procedure for the synthesis of amino acid and peptide conjugates of methylphenidate (44) is as follows:

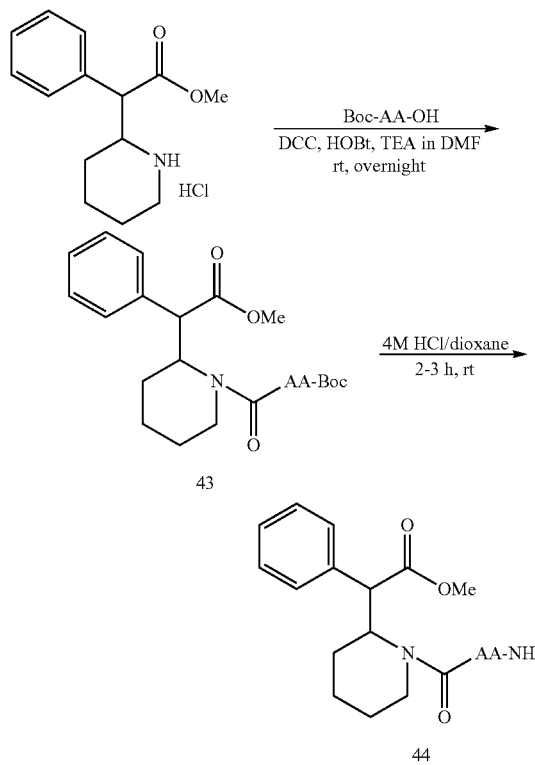

AA = amino acid, dipeptide or tripeptide

Methylphenidate hydrochloride (1 eq.) was taken in anhydrous DMF. Boc-protected amino acid or peptide (1.05 eq.), DCC (1.05 eq.), HOBt (1.1 eq.) and TEA (2.5 eq.) were added. The mixture was stirred overnight at room temperature. DMF was evaporated in vacuum and the residue dissolved in ethyl acetate. The organic layer was washed with 1% sodium bisulfate and brine. The organic layer was concentrated to dryness to yield the Boc-protected conjugate. The Boc group was deprotected by treating with 4N HCl/dioxane for 2-3 h at room temperature. Dioxane was evaporated to dryness to yield the amino acid or peptide derivative of methylphenidate (44).

In some embodiments, the synthesis of Ala-MPH (44a) is as follows:

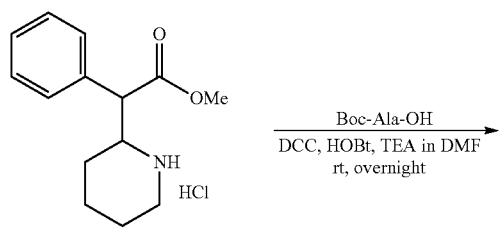

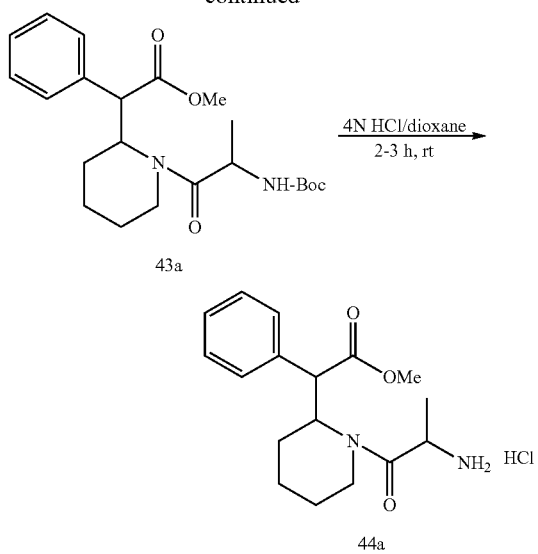

A. Synthesis of Boc-Ala-MPH (43a)

Methylphenidate hydrochloride (0.274 g, 1.02 mmol) was taken in anhydrous DMF (10 mL). Boc-Ala-OH (0.20 g, 1.07 mmol), TEA (0.35 mL, 2.54 mmol), HOBt (0.15 g, 1.11 mmol) and DCC (0.22 g, 1.07 mmol) were added. The reaction mixture was stirred overnight at room temperature. DMF evaporated to dryness and the residue was taken in EtOAc (200 mL), and washed once each with 1% sodium bisulfate (60 mL) and brine (60 mL). The organic layer was dried over anhydrous sodium sulfate and concentrated to dryness to yield 43a (0.37 g) (yield, 90%).

B. Synthesis of Ala-MPH.HCl (44a)

Compound 43a (0.37 g) was taken in 4N HCl/dioxane (8 mL) and stirred for 2 h at room temperature. Dixoane was evaporated to dryness to yield 44a (0.31 g) (yield, 100%).

In other embodiments, the general procedure for the synthesis of 1,3-diglyceride derivatives of methylphenidate with or without linker (chain length of carboxylic acid preferably $C_{14}$ or longer) is as follows:

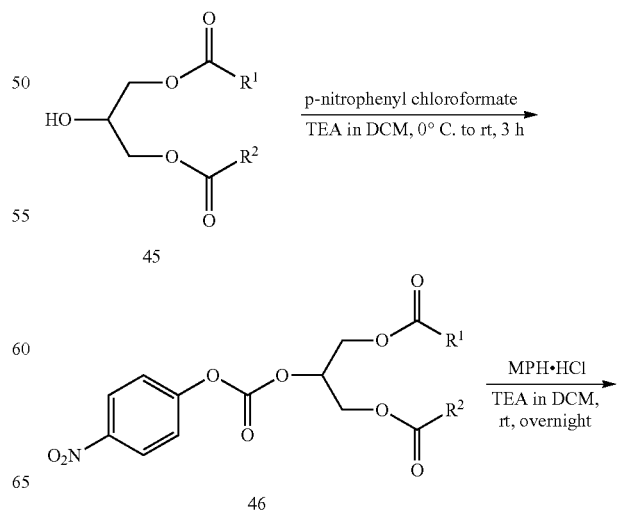

-continued

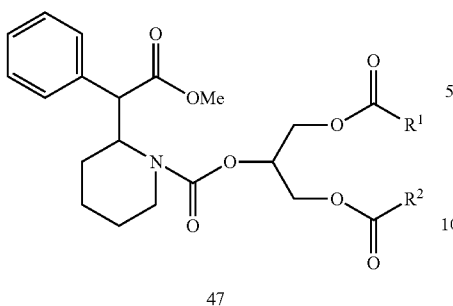

47

R¹, R² = fatty acid chain

The hydroxyl group of 1,3-diglycerides (45) can be activated with p-nitrophenyl chloroformate. The activated 1,3-diglyceride 46 can then be treated with methylphenidate hydrochloride in the presence of TEA in DMF to yield the respective carbamate derivative 47. Examples of 1,3-diglycerides include but are not limited to glyceryl 1,3-dipalmitate, glyceryl 1,3-distearate or 1-palmitoyl-3-stearoyl-glycerol.

In some embodiments, the synthesis of 1,3-diglyceride derivatives of MPH with hydroxycarboxylic acid linkers (48) is as follows:

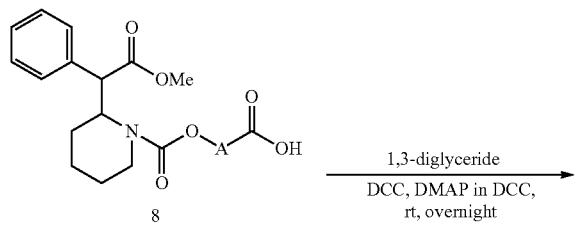

For example:

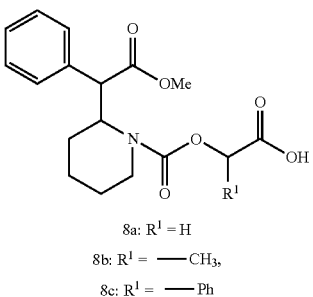

8a: R¹ = H
8b: R¹ = —CH₃,
8c: R¹ = —Ph

-continued

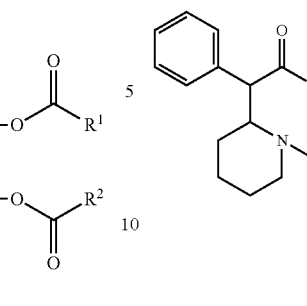

48a: R¹ = H
48b: R¹ = —CH₃,
48c: R¹ = —Ph

R², R³ = fatty acid chain

= L

A carbamate of methylphenidate and a linker with a free terminal carboxylic acid group can also be attached to a 1,3-diglyceride derivative. Methylphenidate carbamate conjugates of hydroxy carboxylic acids, for example, can be coupled to a 1,3-diglyceride using DCC and DMAP in DCM to give the respective fatty acid glycerol derivatives 48. Examples of 1,3-diglycerides include but are not limited to glyceryl 1,3-dipalmitate, glyceryl 1,3-distearate or 1-palmitoyl-3-stearoyl-glycerol.

In other embodiments, the general procedure for the synthesis of conjugates of methylphenidate with —C(O)OCH₂O— linker is as follows:

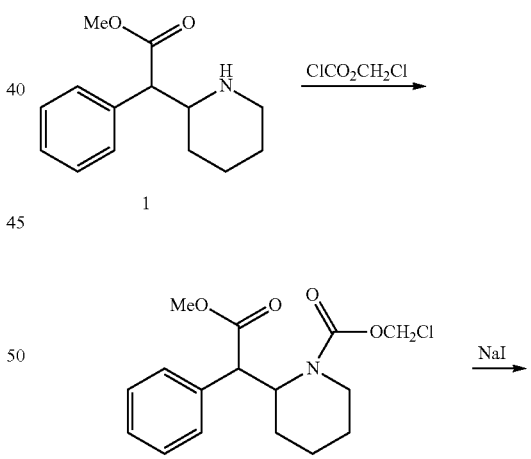

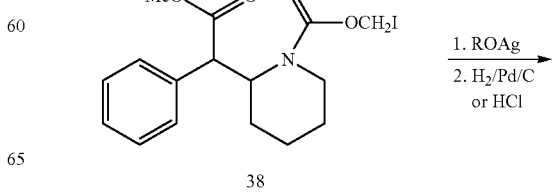

-continued

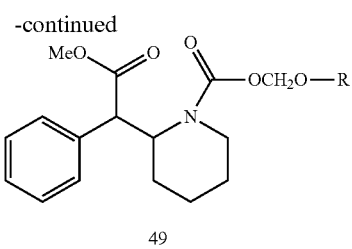

49

R = phosphoryl, acyl

To a solution of iodomethyl carbamate of methylphenidate 38 (1-1.5 mmol) in toluene (25-50 mL) was added silver salt of acid (3 eq.). The mixture was heated from 80° C. to reflux for 3 h depending on the silver salt of the acid. After the reaction was complete, the solid was filter off and the filtrate was concentrated. The residue was purified by column to give the conjugate. The conjugate was either the final product or needed to be deprotected. All protecting groups in these procedures were benzyl groups but others may be used. The conjugate in methanol was hydrogenated with 10% Pd/C using a hydrogen balloon for 2 h. The catalyst was filtered off. The filtrate was concentrated and dried to give the final conjugate 49.

In some embodiments, the synthesis of phosphate-$CH_2OCO$-MPH (49a), the structure of which is shown below, is as follows in steps A, B and C:

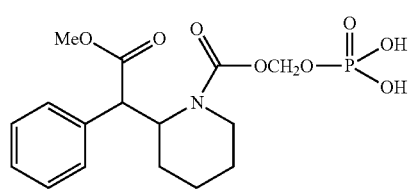

49a

A. Synthesis of Silver Dibenzyl Phosphate

Dibenzyl phosphate (2.78 g, 10 mmol) in water (40 mL) was cooled in an ice bath. Subsequently, 1N NaOH was added while shaking the flask until the pH of solution was about 7. The solid dissolved almost completely. Then silver nitrate (1.89 g, 11 mmol) in water (20 mL) was added slowly. After adding, the resulting solid was collected by filtration and washed with water. The solid was dried in vacuum over phosphorus pentoxide to yield silver dibenzyl phosphate (3.18 g) (yield, 82.5%) as a white solid.

B. Synthesis of (BnO)$_2$-phosphate-$CH_2OCO$-MPH

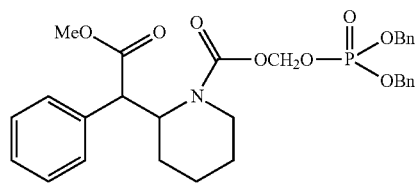

Iodomethyl 2-(2-methoxy-2-oxo-1-phenylethyl)piperidine-1-carboxylate 38 (0.260 g, 0.62 mmol) and silver dibenzyl phosphate (0.719 g, 1.87 mmol) in toluene (20 mL) were refluxed for 1.5 h. The solid was filtered off. The filtrate was concentrated and the residue was purified by silica gel column chomatography (hexanes:EtOAc, 3:1 to 1:1) to give a the protected conjugate (0.27 g) (yield, 76.3%) as colorless oil.

C. Synthesis of phosphate-$CH_2OCO$-MPH (49a)

(Bis(benzyloxy)phosphoryloxy)methyl 2-(2-methoxy-2-oxo-1-phenylethyl)piperidine-1-carboxylate (0.267 g, 0.47 mmol) in methanol (8 mL) was hydrogenated under 10% Pd/C (dry, 90 mg) with a hydrogen balloon for 2 h. The catalyst was filtered off through celite. The filtrate was evaporated to dryness to give 49a (0.136 g) (yield, was 74.6%) as a white amorphous solid.

In some embodiments, the synthesis of nicotinate-$CH_2OCO$-MPH.HCl (49b), the structure of which is shown below, is as follows in steps A and B:

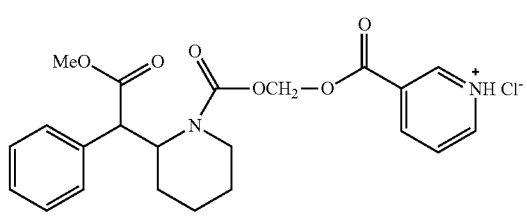

49b

A. Synthesis of nicotinate-$CH_2OCO$-MPH, the structure of which is shown below:

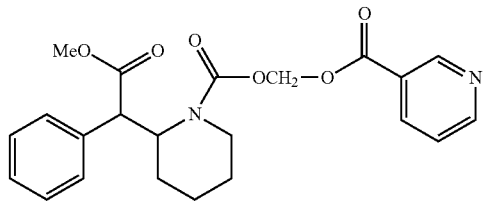

Iodomethyl 2-(2-methoxy-2-oxo-1-phenylethyl)piperidine-1-carboxylate 38 (0.457 g, 1.10 mmol) and silver nicotinate (0.755 g, 3.28 mmol) in toluene (20 mL) were refluxed for 2 h. The solid was filtered off. The filtrate was concentrated and the residue was purified by silica gel column chomatography (hexanes:EtOAc, 2:1 to 1:1) to give 49b in freebase form (0.256 g) (yield, 56.7%) a colorless oil.

B. Synthesis of nicotinate-$CH_2OCO$-MPH.HCl (49b):

(2-(2-methoxy-2-oxo-1-phenylethyl)piperidine-1-carbonyloxy)methyl nicotinate (0.256 g, 0.62 mmol) in acetone (8 mL) was treated with 1.25N HCl/MeOH (0.75 mL, 0.93 mmol). The solvent was evaporated at room temperature. The resulting residue was coevaporated with acetone (2×3 mL) and then dissolved in acetone (0.8 mL) and ether (20 mL) was added. Upon scratching with a spatula, solid formed gradually and was collected by filtration to yield 49b (0.180 g) (yield, 64.6%).

In other embodiments, the synthesis of isonicotinate-$CH_2OCO$-MPH.HCl (49c), the structure of which is shown below, is as follows in steps A and B:

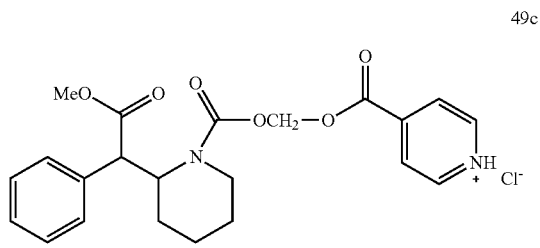

49c

A. Synthesis of isonicotinate-CH₂OCO-MPH, the structure of which is shown below:

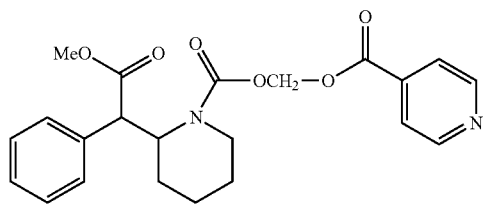

Iodomethyl 2-(2-methoxy-2-oxo-1-phenylethyl)piperidine-1-carboxylate 38 (0.555 g, 1.33 mmol) and silver isonicotinate (0.918 g, 3.99 mmol) in toluene (50 mL) were heated for 1.5 h at 90° C. The solid was filtered off through celite. The filtrate was concentrated and the residue was purified by silica gel column chomatography (hexanes:EtOAc, 1.2:1 to 1:1) to give 49c in freebase form (0.286 g) (yield, 52.1%) as a syrup.

B. Synthesis of isonicotinate-CH₂OCO-MPH.HCl (49c):

(2-(2-methoxy-2-oxo-1-phenylethyl)piperidine-1-carbonyloxy)methyl isonicotinate (0.286 g, 0.62 mmol) in methanol (4 mL) was treated with 1.25N HCl/MeOH (1 mL, 1.25 mmol). The solvent was evaporated at room temperature. The residue was coevaporated with methanol (2×5 mL) and acetone (4 mL) was added. Solid formed gradually and acetone was evaporated. The solid was collected and washed with ether (4×2 mL) to yield 49c (0.228 g) (yield, 73.2%) as an off-white solid.

In other embodiments, the synthesis of palmitate-CH₂OCO-MPH (49d), the structure of which is shown below, is as follows:

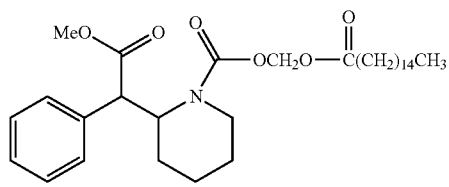

49d

Iodomethyl 2-(2-methoxy-2-oxo-1-phenylethyl)piperidine-1-carboxylate 38 (0.472 g, 1.13 mmol) and silver palmitate (1.233 g, 3.39 mmol) in toluene (50 mL) were heated for 1 h at 95° C. The solid was filtered off. The filtrate was concentrated and the residue was purified by silica gel column chromatography (hexanes:EtOAc, 5:1) to give 49d (0.48 g) (yield, 77.8%) as a white solid.

In some embodiments, the synthesis of gallate-CH₂OCO-MPH (49e), the structure of which is shown below, is as follows:

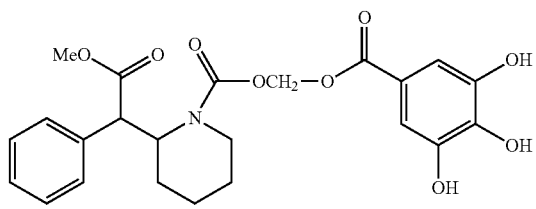

49e

Iodomethyl 2-(2-methoxy-2-oxo-1-phenylethyl)piperidine-1-carboxylate 38 (0.477 g, 1.14 mmol) and silver 3,4,5-tris(benzyloxy)benzoate (1.877 g, 3.43 mmol) in toluene (50 mL) were heated for 1 h at 85° C. The solid was filtered off through celite. The filtrate was concentrated and the residue was purified by silica gel column chomatography (hexanes:EtOAc, 3:1) to give 0.55 g of an amorphous solid, which was hydrogenated under 10% Pd/C (dry, 150 mg) in methanol (25 mL) with a hydrogen balloon for 2 h. The catalyst was filtered off through celite. The filtrate was evaporated to dryness to give 49e (0.315 g) (yield, 60.1%) as an amorphous solid.

In other embodiments, the synthesis of phosphate-(p-salicylate)-CH₂OCO-MPH (49f), the structure of which is shown below, is as follows:

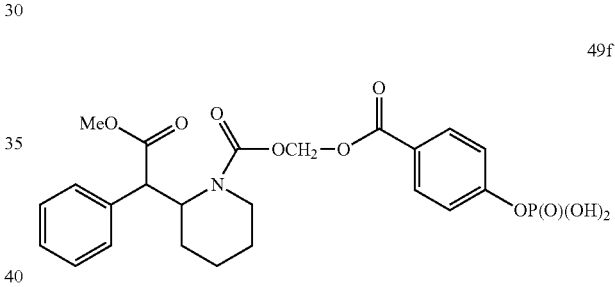

49f

Iodomethyl 2-(2-methoxy-2-oxo-1-phenylethyl)piperidine-1-carboxylate 38 (0.47 g, 1.13 mmol) and silver 4-(bis(benzyloxy)phosphoryloxy)benzoate (1.01 g, 2 mmol) in toluene (50 mL) were heated for 1 h at 90° C. The solid was filtered off through celite. The filtrate was concentrated and the residue was purified by silica gel column chomatography (hexanes:EtOAc, 3:1-2:1) to give 0.45 g of a colorless oil, which was hydrogenated under 10% Pd/C (dry, 100 mg) in methanol (15 mL) with a hydrogen balloon for 1 h. The catalyst was filtered off through celite. The filtrate was evaporated to give 49f (0.326 g) (yield, 56.8%) as an amorphous solid.

In some embodiments, the general procedure for the synthesis of pyridium-type conjugates of methylphenidate is as follows:

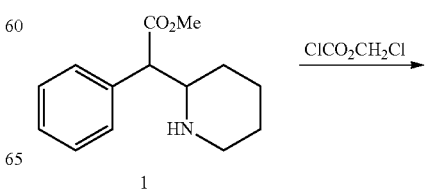

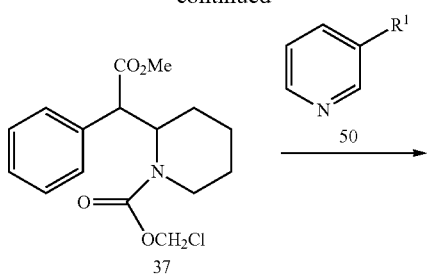

37

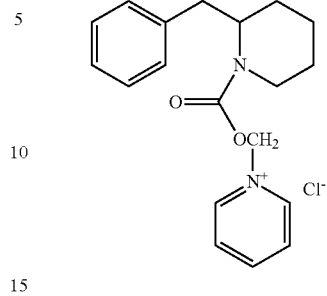

51a

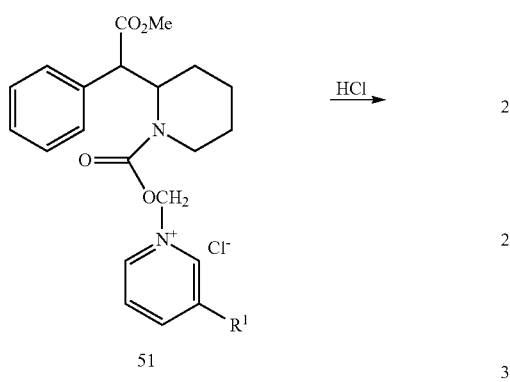

51

$R^1$ = H, —CO$_2$Et, —CONH$_2$, —CO$_2$$^t$Bu, —CO-Gly-Ala-O$^t$Bu,
—CO-Val-O$^t$Bu, —CO-Asp(O$^t$Bu)-O$^t$Bu $R^2$ = —CO-Gly-Ala, —CO-Val, —CO-Asp, —CO$_2$H

The chloromethyl carbamate of methylphenidate 37 (1-1.5 mmol) and pyridine or pyridine derivative 50 (1-7 mmol) in acetonitrile (6-10 mL) were heated for 3.5 h to 48 h at 70° C. After the reaction was complete, the solvent was evaporated. The residue was purified to give the conjugate. The conjugate was either the final product or needed to be deprotected. All the protecting groups for these reactions were tert-butyl groups, which were removed with 4N HCl/dioxane, but other protecting groups may be used.

In other embodiments, the synthesis of MPH-CO$_2$CH$_2$-pyridine chloride (51a), the structure of which is shown below, is as follows:

The chloromethyl carbamate of methylphenidate 37 (0.326 g, 1 mmol) and pyridine (0.566 mL, 7 mmol) in acetonitrile (6 mL) were heated for 3.5 h at 70° C. The solvent was evaporated and then coevaporated with toluene (2×5 mL). The resulting residue was dissolved in DCM (1 mL) and tert-butyl methyl ether (TBME) (15 mL) was added. The milky liquid was decanted. The residue was dried in vacuum to give 51a (0.404 g) (yield, 99.8%) as an amorphous solid.

In other embodiments, the synthesis of MPH-CO$_2$CH$_2$-nicotinoyl-OEt chloride (51 b), the structure of which is shown below, is as follows:

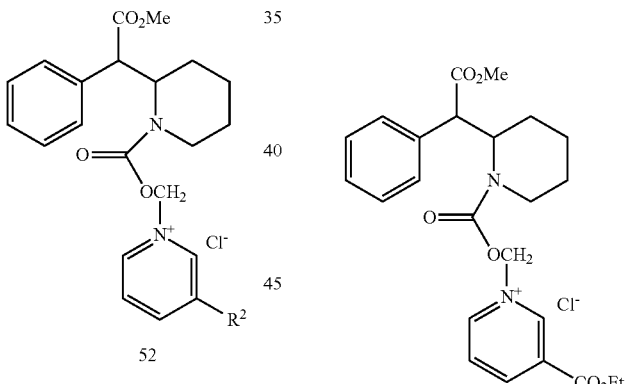

51b

The chloromethyl carbamate of methylphenidate 37 (0.326 g, 1 mmol) and ethyl nicotinate (0.453 g, 3 mmol) in acetonitrile (6 mL) were heated for 24 h at 70° C. The solvent was evaporated. The residue was dissolved in DCM (1.5 mL) and TBME (40 mL) was added. Solid formed and liquid was decanted. The above procedure was repeated twice. The resulting residue was dried in vacuum to give 51b (0.325 g) (yield, 68.1%) as an off-white solid.

In some embodiments, the synthesis of MPH-CO$_2$CH$_2$-nicotinamide chloride (51c), the structure of which is shown below, is as follows:

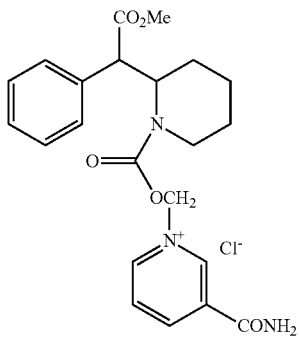

51c

The chloromethyl carbamate of methylphenidate 37 (0.326 g, 1 mmol) and nicotinamide (0.122 g, 1 mmol) in acetonitrile (6 mL) were heated for 26 h at 70° C. The solvent was evaporated and to the resulting residue was added EtOAc (40 mL). Upon scratching with a spatula, solid formed gradually and was collected by filtration. The solid was further washed with EtOAc (3×3 mL) and dried in vacuum to yield 51c (0.298 g) (yield, 66.5%) as an off-white solid.

In some embodiments, the synthesis of MPH-CO₂CH₂-nicotinoyl-O^tBu chloride (51d), the structure of which is shown below, is as follows:

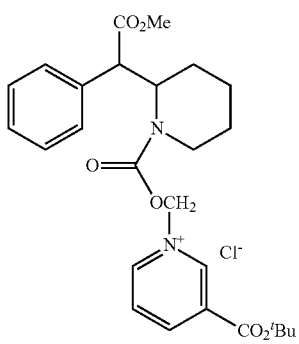

51d

The chloromethyl carbamate of methylphenidate 37 (0.489 g, 1.5 mmol) and tert-butyl nicotinate (0.806 g, 4.5 mmol) in acetonitrile (10 mL) were heated for 7 h at 70° C. The solvent was evaporated. To the residue in DCM (1 mL) was added TBME (40 mL). The liquid was decanted and the residue was dissolved in DCM (1 mL) and then TBME (30 mL) was added. The resulting solid was collected, washed with TBME (3×4 mL) and dried in vacuum to yield 51d (0.325 g) (yield, 47.4%) an off-white solid.

In other embodiments, the synthesis of MPH-CO₂CH₂-nicotinoyl-Gly-Ala chloride (52a), the structure of which is shown below, is as follows in steps A, B and C:

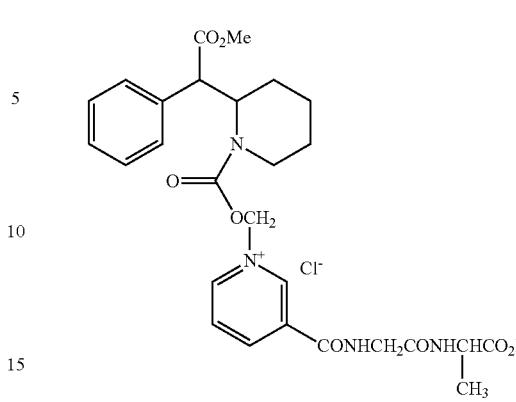

52a

A. Synthesis of tert-butyl 2-(2-(nicotinamido)acetamido)propanoate (50e), the structure of which is shown below:

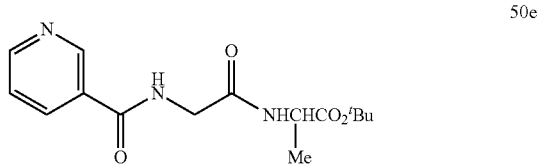

50e

To H-Gly-Ala-O^tBu (0.85 g, 4.2 mmol) in DCM (30 mL) was added Et₃N (1.17 mL, 8.4 mmol). Nicotinoyl chloride hydrochloride (0.748 g, 4.2 mmol) was added in portions (4 times, over 20 min.) in an ice-bath. After adding, the mixture was stirred for 1 h below 5° C. Water (30 mL) was added to quench the reaction, followed by DCM (50 mL). The DCM layer was further washed with 5% NaHCO₃ and brine (30 mL each) and dried over Na₂SO₄. The solvent was evaporated and the residue was purified by silica gel column chomatography (6% MeOH/DCM) to give 50e (0.881 g) (yield, 68.3%) as an amorphous solid.

B. Synthesis of MPH-CO₂CH₂-nicotinoyl-Gly-Ala-O^tBu chloride (51e), the structure of which is shown below:

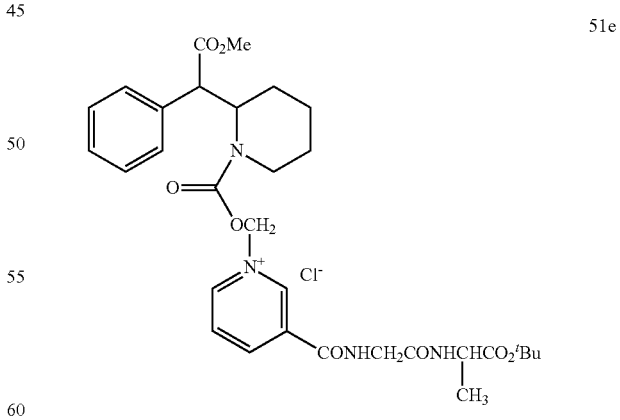

51e

The chloromethyl carbamate of methylphenidate 37 (0.489 g, 1.5 mmol) and tert-butyl 2-(2-(nicotinamido) acetamido)propanoate 50e (0.461 g, 1.5 mmol) in acetonitrile (10 mL) were heated for 24 h at 70° C. The solvent was evaporated. The residue was dissolved in DCM (1.5 mL) and TBME (25 mL) was added. Solid formed and the liquid was decanted. The above procedure was repeated four times. The solid was collected, washed with TBME (3×2 mL) and dried in vacuum to give 51e (0.576 g) (yield, 60.7%) as an off-white solid.

C. Synthesis of MPH-CO₂CH₂-nicotinoyl-Gly-Ala chloride (52a):

To 51e (0.367 g, 0.58 mmol) in DCM (1 mL) was added 4 M HCl/dioxane (5 mL). The mixture was stirred for 2 h. The solvent was evaporated. The residue was dissolved in DCM (2 mL) and TBME (25 mL) was added. The resulting solid was collected, washed with TBME (2×1 mL) and dried in vacuum to yield 52e (0.322 g) (yield, 96.1%) as a solid.

In other embodiments, the synthesis of MPH-CO₂CH₂-nicotinoyl-Val chloride (52b), the structure of which is shown below, is as follows in steps A, B and C:

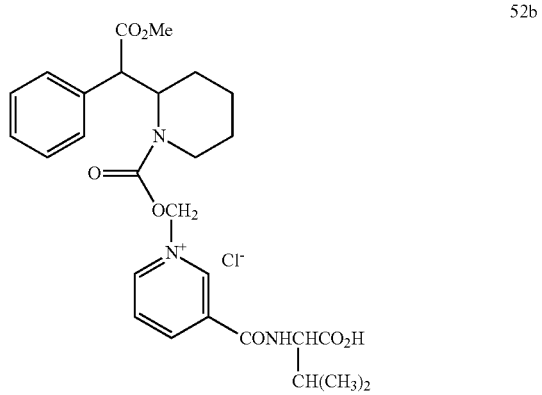

A. Synthesis of tert-butyl 3-methyl-2-(nicotinamido)butanoate (50f), the structure of which is shown below:

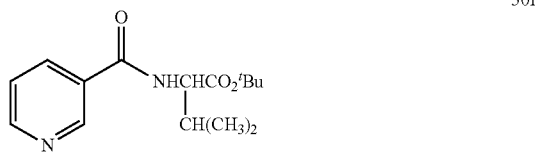

50f was prepared by the same procedure as 50e and was purified by silica gel column chomatography (3% MeOH/DCM) to give 50f (0.882 g, 3 mmol scale) (yield, 98.4%) as a syrup.

B. Synthesis of MPH-CO₂CH₂-nicotinoyl-Val-OᵗBu chloride (51f), the structure of which is shown below:

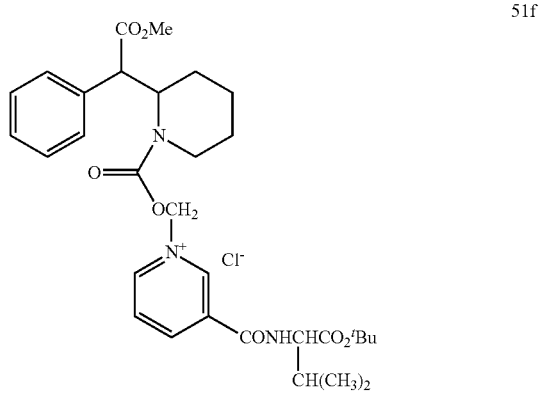

The chloromethyl carbamate of methylphenidate 37 (0.489 g, 1.5 mmol) and tert-butyl 3-methyl-2-(nicotinamido)butanoate 50f (0.278 g, 1 mmol) in acetonitrile (10 mL) were heated for 40 h at 70° C. The solvent was evaporated. To the residue in TBME (5 mL) was added hexanes (10 mL). The resulting solid was collected, washed with TBME/hexanes (1:1, 6×3 mL) and dried in vacuum to give 51f (0.464 g) (yield, 76.8%).

C. Synthesis of MPH-CO₂CH₂-nicotinoyl-Val chloride (52b):

To 51f (0.302 g, 0.5 mmol) in DCM (1 mL) was added 4N HCl/dioxane (5 mL). The mixture was stirred for 5 h. The solvent was evaporated. The residue was dissolved in DCM (1.5 mL) and TBME (25 mL) was added. The resulting solid was collected, washed with TBME (4×2 mL) and dried in vacuum to give 52b (0.329 g) (yield, 100%) as a solid.

In other embodiments, the synthesis of MPH-CO₂CH₂-nicotinoyl-Gly-Asp chloride (52c), the structure of which is shown below, is as follows in steps A, B and C:

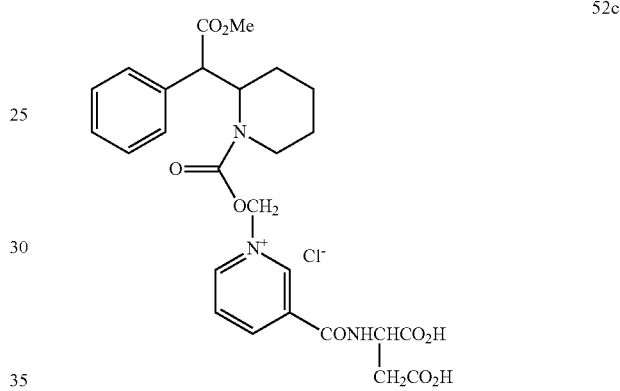

A. Synthesis of di-tert-butyl 2-(nicotinamido)succinate (50g), the structure of which is shown below:

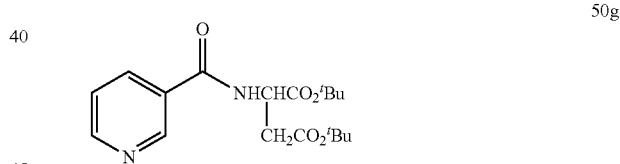

50g was prepared by the same procedure as 50e.

B. Synthesis of MPH-CO₂CH₂-nicotinoyl-Asp(OᵗBu)-OᵗBu chloride (51g), the structure of which is shown below:

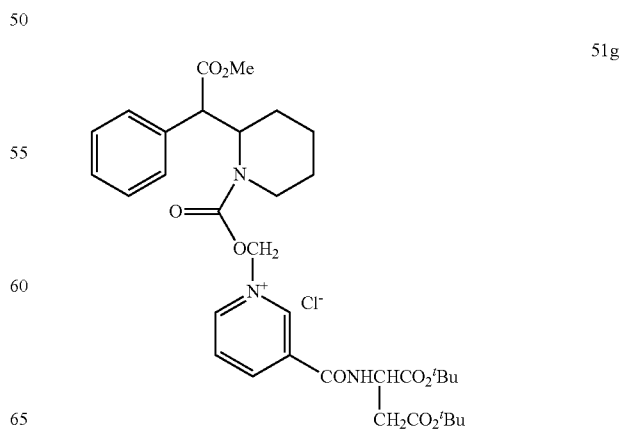

The chloromethyl carbamate of methylphenidate 37 (0.489 g, 1.5 mmol) and di-tert-Butyl 2-(nicotinamido) succinate 50g (0.35 g, 1 mmol) in acetonitrile (10 mL) were heated for 24 h at 70° C. The solvent was evaporated. The residue was purified by silica gel column chomatography (7% MeOH/DCM, then 11% MeOH/DCM) to give 51g (0.452 g) (yield, 66.8%) as an amorphous solid.

C. Synthesis of MPH-CO$_2$CH$_2$-nicotinoyl-Asp chloride (52c):

51g (0.45 g, 0.67 mmol) in 4N HCl/dioxane (5 mL) was stirred for 3 h. The solvent was evaporated. The residue was coevaporated with DCM (4×5 mL), then dissolved in DCM (4 mL) and TBME (25 mL) was added. The resulting solid was collected, washed with TBME (4×2 mL) and dried in vacuum to yield 52c (0.357 g) (yield, 95.1%) as a solid.

In other embodiments, the synthesis of MPH-CO$_2$CH$_2$-nicotinate chloride (52d), the structure of which is shown below, is as follows:

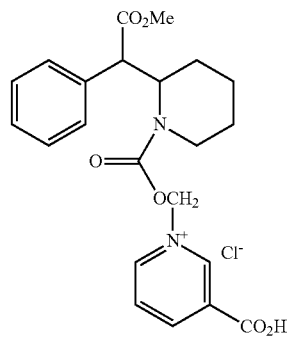

3-(tert-Butoxycarbonyl)-1-((2-(2-methoxy-2-oxo-1-phenylethyl)piperidine-1-carbonyloxy)methyl)pyridium chloride 51d (0.202 g, 0.4 mmol) in 4N HCl/dioxane (5 mL) was stirred for 24 h. The solvent was evaporated. The residue was dissolved in DCM (1 mL) and TBME (20 mL) was added. The resulting solid was collected, washed with TBME (3×1 mL) and dried in vacuum to give 52d (0.172 g) (yield, 95.8%) as a solid.

In some embodiments, the synthesis of phosphate-(p-salicylate)-MPH (56), the structure of which is shown below, is as follows in steps A, B, C and D:

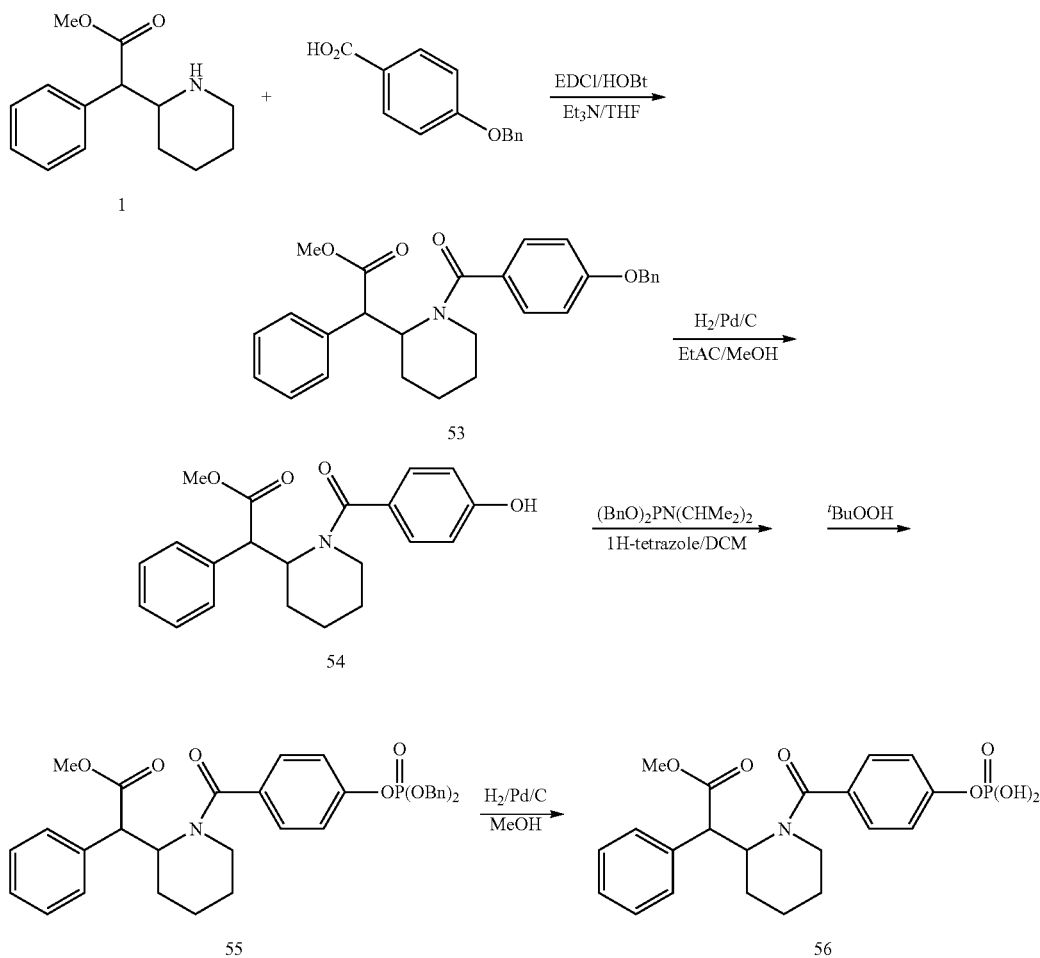

A. Synthesis of BnO-p-salicylate-MPH (53), the structure of which is shown below:

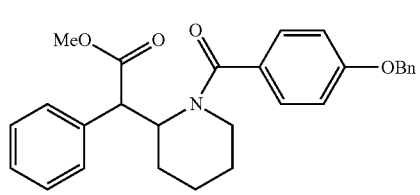

Methylphenidate hydrochloride (2.698 g, 10 mmol), 4-benzyloxybenzoic acid (2.282 g, 10 mmol) and HOBt.H$_2$O (1.532 g, 10 mmol) in THF (60 mL) were added to Et$_3$N (3.07 mL, 22 mmol), followed by 1-ethyl-3-(3-dimethylaminopropyl) carbodiimide) hydrochloride (EDCl) (2.109 g, 11 mmol). The mixture was stirred for 4 days. EtOAc (200 mL) was added and the mixture was washed with water (30 mL), 5% HOAc (50 mL) and brine (40 mL). The EtOAc layer was dried over Na$_2$SO$_4$. The solvent was evaporated and the residue was crystallized from EtOAc (12 mL). The solid was collected by filtration and washed with cold EtOAc (3×4 mL) to give 53 (3.48 g) (yield, 78.5%) as a white solid.

B. Synthesis of p-salicylate-MPH (54), the structure of which is shown below:

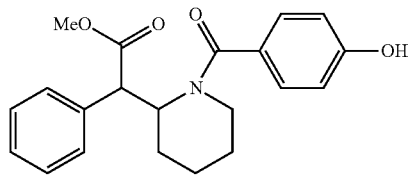

53 (3.48 g, 7.85 mmol) was hydrogenated under 10% Pd/C (wet, 700 mg) in MeOH (10 mL) and EtOAc (100 mL) with a hydrogen balloon for 15 h. The catalyst was filtered off through celite. The filtrate was evaporated to give 54 (2.94 g) as an amorphous solid.

C. Synthesis of (BnO)$_2$-phosphate-(p-salicylate)-MPH (55), the structure of which is shown below:

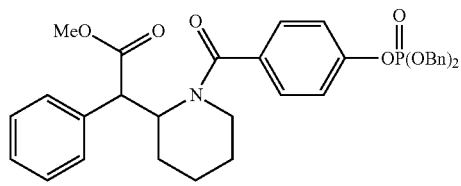

To 54 (0.7 g, 1.98 mmol) in DCM (20 mL) was added dibenzyl diisopropylphosphoramidite (0.752 g, 2.178 mmol), followed by 1N-tetrazole solution in acetonitrile (0.45 M, 4.84 mL, 2.178 mmol). The mixture was stirred for 3 h. Subsequently, 0.6 mL of 70% tert-BuOOH/water was added and stirred for 20 min. The solvent was evaporated. The residue in EtOAc (100 mL) was washed with water and brine (30 mL each) and dried over Na$_2$SO$_4$. The solvent was evaporated and the residue was purified by silica gel column chomatography (EtOAc:hexanes, 1.2:1) to give 55 (0.99 g) (yield, 81.5%) as a syrup.

D. Synthesis of phosphate-(p-salicylate)-MPH (56), the structure of which is shown below:

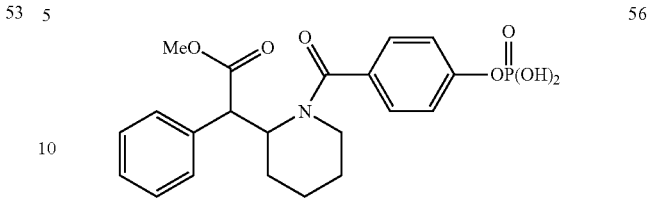

55 (0.99 g, 1.61 mmol) was hydrogenated under 10% Pd/C (wet, 300 mg) in methanol (20 mL) with a hydrogen balloon for 3 h. The catalyst was filtered off through celite. The filtrate was evaporated to give 56 (0.675 g) (yield, 96.5%) as an amorphous solid.

In some embodiments, the synthesis of Gly-(p-salicylate)-MPH (58) is as follows in steps A and B:

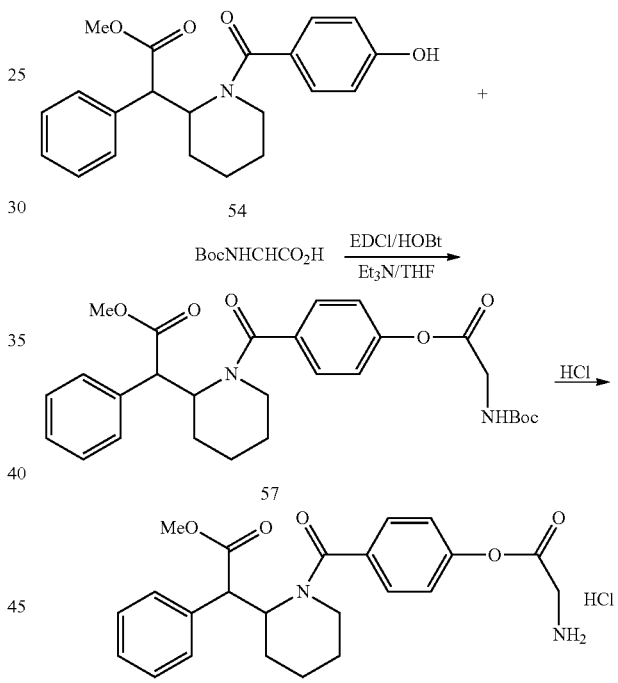

A. Synthesis of Boc-Gly-(p-salicylate)-MPH (57), the structure of which is shown below:

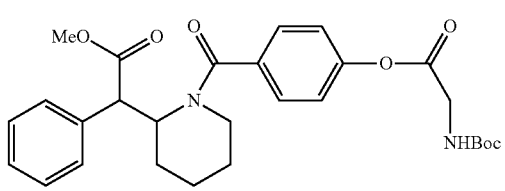

To 54 (0.353 g, 1 mmol), Boc-Gly-OH (0.175 g, 1 mmol) and HOBt.H$_2$O (0.153 g, 1 mmol) in THF (10 mL) were added Et$_3$N (0.15 mL, 1.1 mmol), followed by EDCl (0.211 g, 11 mmol). The mixture was stirred for 15 h. Then another 0.4 mmol of Boc-Gly-OH and EDCl were added and the mixture was again stirred for 3 h. EtOAc (100 mL) was added and the mixture was washed with water (2×30 mL) and brine (30 mL). The EtOAc layer was dried over $Na_2SO_4$. The solvent was evaporated and the residue was purified by silica gel column chomatography (2% MeOH/DCM) to give 57 (0.452 g) (yield, 88.5%) as an amorphous solid.

B. Synthesis of Gly-(p-salicylate)-MPH (58):

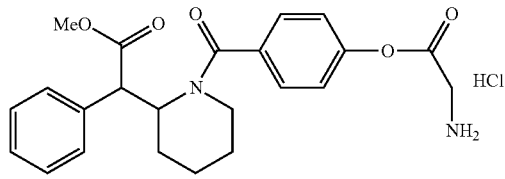

58

To 57 (0.45 g, 0.88 mmol) in DCM (1 mL) was added 4 M HCl/dioxane (5 mL). The mixture was stirred for 1 h. The solvent was evaporated. The residue was coevaporated with DCM (3×5 mL) and then dissolved in DCM (2 mL). EtOAc (10 mL) and TBME (10 mL) were added. The resulting solid was collected, washed with EtOAc/TBME (1:1, 3×2 mL) and dried in vacuum to give 58 (0.329 g) (yield, 83.5%) as an white solid.

Pharmaceutical Kits

In some embodiments, the present technology provides pharmaceutical kits comprising a prodrug or composition of the present technology that has increased water solubility than compared to the unconjugated methylphenidate. In some embodiments, a specific amount of individual doses in a package contain a pharmaceutically effective amount of the prodrugs or conjugate of the present technology. In some other embodiments, the kit comprises oral thin films or strips comprising prodrugs or conjugates of the present technology. The present technology provides pharmaceutical kits for the treatment or prevention of ADHD, ADD or drug withdrawal symptoms in a patient. The patient may be a human or animal patient. Suitable human patients include pediatric patients, geriatric (elderly) patients, and normative patients. The kit comprises a specific amount of the individual doses in a package containing a pharmaceutically effective amount of at least one conjugate of methylphenidate of the present technology. The kit can further include instructions for use of the kit. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, about 1, about 2, about 5, about 10 and multiplied factors thereof, (e.g., about ×1, about ×2, about ×2.5, about ×5, about ×10, about ×100, etc).

The presently described technology and its advantages will be better understood by reference to the following examples. These examples are provided to describe specific embodiments of the present technology. By providing these specific examples, it is not intended limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1

Comparison of Oral Pharmacokinetic (PK) Profiles of Conjugates of Methylphenidate and Oxoacids Exemplary prodrug conjugates of the present technology were synthesized as described above. The oral plasma concentrations of methylphenidate released from nicotinate-$CH_2OCO$-MPH, phosphate-$CH_2OCO$-MPH, gallate-$CH_2OCO$-MPH, lactate-$CH_2OCO$-MPH, MPH-$CO_2CH_2$-nicotinoyl-Asp, MPH-$CO_2CH_2$-nicotinoyl-Val, MPH-$CO_2CH_2$-nicotinoyl-Gly-Ala, Val-6-aminohexanoate-$CH_2OCO$-MPH, MPH-$CO_2CH_2$-nicotinamide, 6-aminohexanoate-$CH_2OCO$-MPH, MPH-$CO_2CH_2$-nicotinoyl-O$^t$Bu, MPH-$CO_2CH_2$-nicotinate, MPH-$CO_2CH_2$-nicotinoyl-OEL MPH-$CO_2CH_2$-pyridine, isonicotinate-$CH_2OCO$-MPH and phosphate-(p-salicylate)-$CH_2OCO$-MPH were compared with unconjugated methylphenidate after oral administration in rats. Rats were dosed with oral solutions of the conjugated prodrugs in an amount equivalent to 2 mg/kg of methylphenidate free base and compared to an equimolar solution of unconjugated methylphenidate hydrochloride.

The plasma concentrations of methylphenidate were measured by LC-MS/MS over time. FIGS. 13-30 demonstrate the different PK curves achieved by the different methylphenidate conjugates as compared with unconjugated forms and all of the specific pharmacokinetic parameter data is presented in Tables 2-4. The release of methylphenidate from the prodrugs varied depending on the linker and oxoacids attached to methylphenidate. Changes in the amount of methylphenidate released from the prodrugs as measured by the area under the curve ranged from 0-185%-AUC compared to unconjugated methylphenidate hydrochloride.

Figure 10:
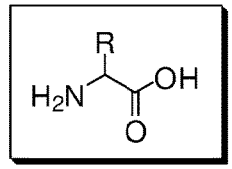
FIG. 10. Chemical structures of some standard amino acids for use in the making of the conjugates of the present technology.
Figure 13:
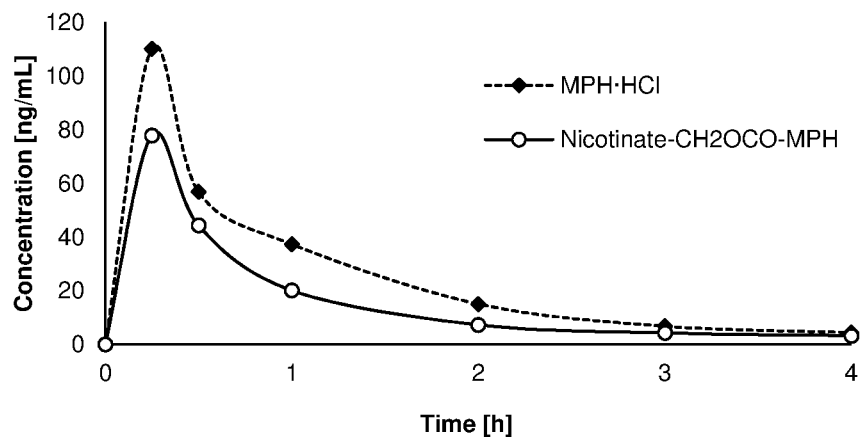
FIG. 13. Oral PK curves comparing the nicotinate-$CH_2OCO$-MPH conjugate with unconjugated methylphenidate in rats.
Figure 14:
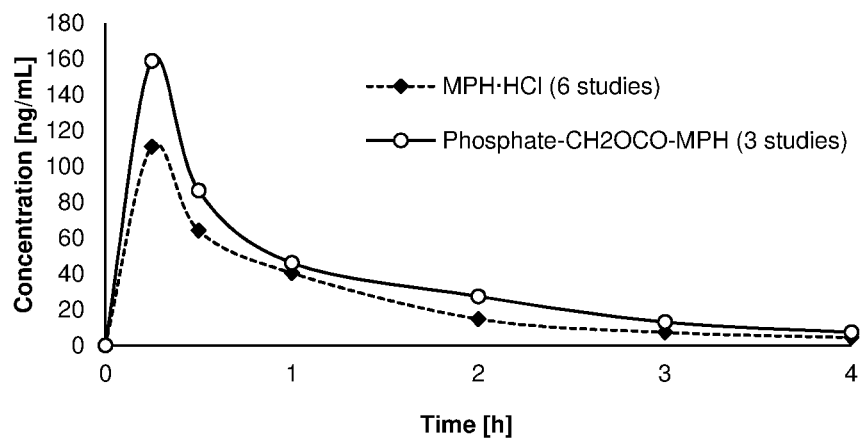
FIG. 14. Oral PK curves comparing the phosphate-$CH_2OCO$-MPH conjugate (data combined from three studies) with unconjugated methylphenidate in rats (data combined from six studies).
Figure 15:
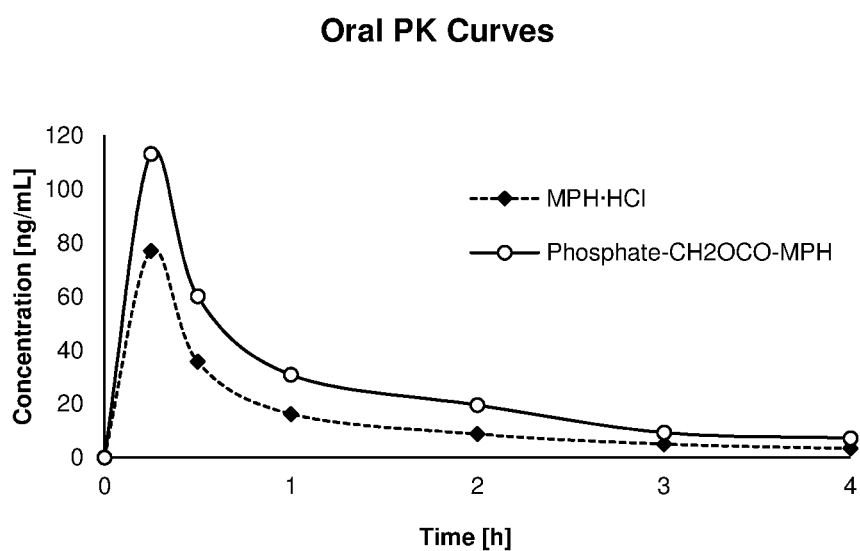
FIG. 15. Oral PK curves comparing the phosphate-$CH_2OCO$-MPH conjugate with unconjugated methylphenidate in rats.
Figure 16:
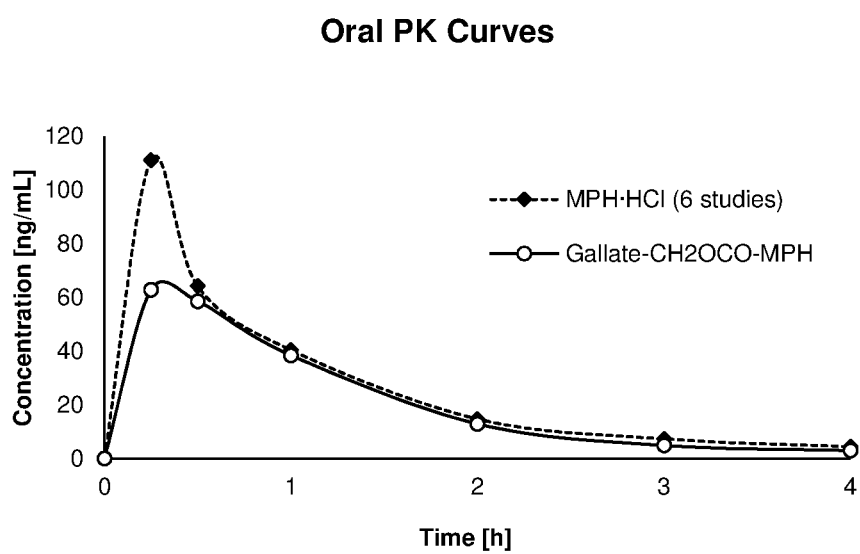
FIG. 16. Oral PK curves comparing the gallate-$CH_2OCO$-MPH conjugate with unconjugated methylphenidate (data combined from six studies) in rats.
Figure 17:
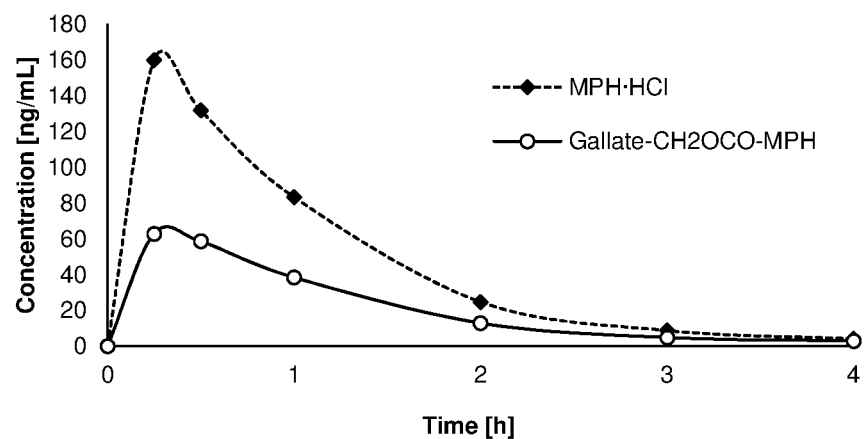
FIG. 17. Oral PK curves comparing the gallate-$CH_2OCO$-MPH conjugate with unconjugated methylphenidate in rats.
Figure 18:
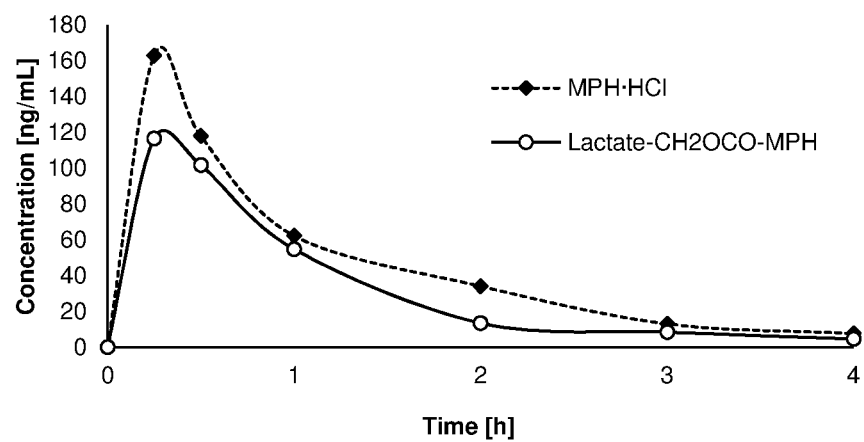
FIG. 18. Oral PK curves comparing the lactate-$CH_2OCO$-MPH conjugate with unconjugated methylphenidate in rats.
Figure 19:
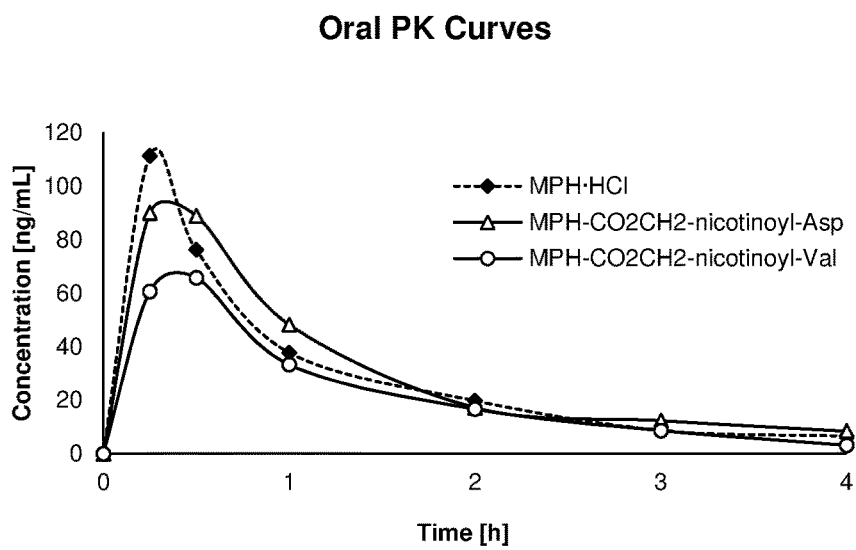
FIG. 19. Oral PK curves comparing the MPH-$CO_2CH_2$-nicotinoyl-Asp and MPH-$CO_2CH_2$-nicotinoyl-Val conjugates with unconjugated methylphenidate in rats.
Figure 20:
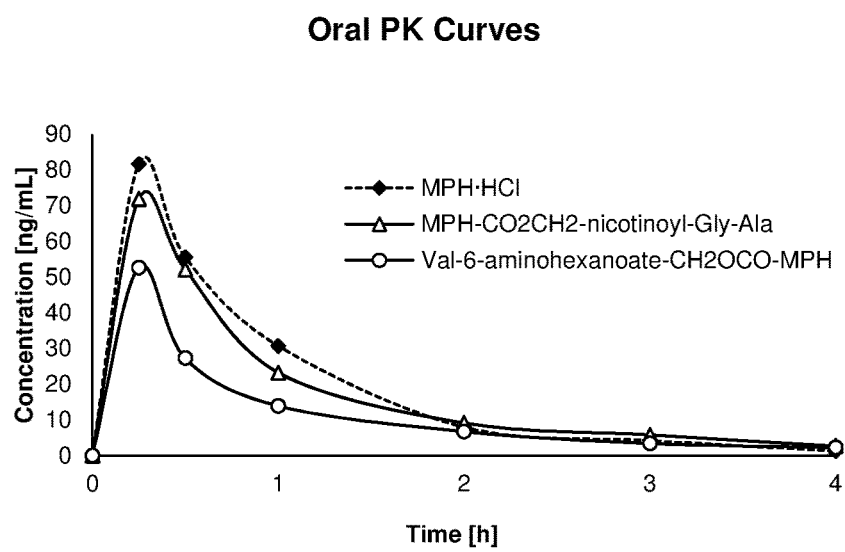
FIG. 20. Oral PK curves comparing the MPH-$CO_2CH_2$-nicotinoyl-Gly-Ala and Val-6-aminohexanoate-$CH_2OCO$-MPH conjugates with unconjugated methylphenidate in rats.
Figure 21:
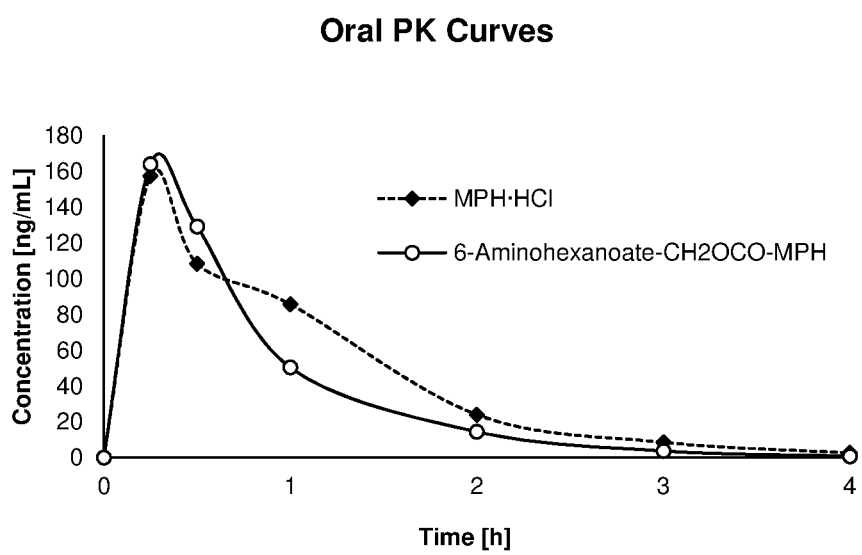
FIG. 21. Oral PK curves comparing the 6-aminohexanoate-$CH_2OCO$-MPH conjugate with unconjugated methylphenidate in rats.
Figure 22:
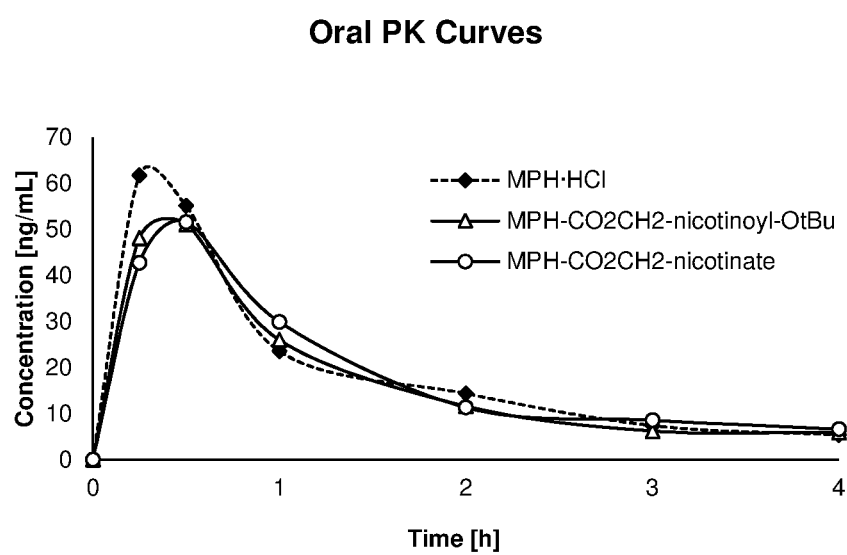
FIG. 22. Oral PK curves comparing the MPH-$CO_2CH_2$-nicotinoyl-O$^t$Bu and MPH-$CO_2CH_2$-nicotinate conjugates with unconjugated methylphenidate in rats.
Figure 23:
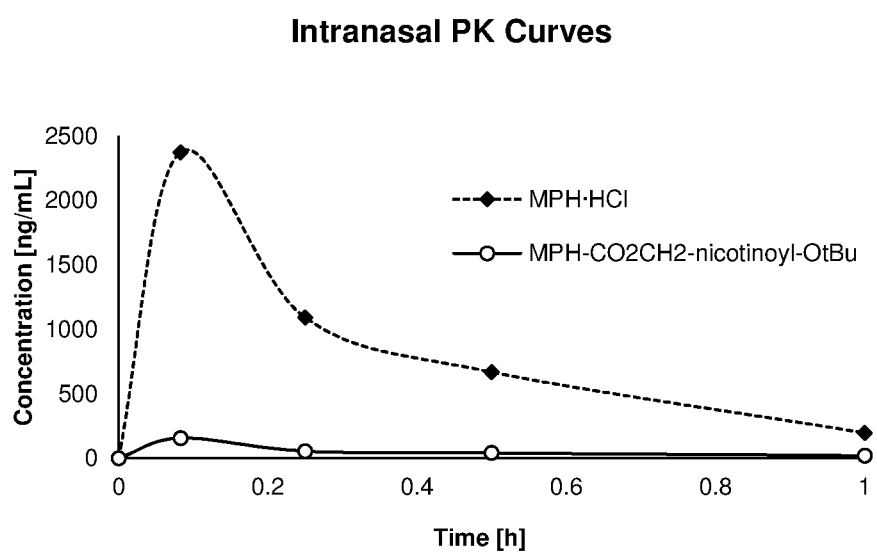
FIG. 23. Intranasal PK curves comparing the MPH-$CO_2CH_2$-nicotinoyl-O$^t$Bu conjugate with unconjugated methylphenidate in rats.
Figure 24:
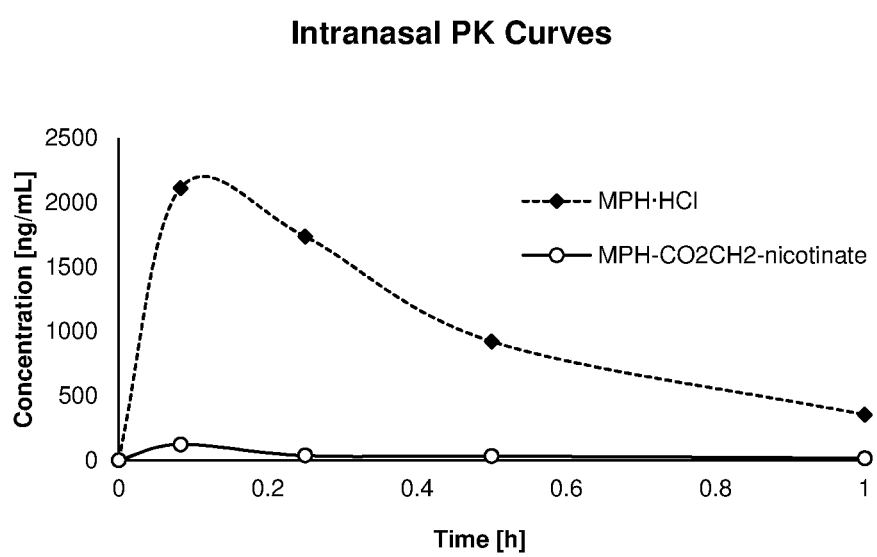
FIG. 24. Intranasal PK curves comparing the MPH-$CO_2CH_2$-nicotinate conjugate with unconjugated methylphenidate in rats.
Figure 25:
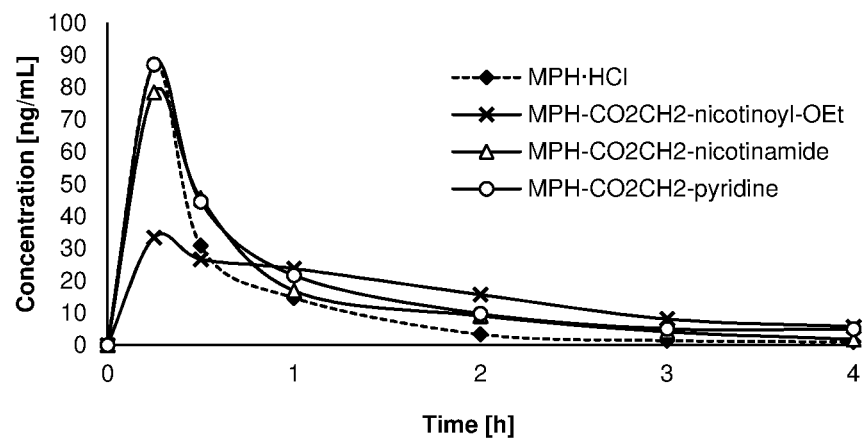
FIG. 25. Oral PK curves comparing the MPH-$CO_2CH_2$-nicotinoyl-OEt, MPH-$CO_2CH_2$-nicotinamide and MPH-$CO_2CH_2$-pyridine conjugates with unconjugated methylphenidate in rats.
Figure 26:
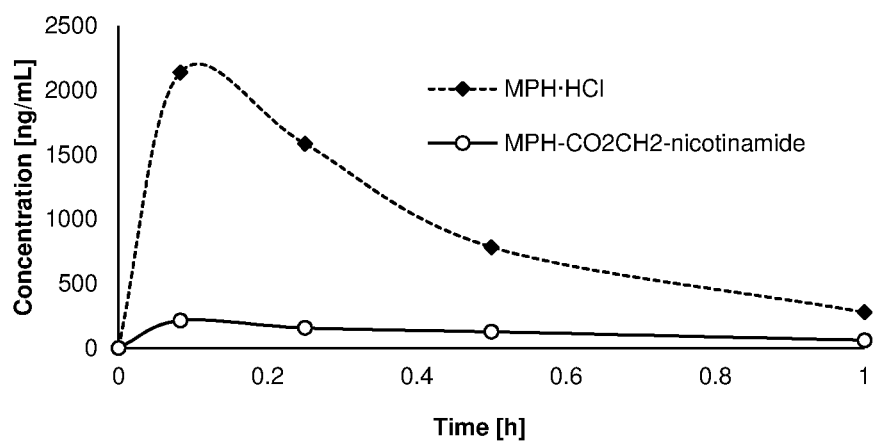
FIG. 26. Intranasal PK curves comparing the MPH-$CO_2CH_2$-nicotinamide conjugate with unconjugated methylphenidate in rats.
Figure 27:
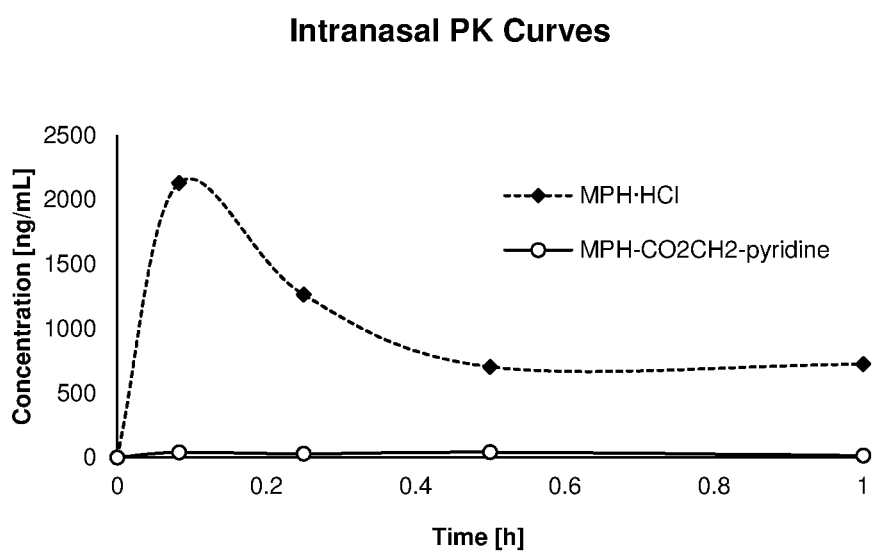
FIG. 27. Intranasal PK curves comparing the MPH-$CO_2CH_2$-pyridine conjugate with unconjugated methylphenidate in rats.
Figure 28:
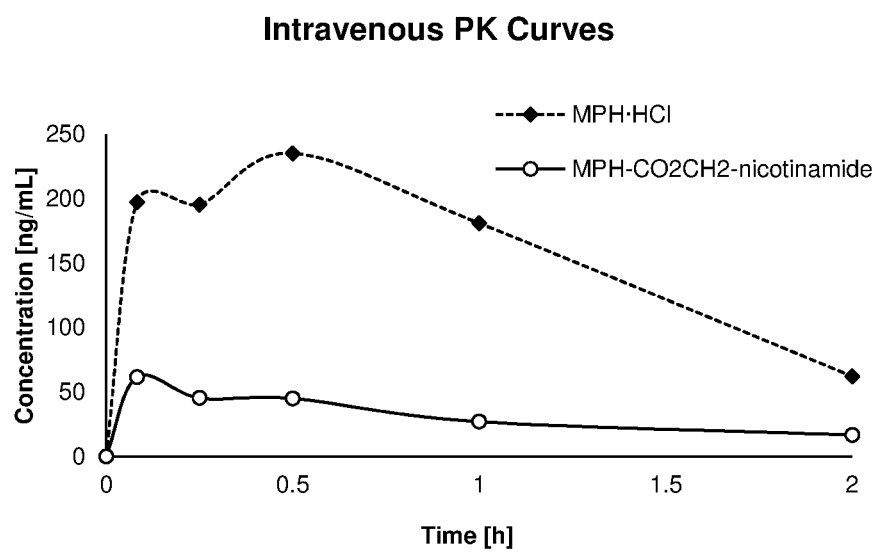
FIG. 28. Intravenous PK curves comparing the MPH-$CO_2CH_2$-nicotinamide conjugate with unconjugated methylphenidate in rats.
Figure 29:
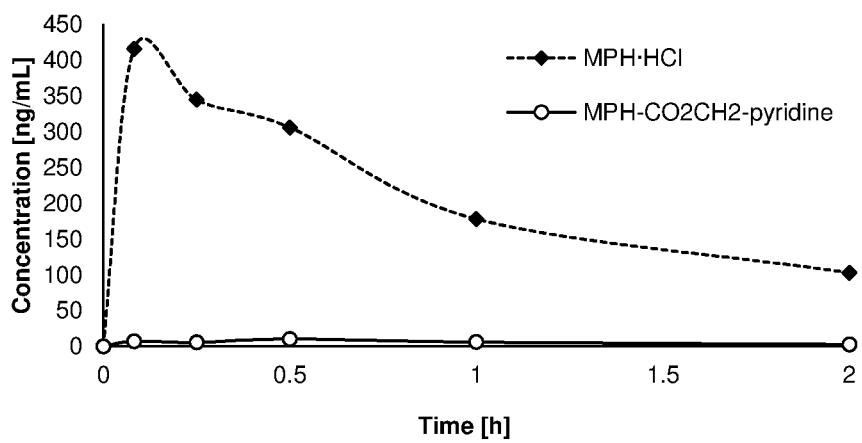
FIG. 29. Intravenous PK curves comparing the MPH-$CO_2CH_2$-pyridine conjugate with unconjugated methylphenidate in rats.
Figure 30:
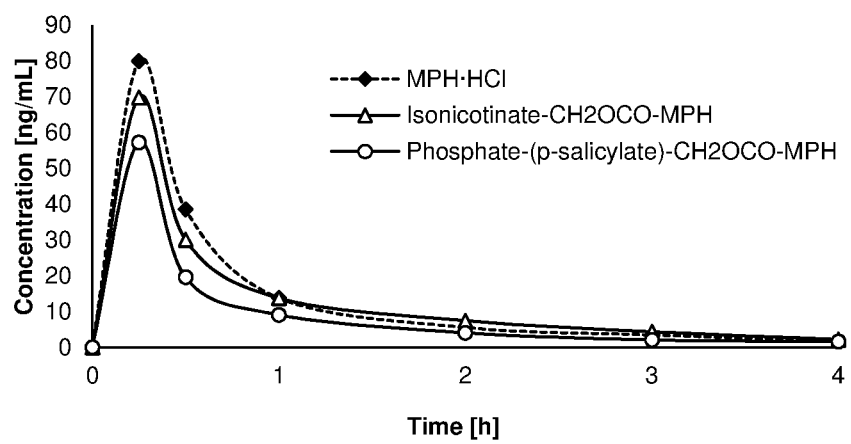
FIG. 30. Oral PK curves comparing the isonicotinate-$CH_2OCO$-MPH and phosphate-(p-salicylate)-$CH_2OCO$-MPH conjugates with unconjugated methylphenidate in rats.

The dosing vehicles for the PK experiments are as follows: FIG. 13—10% Tween in water. FIGS. 14 and 15—water. FIG. 16—conjugate in 50% PEG-400 in water; control: water. FIG. 17—50% PEG-400 in water. FIG. 18—10% Tween in water. FIGS. 19-27—water. FIGS. 28 and 29—phosphate buffered saline (PBS). FIG. 30—10% Tween in water.

TABLE 2

PK parameters for prodrugs of methylphenidate dosed via oral gavage in rats.

| | | | | Methylphenidate | | | | | |
| --- | --- | --- | --- | --- | --- | --- | --- | --- | --- |
| Conjugate | $AUC_{0-4 h}$ [ng/mL × h] | $C_{max}$ [ng/mL] | $T_{max}$ [h] | $AUC_{0-4 h}$ [ng/mL × h] | $C_{max}$ [ng/mL] | $T_{max}$ [h] | AUC-% | $C_{max}$-% | $T_{max}$-% |
| Nicotinate-CH$_2$OCO-MPH (PO) | 64.3 | 83.8 | 0.300 | 93.0 | 110.1 | 0.250 | 69% | 76% | 120% |
| Phosphate-CH$_2$OCO-MPH (PO)[a] | 154.5 | 158.9 | 0.250 | 106.1 | 113.8 | 0.283 | 146% | 140% | 88% |
| Phosphate-CH$_2$OCO-MPH (PO) | 110.8 | 110.8 | 0.250 | 59.8 | 77.0 | 0.250 | 185% | 144% | 100% |
| Gallate-CH$_2$OCO-MPH (PO)[b] | 85.6 | 77.3 | 0.600 | 106.1 | 113.8 | 0.283 | 81% | 68% | 212% |
| Gallate-CH$_2$OCO-MPH (PO) | 85.6 | 77.3 | 0.600 | 187.2 | 176.8 | 0.450 | 46% | 44% | 133% |
| Lactate-CH$_2$OCO-MPH (PO) | 132.3 | 122.5 | 0.300 | 182.3 | 162.8 | 0.250 | 73% | 75% | 120% |
| MPH-CO$_2$CH$_2$-nicotinoyl-Asp (PO) | 125.6 | 97.3 | 0.300 | 116.3 | 111.1 | 0.250 | 108% | 88% | 120% |
| MPH-CO$_2$CH$_2$-nicotinoyl-Val (PO) | 91.4 | 75.2 | 0.350 | 121.6 | 111.1 | 0.250 | 75% | 68% | 140% |
| MPH-CO$_2$CH$_2$-nicotinoyl-Gly-Ala (PO) | 71.0 | 71.8 | 0.250 | 76.9 | 89.6 | 0.300 | 92% | 80% | 83% |
| Val-6-aminohexanoate-CH$_2$OCO-MPH (PO) | 44.9 | 52.7 | 0.250 | 76.9 | 89.6 | 0.300 | 58% | 59% | 83% |
| MPH-CO$_2$CH$_2$-nicotinamide (PO) | 63.4 | 78.6 | 0.300 | 49.5 | 86.8 | 0.250 | 128% | 91% | 120% |
| 6-Aminohexanoate-CH$_2$OCO-MPH (PO) | 145.6 | 173.5 | 0.350 | 177.9 | 159.1 | 0.400 | 82% | 109% | 88% |
| MPH-CO$_2$CH$_2$-nicotinoyl-O$^t$Bu (PO) | 71.4 | 54.9 | 0.400 | 78.1 | 73.9 | 0.300 | 91% | 74% | 133% |
| MPH-CO$_2$CH$_2$-nicotinate (PO) | 75.5 | 52.6 | 0.450 | 78.1 | 73.9 | 0.300 | 97% | 71% | 150% |
| MPH-CO$_2$CH$_2$-nicotinoyl-OEt (PO) | 62.7 | 36.9 | 0.450 | 49.5 | 86.8 | 0.250 | 127% | 43% | 180% |
| MPH-CO$_2$CH$_2$-pyridine (PO) | 720 | 87.1 | 0.250 | 49.5 | 86.8 | 0.250 | 145% | 100% | 100% |
| Isonicotinate-CH$_2$OCO-MPH (PO) | 51.9 | 69.8 | 0.250 | 42.1 | 79.9 | 0.250 | 123% | 87% | 100% |
| Phosphate-(p-salicylate)-CH$_2$OCO-MPH (PO) | 35.3 | 57.1 | 0.250 | 42.1 | 79.9 | 0.250 | 84% | 72% | 100% |

[a]PK parameters for phosphate-CH$_2$OCO-MPH calculated from combined data of three studies and for methylphenidate hydrochloride from combined data of six studies.
[b]PK parameters for gallate-CH$_2$OCO-MPH calculated from data of one study and for methylphenidate hydrochloride from combined data of six studies.

TABLE 3

PK parameters for prodrugs of methylphenidate dosed intranasally in rats.

| | | | | Methylphenidate | | | | | |
| --- | --- | --- | --- | --- | --- | --- | --- | --- | --- |
| Conjugate | $AUC_{0-4 h}$ [ng/mL × h] | $C_{max}$ [ng/mL] | $T_{max}$ [h] | $AUC_{0-4 h}$ [ng/mL × h] | $C_{max}$ [ng/mL] | $T_{max}$ [h] | AUC-% | $C_{max}$-% | $T_{max}$-% |
| MPH-CO$_2$CH$_2$-nicotinamide (IN) | 121.4 | 213.4 | 0.083 | 957.5 | 2137.0 | 0.083 | 13% | 10% | 100% |
| MPH-CO$_2$CH$_2$-nicotinoyl-O$^t$Bu (IN) | 51.6 | 156.3 | 0.083 | 824.0 | 2373.5 | 0.083 | 6% | 7% | 100% |
| MPH-CO$_2$CH$_2$-nicotinate (IN) | 38.8 | 122.0 | 0.083 | 1045.3 | 2210.4 | 0.116 | 4% | 6% | 71% |
| MPH-CO$_2$CH$_2$-pyridine (IN) | 29.2 | 59.9 | 0.187 | 879.2 | 2128.4 | 0.083 | 3% | 3% | 226% |

TABLE 4

PK parameters for prodrugs of methylphenidate dosed intravenously in rats.

| Conjugate | $AUC_{0-4\,h}$ [ng/mL × h] | $C_{max}$ [ng/mL] | $T_{max}$ [h] | Methylphenidate $AUC_{0-4\,h}$ [ng/mL × h] | $C_{max}$ [ng/mL] | $T_{max}$ [h] | AUC-% | $C_{max}$-% | $T_{max}$-% |
|---|---|---|---|---|---|---|---|---|---|
| MPH-CO$_2$CH$_2$-nicotinamide (IV) | 62.5 | 67.3 | 0.633 | 320.2 | 295.8 | 0.517 | 20% | 23% | 123% |
| MPH-CO$_2$CH$_2$-pyridine (IV) | 13.2 | 10.6 | 0.417 | 414.9 | 439.4 | 0.266 | 3% | 2% | 156% |

Example 2

Water Solubility of Methylphenidate Conjugates of the Present Technology

The water solubility of phosphate-CH$_2$OCO-methylphenidate and unconjugated methylphenidate was determined at ambient temperature and the results are found in Table 5.

TABLE 5

Water solubility of methylphenidate conjugates of oxoacids

| Compound | Solubility in Water |
|---|---|
| phosphate-CH$_2$OCO-methylphenidate | 432 mg/mL |
| methylphenidate hydrochloride | 169 mg/mL |

The results for unconjugated methylphenidate hydrochloride are consistent with the solubility data found in the literature (191 mg/mL at 32° C.). The water solubility of the phosphate-CH$_2$OCO-methylphenidate conjugate is about 2.5 times higher than the unconjugated form.

In the present specification, use of the singular includes the plural except where specifically indicated.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

The invention claimed is:

1. A composition comprising at least one conjugate of methylphenidate having a structure selected from the group consisting of

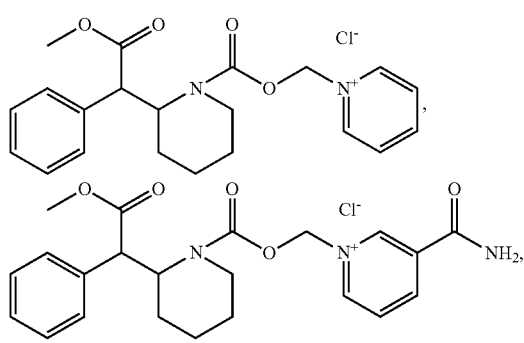

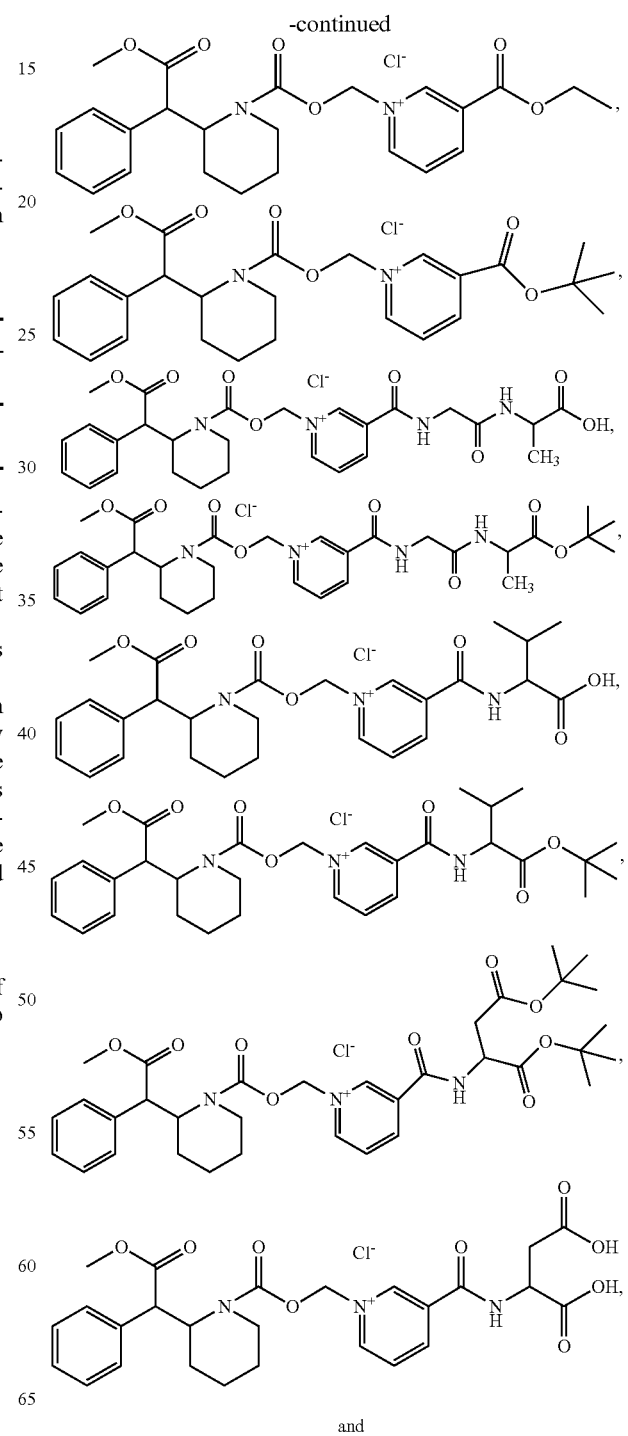

and

-continued

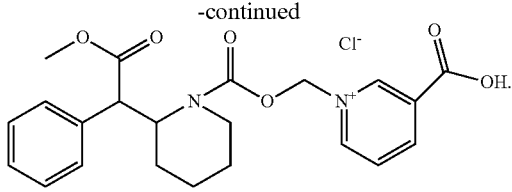

2. The composition of claim 1, wherein the composition is in a form of a gel, a polymorph, a tablet, a capsule, a caplet, a troche, a lozenge, an oral powder, a solution, a thin strip, an oral thin film (OTF), an oral strip, a rectal film, a transdermal patch, a syrup, a suspension, an inhalation compound, or a suppository.

3. The composition of claim 1 for use in a method of treating a patient having a disease, disorder or condition selected from the group consisting of attention-deficit hyperactivity disorder, attention deficit disorder, autistic spectrum disorder, autism, Asperger's disorder, pervasive developmental disorder, sleep disorder, obesity, depression, bipolar disorder, eating disorder, chronic fatigue syndrome, schizophrenia, major depressive disorder, narcolepsy, postural orthostatic tachycardia syndrome, lethargy, and neural insult comprising orally administering to the patient a pharmaceutically effective amount of the composition.

4. The composition of claim 1, wherein the composition is a prodrug.

5. A compound having a structure selected from the group consisting of

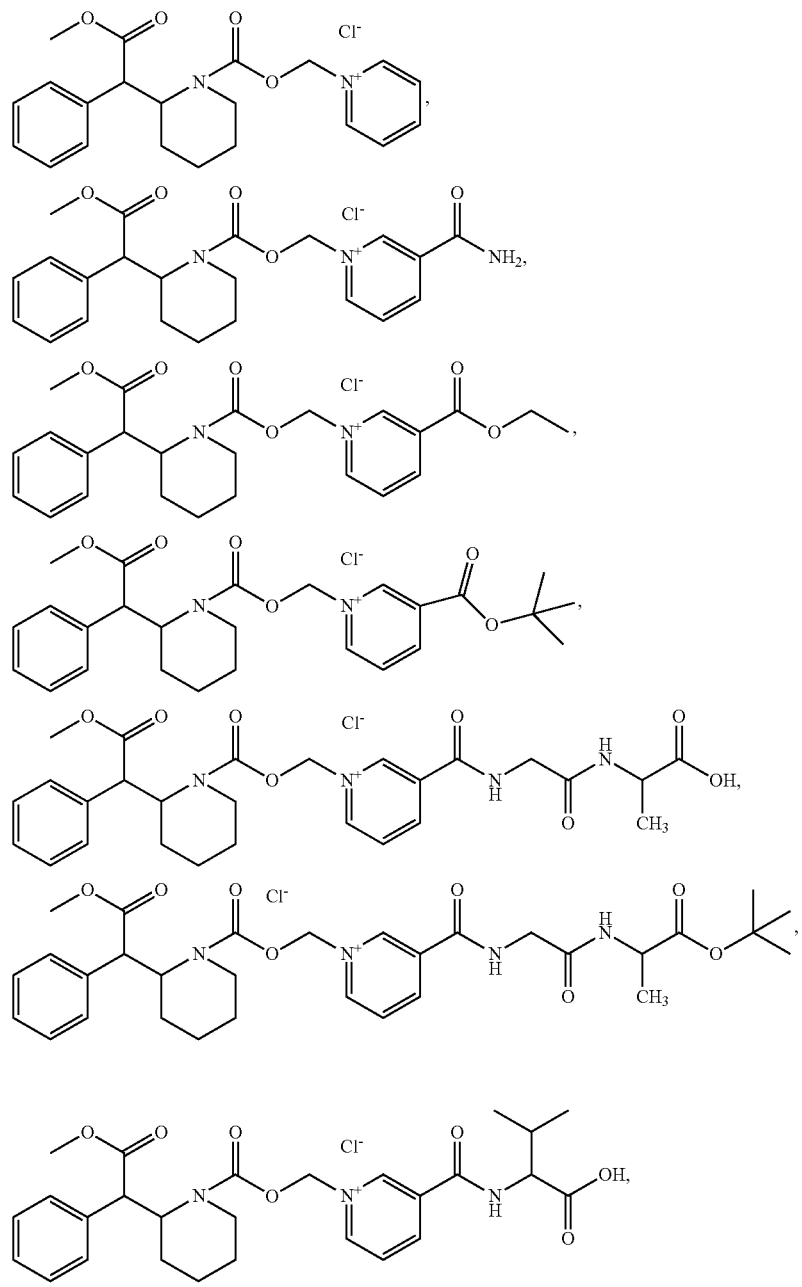

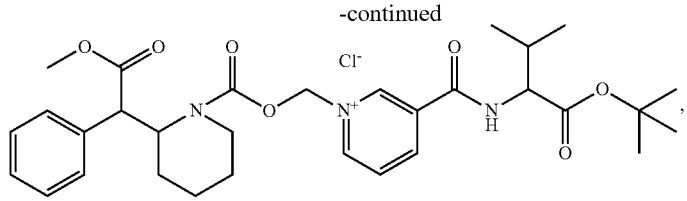
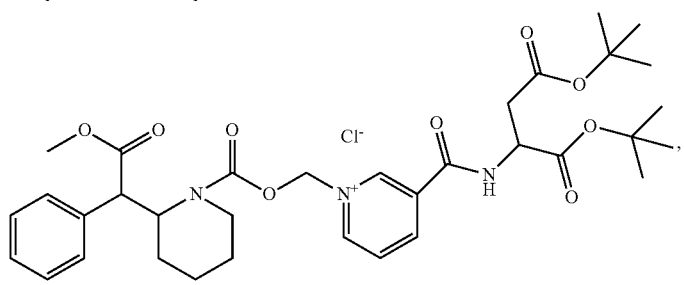
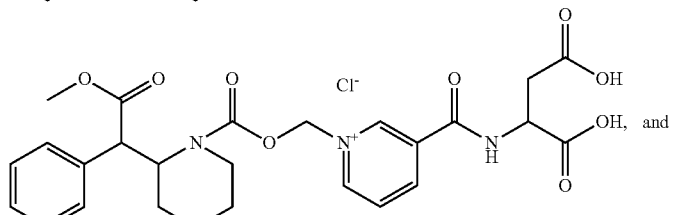
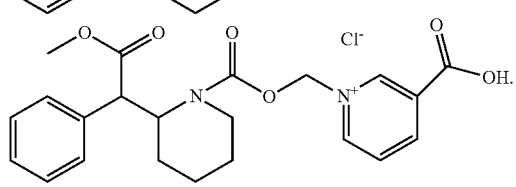
* * * * *